(12) United States Patent
Mitalipov et al.

(10) Patent No.: US 9,546,383 B2
(45) Date of Patent: Jan. 17, 2017

(54) HUMAN PLURIPOTENT EMBRYONIC STEM CELLS PRODUCED BY NUCLEAR TRANSFER USING A SOMATIC CELL NUCLEUS TREATED WITH HVJ-E EXTRACT AND AN OOCYTE FROM A DONOR CYCLE THAT PRODUCED 15 OR FEWER OOCYTES

(71) Applicants: Shoukhrat Mitalipov, Beaverton, OR (US); Masahito Tachibana, Miyagi (JP)

(72) Inventors: Shoukhrat Mitalipov, Beaverton, OR (US); Masahito Tachibana, Miyagi (JP)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 0 days.

(21) Appl. No.: 14/276,810

(22) Filed: May 13, 2014

(65) Prior Publication Data

US 2014/0335619 A1 Nov. 13, 2014

Related U.S. Application Data

(60) Provisional application No. 61/822,707, filed on May 13, 2013.

(51) Int. Cl.
| | | |
|---|---|---|
| *C12N 5/00* | (2006.01) | |
| *C12N 15/873* | (2010.01) | |
| *C12N 5/16* | (2006.01) | |
| *C12N 5/073* | (2010.01) | |
| *C12N 5/075* | (2010.01) | |
| *C12N 5/0735* | (2010.01) | |
| *C12N 15/877* | (2010.01) | |

(52) U.S. Cl.
CPC ........... *C12N 15/873* (2013.01); *C12N 5/0606* (2013.01); *C12N 5/16* (2013.01); *C12N 5/0603* (2013.01); *C12N 5/0609* (2013.01); *C12N 5/0611* (2013.01); *C12N 15/8776* (2013.01); *C12N 2502/02* (2013.01); *C12N 2506/02* (2013.01); *C12N 2517/04* (2013.01)

(58) Field of Classification Search
CPC . C12N 15/873; C12N 2517/04; C12N 5/0603; C12N 5/0606; C12N 5/0611; C12N 5/0609; C12N 2502/02; C12N 2506/02; C12N 15/8776

See application file for complete search history.

(56) References Cited

U.S. PATENT DOCUMENTS 7,972,849 B2    7/2011  Mitalipov
2012/0036591 A1 2/2012  Mitalipov

FOREIGN PATENT DOCUMENTS

WO    WO9408598 A1    4/1994

OTHER PUBLICATIONS

Liu et al. Genetic and epigenetic X-chromosome variations in a parthenogenetic human embryonic stem cell line. J. Assist. Reprod. Genet., 2011, vol. 28, 303-313.*
Sparman et al. Cloning of non-human primates: the road "less traveled by". Int. J. Devl. Biol., 2010, vol. 54, pp. 1671-1678.*
Fauser et al. Endocrine Profiles after Triggering of Final Oocyte Maturation with GnRH Agonist after Cotreatment with the GnRH Antagonist Ganirelix during Ovarian Hyperstimulation for in Vitro Fertilization. J. Clinical Endocrinology Metabolism, 2002, vol. 87, 709-715.*
Doucleff, M. Scientists Clone Human Embryos to Make Stem Cells. National Public Radio (NPR), May 15, 2013, All Things Considered. http://www.npr.org/sections/health-shots/2013/05/183916891/scientists-clone-human-embryos-to-make-stem-cells.*
Cyranoski D. Human Stem Cells Created by Cloning. Nature, 2013, vol. 497, pp. 295-296.*
Shively et al. The Unique Value of Primate Models in Translational Research. American Journal of Primatology, 2009, vol. 71:715-721.*
Gurdon JB, J Embryology Exp Morphology 10, 622-640 (1962).
Solter D, Nat Rev Genet 1, 199-207 (2000).
Wilmut I et al, Nature 419, 583-586 (2002).
Lanza RP et al, Nature Biotech 17, 1171-1174 (1999).
Yang X et al, Nature Genet 39, 295-302 (2007).
Kawahara et al, Reproduction 130, 351-357 (2005).
Lee and Campbell, Bio Reprod 74, 691-698 (2006).
Zhou et al, Science 302, 1179 (2003).
Amit et al, Devel Biol 227, 271-278 (2000).
Bongso et al, Hum Reprod 4, 706-713 (1989).
Egli D et al, Nat Comm 2, 488 (2011).
Noggle S et al, Nature 478, 70-75 (2011).
Fan Y et al, Stem Cells Dev 20, 1951-1959 (2011).
French AJ et al, Stem Cells 26, 485-493 (2008).
Byrne JA et al, Nature 450, 497-502 (2007).
Sparman M et al, Stem Cells 27, 1255-1264 (2009).
Mitalipov SM et al, Hum Reprod 22, 2232-2242 (2007).
Tachibana M et al, Nature 461, 367-372 (2009).
Ding X et al, Theriogenology 70, 622-630 (2008).
Kishigami S et al, Biochem Biophys Res Comm 183-189 (2006).
Li J et al, Theriogenology 70, 800-808 (2008).
Pellicer A et al, Hum Reproduction 4, 536-540 (1989).
Santos MA et al, Reproduction 139, 23-34 (2010).
van der Gaast MH et al, Reprod Biomed Online 13, 476-480 (2006).

* cited by examiner

*Primary Examiner* — Deborah Crouch
(74) *Attorney, Agent, or Firm* — Jeffrey M. Jackson

(57) ABSTRACT

Human pluripotent embryonic stem cells produced by somatic cell nuclear transfer as well as methods of making and using said human pluripotent embryonic stem cells are disclosed.

18 Claims, 31 Drawing Sheets hESO-NT2, 46XX hESO-NT3, 46XX hESO-NT4, 46XX

Somatic cell methylation memory
in reprogrammed cells

| Stem cell type | # of DMPs different from IVF-ESCs (q-value < 0.01) | # of DMPs shared with HDF* |
|---|---|---|
| iPSCs | 6478 | 780 |
| NT-ESCs | 110 | 87 |
| Shared between iPSCs/ NT-ESCs | 91 | 74 |

|Avg. β HDF - Avg. β IVF-ESC|>0.3 AND |Avg. β iPSC - Avg. β IVF-ESC|>0.3

HUMAN PLURIPOTENT EMBRYONIC STEM CELLS PRODUCED BY NUCLEAR TRANSFER USING A SOMATIC CELL NUCLEUS TREATED WITH HVJ-E EXTRACT AND AN OOCYTE FROM A DONOR CYCLE THAT PRODUCED 15 OR FEWER OOCYTES

PRIORITY CLAIM

This application claims the benefit of U.S. Provisional Patent Application 61/822,707, filed 13 May 2013.

FIELD

Generally, the field is human pluripotent stem cells. More specifically, the field is human pluripotent stem cells produced by somatic cell nuclear transfer and methods of making and using the same.

BACKGROUND

Cytoplasmic factors present in mature metaphase II arrested (MII) oocytes have a unique activity to reset the identity of transplanted somatic cell nuclei to the embryonic state. Since the initial discovery in amphibians (Gurdon J B, *J Embryology, Exp Morphology* 10, 622-640 (1962); incorporated by reference herein), SCNT success in a range of different mammalian species demonstrated that this reprogramming activity in enucleated oocytes (cytoplasts) is universal (Solter D, *Nat Rev Genet* 1, 199-207 (2000) and Wilmut I et al, *Nature* 419, 583-586 (2002); both of which are incorporated by reference herein). However, despite numerous applications of SCNT for animal cloning, the nature of reprogramming oocyte factors and the mechanism of their action remain largely unknown.

Pluripotent stem cells have been produced by somatic cell nuclear transfer in non-human primates (U.S. Pat. No. 7,972,849; incorporated by reference herein.) In humans, SCNT has been envisioned as a method of generating personalized embryonic stem cells from a patient's somatic cells that could be used to study the mechanisms of disease and ultimately to be used for cell based therapies (Lanza R P et al, *Nature Biotech* 17, 1171-1174 (1999) and Yang X et al, *Nature Genet* 39, 295-302 (2007); both of which are incorporated by reference herein). However, derivation of human nuclear transfer derived ESCs (NT-ESCs) has not been achieved, despite numerous attempts over the past decade.

SUMMARY

Disclosed herein is the production of human embryonic stem cells derived from somatic cell nuclear transfer. The method of producing the cells involves: enucleating a human oocyte by removing the MII spindle by any manner that does not lower levels of maturation promoting factor. This action produces a cytoplast. A polarized microscope can be used in this procedure. The method further involves contacting a human donor nucleus with an HVJ-E extract and also contacting the cytoplast with the human donor nucleus, thereby producing an SCNT embryo. The donor nucleus can be provided in the context of a donor cell, such as a fibroblast. In some examples of the method, the donor cell can be treated with a protease such as trypsin, thereby producing a desegregated donor cell.

In addition, the method involves treating the human oocyte and/or the cytoplast and/or the SCNT embryo with a protein phosphatase inhibitor. The protein phosphatase can be any protein phosphatase inhibitor, including caffeine. In some examples, the protein phosphatase inhibitor is present during both the enucleation of the human oocyte and the contacting of the SCNT embryo with the donor nucleus. In further examples, the caffeine is present at a concentration of at least 1.25 mM. In still further examples, the caffeine is present at a concentration of between 1.25 mM and 2.5 mM.

The method further involves applying at least one electroporation pulse to the SCNT embryo, thereby activating the SCNT embryo. The activated SCNT embryo is cultured in a first media that includes 6-DMAP. The activated SCNT embryo is also cultured in a second media that includes TSA. The activated SCNT embryo is cloned in a third media, thereby producing a blastocyst. The blastocyst is cultured on a feeder layer, and cells with embryonic stem cell like morphologies are selected therefrom. In further examples, the cells with embryonic stem cell like morphologies are further characterized as having donor nucleus nuclear DNA and oocyte donor mitochondrial DNA.

In some examples, oocytes are selected from a donation cycle of 15 or fewer oocytes, from donation cycles of 10 or fewer oocytes, and/or from oocyte donors treated with a GnRH inhibitor such as ganirelix. In further examples, the method involves collecting the human oocyte from the oocyte donor.

It is an object of the invention to provide human pluripotent stem cells that have improved epigenetic reprogramming relative to those produced by transcription-factor based reprogramming (induced pluripotent stem cells).

It is an object of the invention to provide human pluripotent stem cells that are genetically identical to a subject providing a donor nucleus that are more similar to human pluripotent stem cells produced by in vitro fertilization than those produced by transcription-factor based reprogramming.

BRIEF DESCRIPTION OF THE DRAWINGS

FIG. 1A is a cartoon and image depicting the effect of donor cell introduction by electrofusion or HVJ-E fusion on somatic cell nuclear remodeling. NEBD and PCC were associated with HVJ-E-based fusion but not with electrofusion.

FIG. 1B is a cartoon depicting a schematic representation of a study testing for the results of electroporation on proper activation and SCNT blastocyst formation.

FIG. 1C is a bar graph depicting the results of the study in FIG. 1B. (See also FIG. 8, and Tables 1 and 2).

FIG. 2A is an image depicting the morphology of nuclear donor fetal fibroblasts before SCNT.

FIG. 2B is an image depicting a poor quality human SCNT blastocyst without distinct ICM.

FIG. 2C is an image depicting spindle-like structures detected when donor nuclei are introduced into intact MII oocytes but not after enucleation. Arrowhead and arrow point at the maternal MII spindle and somatic cell spindle, respectively.

FIG. 2D is an image depicting somatic cell spindles formed in cytoplasts when oocyte enucleation and fusion were conducted in presence of caffeine.

FIG. 2E is an image depicting a human SCNT blastocyst with a prominent ICM (asterisk) produced after caffeine treatment.

FIG. 2F is an image depicting a NT-ESC colony with typical ESC morphology derived from caffeine treated SCNT human embryos.

FIG. 3A is a bar graph depicting the percentage of SCNT embryos developing into blastocysts with and without caffeine treatment.

FIG. 3B is a bar graph depicting the development of NT-ESCs from blastocysts with and without caffeine treatment.

FIG. 4A is a bar graph depicting vitro development of SCNT embryos produced with skin cells from Leigh's disease patient. The donor cells were fused with embryos from two different oocyte donors as indicated. Fifteen MII oocytes were retrieved from egg donor #11 and only five oocytes were collected from the donor #12. SCNT blastocysts were generated from both oocyte cohorts.

FIG. 4B is a bar graph depicting the NT-ESC derivation efficiency from oocytes from each donor.

FIG. 5A is a bar graph depicting human SCNT development grouped according to the number of oocytes collected from each cycle. Cycles producing 10 or less oocytes were associated with improved development of SCNT embryos.

FIG. 5B is a bar graph depicting the result that the efficacy of NT-ESC derivation is dependent on the number of oocytes collected from a cycle.

FIG. 5C is a bar graph depicting the outcome of SCNT embryo development grouped according to whether or not the oocyte donor received a GnRH agonist or a GnRH antagonist. Blastocyst development was improved from oocyte donors receiving a GnRH antagonist.

FIG. 5D is a bar graph depicting the outcome of NT-ESCs grouped according to whether or not the oocyte donor received a GnRH agonist or a GnRH antagonist.

FIG. 6A is a table depicting the results of nuclear DNA genotyping from four human NT-ESC lines (hESO-NT1, -NT2, -NT3 and -NT4) determined by microsatellite parentage analysis. A total of 24 microsatellite markers were used for each cell typing. The representative markers for D2S1333 and D4S413 loci demonstrate that the nuclear DNA in these cell lines was exclusively derived from the somatic HDF-f cell line. No contribution of oocyte nuclear DNA was detected.

FIG. 6B, is a trace resulting from mtDNA genotyping by Sanger sequencing which demonstrated that all NT-ESC lines contain oocyte mtDNA.

FIG. 6C is an image of the results of a cytogenetic G-banding analysis that confirmed all NT-ESCs exhibit normal 46XX karyotype.

FIG. 6D is a set of 8 images showing that human NT-ESCs express standard pluripotency markers detected by immunocytochemistry for antibodies against OCT4, NANOG, SOX2, SSEA4, TRA-1-60 and TRA-1-81. Original magnification was 200×.

FIG. 6E is a set of two images depicting histological analysis of teratoma tumors produced after injection of human NT-ESCs into SCID mice. An arrow and arrowhead in the upper panel indicate Intestinal-type epithelium with goblet cells (endoderm) and cartilage (mesodermal), respectively. An arrow and arrowhead in the lower panel depict neuroectodermal (ectoderm) and muscle (mesoderm) tissues, respectively. Original magnification was ×200.

FIG. 7A is a scatter plot analysis comparing expression profiles of human NT-ESCs (hESO-NT1) with IVF-derived ESC controls (hESO-7) and parental dermal fibroblasts (HDF-f). NT-ESCs displayed low transcriptional correlation to fibroblasts but were similar to ESCs derived from fertilized embryos.

FIG. 7B is a tree diagram depicting the linkages between NT-ESCs and IVF-ESCs.

DETAILED DESCRIPTION

Figure 1A:
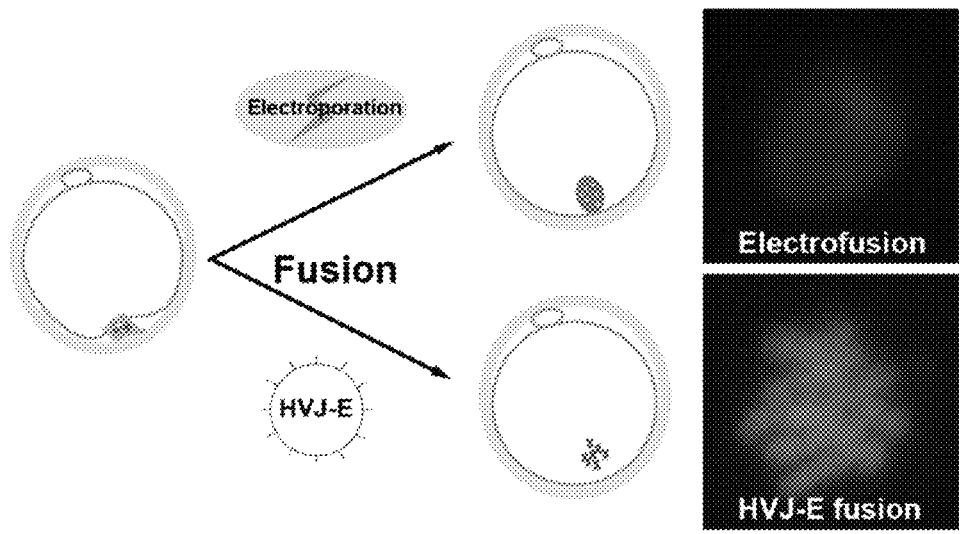
FIGS. 1A, 1B, and 1C collectively show optimization of SCNT protocols using a rhesus monkey model.

Human pluripotent stem cells produced by somatic cell nuclear transfer are disclosed herein. Methods of making and using these pluripotent stem cells are also disclosed.

Unless defined otherwise, all technical and scientific terms used herein have the same meaning as is commonly understood by one of ordinary skill in the art to which this invention belongs.

The term "nuclear genetic material" refers to structures and/or molecules found in the nucleus that comprise polynucleotides (e.g., DNA) that encode information about the individual. Nuclear genetic material includes, but is not limited to, chromosomes and chromatin. The term includes nuclear genetic material produced by cell division such as the division or a parental cell into daughter cells. Thus, a cell includes nuclear genetic material derived from a donor somatic cell if the cell has been produced during mitosis or meiosis from an original cell, or if the nuclear genetic material has been transferred into an enucleated cytoplast via somatic cell nuclear transfer.

The term "mitochondrial DNA" or "mtDNA" refers to the DNA of the mitochondrion, a structure situated in the cytoplasm of the cell rather than in the nucleus (where all the other chromosomes are located). In vivo, all mtDNA is inherited from the mother. There are 2 to 10 copies of the mtDNA genome in each mitochondrion. Mitochondrial DNA is a double-stranded, circular molecule. It is very small relative to the chromosomes in the nucleus and includes only a limited number of genes, such as those encoding a number of the subunits in the mitochondrial respiratory-chain complex and the genes for some ribosomal RNAs and transfer RNAs. A cell includes mtDNA derived from the continued replication cytoplasmically based mitochondria, which in the case of SCNT are based in the recipient cytoplast.

The term "DNA methylation" refers to the postsynthetic addition of methyl groups to specific sites on DNA molecules; the reaction is catalyzed by enzymes called DNA methyltransferases that are specific for nucleotide and position of methylation. In eukaryotes, methylation is involved in gene expression, and plays a role in a variety of epigenetic mechanisms, including development, X chromosome inactivation, genomic imprinting, mutability of DNA, and uncontrolled cell growth in cancer.

The term "X chromosome inactivation" refers to the inactivation of one of each pair of X chromosomes to form the Barr body in female mammalian somatic cells. Thus tissues whose original zygote carried heterozygous X borne genes should have individual cells expressing one or other but not both of the X encoded gene products. The inactivation is thought to occur early in development and leads to mosaicism of expression of such genes in the body.

The phrase "dosage compensation" refers to a mechanism that senses gene dosage and regulates expression accordingly. In mammals there is monoallelic expression of X-linked genes that differ in dose between females (XX) and males (XY). "XIST" refers to a gene encoding a large non-coding RNA which has been shown to be necessary for developmentally regulated X chromosome silencing in females. The XIST RNA is about 18 kb and is not translated, it is spliced, and polyadenylated. It is also organized into blocks of repetitive sequence. In vivo, XIST RNA is found to be stably associated with the silenced X chromosome. The expression of XIST RNA is always cis-limited, and is associated with the silenced X chromosome in females.

The term "effective amount" or "therapeutically effective amount" refers to the amount of agent or a cell that is sufficient to prevent, treat, reduce and/or ameliorate the symptoms and/or underlying causes of any disorder or disease, or the amount of an agent sufficient to produce a desired effect on a cell. In one embodiment, a "therapeutically effective amount" is an amount of a cell or an agent sufficient to reduce or eliminate a symptom of a disease. In another embodiment, a therapeutically effective amount is an amount sufficient to overcome the disease itself.

As used herein, the term "preparation," "purified preparation," "isolated preparation," "isolated population" or "purified population" of pluripotent human stem cells refers to a preparation of one or more cells that has been manipulated to provide a preparation of cells that is substantially free of additional components. In some embodiments, the cell preparation is at least about 60%, by weight or number, free from other components that are present when the cell is produced, such as other types of cells. In various embodiments, the cell is at least about 75%, or at least about 85%, or at least about 90%, or at least about 95%, or at least about 99%, by weight or number, pure. A purified cell preparation can be obtained, for example, by purification (e.g., extraction) from a natural source, fluorescence-activated cell-sorting, or other techniques known to the skilled artisan. Purity can be assayed by any appropriate method, such as fluorescence-activated cell sorting (FACS) or by visual examination.

The cells described herein progress through a series of divisions into a blastocyst in vitro. The blastocyst comprises an inner cell mass (ICM) and a trophoblast. The cells found in the ICM give rise to pluripotent stem cells that possess the ability to proliferate indefinitely, or if properly induced, differentiate in all cell types contributing to an organism.

As used herein, the term "pluripotent" refers to a cell's potential to differentiate into cells of the three germ layers: endoderm (e.g., interior stomach lining, gastrointestinal tract, the lungs), mesoderm (e.g., muscle, bone, blood, urogenital), or ectoderm (e.g., epidermal tissues and nervous system). Pluripotent stem cells can give rise to any fetal or adult cell type including germ cells. However, PSCs alone cannot develop into a fetal or adult animal when transplanted in utero because they lack the potential to contribute to extra embryonic tissue (e.g., placenta in vivo or trophoblast in vitro).

PSCs are the source of multipotent stem cells (MPSCs) which arise through spontaneous differentiation or as a result of exposure to differentiation induction conditions in vitro. The term "multipotent" refers to a cell's potential to differentiate and give rise to a limited number of related, different cell types. These cells are characterized by their multi-lineage potential and the ability for self-renewal. In vivo, the pool of MPSCs replenishes the population of mature functionally active cells in the body. Among the exemplary MPSC types are hematopoietic, mesenchymal, or neuronal stem cells.

Transplantable cells include MPSCs and more specialized cell types such as committed progenitors as well as cells further along the differentiation and/or maturation pathway that are partly or fully matured or differentiated. "Committed progenitors" give rise to a fully differentiated cell of a specific cell lineage. Exemplary transplantable cells include pancreatic cells, epithelial cells, cardiac cells, endothelial cells, liver cells, endocrine cells, and the like.

A "feeder layer" refers to non-proliferating cells (such as irradiated cells) that can be used to support proliferation of pluripotent stem cells. Protocols for the production of feeder layers are known in the art, and are available on the internet, such as at the National Stem Cell Resource website, which is maintained by the American Type Culture Collection (ATCC). As used herein, the term "embryo" refers generally to a cellular mass obtained by one or more divisions of a zygote or an activated oocyte with an artificially reprogrammed nucleus. A "morula" is the preimplantation embryo 3-4 days after fertilization, when it is a solid mass, generally composed of 12-32 cells (blastomeres). A "blastocyst" refers to a preimplantation embryo in placental mammals (about 3 days after fertilization in the mouse, about 5 days after fertilization in humans) of about 30-150 cells. The blastocyst stage follows the morula stage, and can be distinguished by its unique morphology. The blastocyst is generally a sphere made up of a layer of cells (the trophectoderm), a fluid-filled cavity (the blastocoel or blastocyst cavity), and a cluster of cells on the interior (the ICM).

"Genomic imprinting" refers to a mammalian epigenetic phenomenon whereby the parental origin of a gene determines whether or not it will be expressed. Over 75 imprinted genes have been identified, many of which are noncoding RNAs that are hypothesized to control the expression of linked protein coding genes that are also imprinted. Generally, allele-specific methylation of CpG dinucleotides is a mechanism that regulates gene expression of imprinted genes. "Maternally expressed" refers to a gene that is expressed from the copy inherited from the mother. Imprinted genes include, but are not limited to the maternally expressed imprinted genes H19, CDKNIC, PHLDA2, DLX5, ATP10A, SLC22A18 or TP73. Paternally expressed imprinted genes include but are not limited to IGF2, NDN, SNRPN, MEST, MAGEL2, and PEG3. Exemplary sequence information for these genes, including the human nucleic acid sequences, can be found at the gene imprint website, available on the Internet; this information is incorporated by reference herein.

Lamin refers to the major non-collagenous component of the basal lamina. It is a glycoprotein that has an "A" chain and two "B" chains. Lamins are fibrous proteins providing structural function and transcriptional regulation in the cell nucleus. A-type lamins are only expressed following gastrulation. Lamins A and C are the most common A-type lamins and are splice variants of the LMNA gene.

"Maturation promoting factor" (MPF) refers to a heterodimeric protein comprising cyclin B and cyclin-dependent kinase 1 (p34cdc2) that stimulates the mitotic and meiotic cell cycles. MPF promotes the entrance into mitosis from the G2 phase by phosphorylating multiple proteins needed during mitosis. MPF is activated at the end of G2 by a phosphatase which removes an inhibitory phosphate group added earlier. Targets for MPF include condensing, which enable chromatin condensation; various microtubule-associated proteins involved in mitotic spindle formation; lamins, whose interaction contribute to the degradation of the nuclear envelope as well as the histones H1 and H3; and the Golgi matrix, to cause fragmentation.

"Nuclear reprogramming" results in immediate inhibition of transcription in the transferred somatic cell nucleus and the subsequent establishment of temporal and spatial patterns of embryonic gene expression associated with normal development. Currently unidentified reprogramming factors present in oocytes are capable of initiating a cascade of events that can reset the epigenetic program of specialized somatic cells back to an undifferentiated state.

"Nuclear remodeling" refers to morphological and biochemical changes in nuclear material occurring soon after introduction of somatic cell nucleus into an enucleated, nonactivated, mature oocyte. Nuclear remodeling includes but is not confined to nuclear envelope breakdown (NEBD), followed by premature chromosome condensation (PCC) and spindle formation.

"Nuclear transfer" refers to the insertion of a donor nucleus into an enucleated recipient host cell.

"Telomere" refers to the sequences and the ends of a eukaryotic chromosome, consisting of many repeats of a short DNA sequence in specific orientation. Telomere functions include protecting the ends of the chromosome so that chromosomes do not end up joined together and allowing replication of the extreme ends of the chromosomes (by telomerase). The number of repeats of telomeric DNA at the end of a chromosome decreases with age and telomeres play roles in aging and cancer. "Telomerase" refers to a DNA polymerase involved in the formation of telomeres and the maintenance of telomere sequences during chromosome replication.

"HVJ-E extract" refers to inactivated viral envelope from the Haemagglutinating virus of Japan. HVJ is also referred to as Sendai virus.

"6-DMAP" refers to 6-Dimethylaminopurine.

"TSA" refers to trichostatin A.

Human Pluripotent and Multipotent Stem Cells

Compositions of human PSCs are provided herein. The PSCs are capable of extended propagation in vitro without losing their ability to differentiate into ectoderm, mesoderm and endoderm. The PSCs can have been generated and stored in the course of their use and/or propagation, such as by freezing. These PSCs can be isolated, and thus can be propagated in vitro.

In some examples, the human PSCs are capable of proliferating for at least 4 or more cell divisions in vitro wherein the PSC maintains its pluripotency. In other embodiments, the PSCs are capable of proliferating at least 5, 6, 7, 8 or more cell divisions, wherein the PSCs maintain their pluripotency. In other examples, the PSCs are capable of proliferating in vitro for at least about 1 month or more, while maintaining pluripotency. In additional examples, the human PSCs are capable of proliferating in vitro for at least about 2, 3, or 4 months or more, wherein the cell maintains its pluripotency. In other embodiments, the PSCs are capable of proliferating in vitro for at least about 5, 6, or 7 months or more, wherein the PSCs maintain their pluripotency. In another embodiment, the PSCs are capable of proliferating in vitro for at least about 8 months or more, wherein the PSCs maintain their pluripotency. In a further embodiment, the PSCs are capable of proliferating in vitro for at least about 9 months or more, wherein the PSCs maintain their pluripotency. The methods of obtaining and culturing these cells are provided in greater detail below.

In addition, the human pluripotent stem cells possess any one or more (including all) of the characteristic morphology: high nuclear/cytoplasmic ratios, prominent nucleoli, and compact colony formation. The pluripotent cells can be characterized by the presence of discrete cell surface markers or transcription factor expression that includes one or more (including all) of the following: OCT-4, SSEA-3, SSEA-4, TRA-1-60, and TRA-1-81. These cells are also characterized by mRNA expression of all or one or more (including all) of the following: POU5FI (OCT4), NANOG, SOX-2, TDGF, THY1, FGF4, TERT and LEFTYA. The human pluripotent stem cells can also be characterized by the mRNA and/or protein expression of one or more (including all) of nuclear factor (erythroid-derived 2)-like 3 (NFE2L3), nuclear receptor subfamily 5, group A, member 2 (NR5A2), lymphocyte specific protein tyrosine kinase (LCK), V set domain containing T cell activation inhibitor 1 (VTCNI), developmental pluripotency associated 4 (DPPA4), solute carrier family 12 (SLC12AI), C14orf115, myosin VIIA and rab interacting protein (MYRIP), alcohol dehydrogenase 4 (ADH4) and PR-domain containing 14 (PRDM14) (See the GENECARD® website, GENBANK® and iHOP® web sites, available on the internet. Exemplary amino acid sequences and nucleic acid sequences are provided in GENBANK® as of May 8, 2013).

In addition to marker and transcription factor expression profiles, the human pluripotent stem cells can also maintain a normal diploid karyotype. Both XX and XY cell lines can be derived. A normal karyotype is one where all chromosomes normally present in a species are present and have not been noticeably altered. Normal karyotype typically refers to the absence of chromosomal translocations, deletions or insertions. The normal karyotype is readily determined by any method known to one of skill in the art, such as any banding technique, such as G-banding and/or fluorescence in situ hybridization (FISH) for detecting translocation. The human pluripotent stem cells disclosed herein have a karyotype that is stable throughout in vitro culturing. In addition, the karyotype remains stable even when the PSCs are cultured to differentiate into organ-specific cells and used for treatment purposes, such as for transplantation.

The PSCs can be propagated as a self-renewing cell line as well as provide a renewable source of MPSCs and other transplantable cells. PSCs can differentiate under appropriate conditions into the germ cell lineage and viable gametes and three embryonic germ layers; mesoderm (for example, bone, cartilage, smooth muscle, striated muscle, and hematopoietic cells); endoderm (for example, liver, primitive gut and respiratory epithelium); ectoderm (for example, neurons, glial cells, hair follicles and tooth buds). One of skill in the art is familiar with how to assess the ability of PSCs to differentiate into cells of the three germ layers. In one example, stem cells are implanted into an animal model, such as a nude mouse, and the cells are allowed to grow and form teratomas. After a suitable amount of time, the teratomas are removed, sectioned and stained to ascertain the layers that have formed. If the cell is pluripotent, the resulting teratoma will contain tissues from each of the three germ layers. In another example the PSCs are cultured in defined conditions in vitro to differentiate into specific cell types.

The human pluripotent stem cells disclosed herein are distinguished from other human pluripotent stem cells described previously in that they are generated by transferring nuclear genetic material from the somatic cell of one individual (such as a patient) into a recipient cell, such as an oocyte, from another individual. That is, the stem cells derive their nuclear genetic material from the subject of interest, while the enucleated recipient (or host) cell is from a different donor which provides mitochondrial DNA.

For example, the PSCs and MPSCs generated using the methods disclosed herein will have essentially identical nuclear genetic material to the subject who is the source of the donor nuclear genetic material, and as such autologous transplantation of differentiated cells derived from the stem cells should not induce immune rejection when transplanted back into the donor.

The PSCs disclosed herein do not include human stem cells that have been generated using solely sperm-fertilized oocytes, and thus have an equal contribution from two separate individuals (parents). Methods of determining whether a stem cell has derived its nuclear genetic material from one individual are readily known to one of skill in the art, including, but not limited to, microsatellite analysis. The human pluripotent (or multipotent) stem cells disclosed herein have mitochondrial DNA from one individual and the nuclear DNA from a second, different individual. In one embodiment, the cells do not include mitochondrial DNA from the first individual of interest. Thus, in one example, the mitochondrial DNA and the nuclear DNA of the human pluripotent stem cells (or multi potent stem cells) are from different individuals of the same species.

Disclosed herein is a purified preparation of human PSCs which (a) is capable of being cultured for more than about one month in vitro; (b) maintains a normal karyotype; and (c) is capable of differentiating into germ cells, ectoderm, mesoderm, and endoderm layers; wherein said pluripotent stem cells are derived from an enucleated cell from a first donor and the nuclear genetic material from a second donor. The purified preparation of human PSCs can possess one or more (including all) of the following characteristics: (a) is capable of being cultured for more than 4 months in vitro; (b) maintains a normal karyotype; (c) is capable of differentiating into germ cells, ectoderm, mesoderm, and endoderm layers; and (d) derives its nuclear genetic material from a single individual.

Compositions are disclosed that comprise one or more isolated pluripotent human stem cells which possess one or more (including all) of the following characteristics: (a) are capable of being cultured for more than 1, 2, 3, 4, 5, or 6 months in vitro; (b) maintain a normal karyotype while in culture; (c) are capable of differentiating into the germ cell lineage, ectoderm, mesoderm, and endoderm layers; and (d) derive their nuclear genetic material from one individual. In some examples, the pluripotent stem cells can be characterized by the presence of mitochondrial DNA from an enucleated cell from a first donor and the nuclear genetic material from a second donor.

Multipotent stem cells produced from these human pluripotent stem cells and stem cell lines are disclosed herein. These multipotent cells are not pluripotent and give rise to cells of a specific lineage. In several embodiments, the multipotent stem cells are capable of proliferating at least 5, 6, 7, 8 or more cell divisions while retaining multipotency. In additional embodiments, the multipotent stem cells are capable of being cultured for more than about 1, 2, 3, 4, 5, or 6 months in vitro. The disclosure also encompasses compositions, including, but not limited to, pharmaceutical compositions, comprising isolated multipotent cells which have been derived from one or more human pluripotent stem cells which possess one or more (including all) of the following characteristics: (a) are capable of being cultured for more than 1, 2, 3, 4, 5, or 6 months in vitro; (b) maintains a normal karyotype while in culture; (c) are capable of differentiating into germ cells, ectoderm, mesoderm, and endoderm layers; and (d) derive their nuclear genetic material from one individual and their mitochondrial DNA from a second individual. In one aspect, pluripotent stem cells are derived from an enucleated cell from a first human and the nuclear genetic material from a second human, and multipotent stem cells are generated from these pluripotent cells.

Also provided herein are pluripotent human stem cell lines which possess one or more (including all) of the following characteristics: (a) are capable of 4 or more cell divisions in vitro; (b) maintain a normal karyotype while in culture; (c) are capable of differentiating into germ cells, ectoderm, mesoderm, and endoderm layers; and (d) derive its nuclear genetic material from one human donor and its mitochondrial genetic material from another human donor.

Purified preparations of human pluripotent stem cells and multipotent cells are provided herein which have been generated using somatic cell nuclear transfer (SCNT). The successful generation of such cells generally requires nuclear remodeling of the donor nucleus. The methods disclosed herein enable one of skill in the art to achieve success in nuclear remodeling.

The indication that a cell is undergoing nuclear remodeling is generally known to one of skill in the art and involves events such as premature chromatin condensation and nuclear envelope breakdown.

SCNT provides a way to produce isogenic cells of any cell type from a donor. Thus, provided are a preparation that comprises one or more pluripotent stem cells, or transplantable, cells that genetically match to the nuclear donor cell. By genetically match, it is understood that a 100% genetic match is not required but that that there is at least about a 99.5% match. In some examples, the genetic match is at least about 99%, at least about 98%, at least about 97%, at least about 96%, at least about 95%, and at least about 94%. In other cases, the genetic match will be at least about 90% match. In one example, the genetic match is at one major histocompatibility (MHC) locus. In other examples, the match is at one or more MHC loci. In yet other examples, the genetic match is at 2, 3, 4, 5, 6 or more MHC loci. In still further examples, the genetic match is also at the minor histocompatibility loci.

Cell lines can also be derived from multipotent stem cells or other transplantable cells derived from pluripotent stem cells. Also provided herein are preparations of transplantable cells derived from PSCs. These cells include, but are not limited to, neurons, cardiomyocytes, hematopoietic cells, keratinocytes, islet cells, mature gametes (sperm or oocytes) or any other cell type, including any cell type of an organism. In some embodiments, the purified preparation of transplantable cells is incorporated into a pharmaceutical composition or used in a method of treatment. The pharmaceutical composition can have additives, carriers, media components or other component in addition to the human transplantable cells.

Thus, compositions of human PSCs, MPSCs or transplantable cells and cell lines derived from them are provided herein.

Methods

Methods of obtaining and culturing human pluripotent stem cells are provided.

The methods require the successful accomplishment of the following: (a) effecting complete or essentially complete removal of the nuclear genetic material from a recipient cell which can be to provide an enucleated host cytoplast; (b) introduction of a nucleus from a somatic cell from the donor into the enucleated host cell cytoplast to form an SCNT embryo; and (c) that both (a) and (b) be carried out under conditions such that, upon nuclear remodeling of the introduced somatic cell nucleus in the cytoplasm of the host cell and the induction of activation, the resulting SCNT embryo exhibits the properties of a sperm-fertilized embryo such that subsequent mitotic cell division leads to the development of a blastocyst from which PSCs can be derived under culture conditions which typically sustain cultures of conventional embryonic stem cell (ESC) lines derived from sperm-fertilized embryos, ultimately resulting in viable cultures of pluripotent stem cells. Generally the nuclear donor and the recipient cell (such as an oocyte) are from different individuals.

Any suitable cell can serve as a source for the enucleated host cell cytoplast provided that it permits sufficient nuclear reprogramming of the donor somatic cell nucleus. In general, the host cell is an unfertilized oocyte, but the donor can also be a pluripotent ESC cytoplast.

If oocytes are used as the cell to be enucleated, then one important aspect of methodology is to use high quality oocytes. High quality oocytes can be obtained by using protocols that stimulate the donor to produce a number of viable oocytes. Examples of such stimulation protocols are described in the Examples below. Another aspect that is important for ultimate success in developing pluripotent stem cells is the method of harvesting. In one example, the oocytes can be harvested using methods known in the art, such as follicular aspiration, and then separated from contaminating blood cells. As an alternative, oocytes can be generated from PSCs in vitro.

In one example, when human donors are stimulated to produce oocytes (such as hormonally) and these oocytes are harvested, the oocytes that are collected can be in different phases. Some oocytes are in metaphase I while other oocytes are in metaphase II. In such cases, the oocytes that are in metaphase I can be put into culture until they reach metaphase II and then used for enucleation to serve as the host cell.

Optionally, the oocytes that have been cultured to reach metaphase II are combined with the oocytes that were already at metaphase II when harvested for a pool of potential host cells. In other cases, only the oocytes that are in metaphase II from the harvest are used for enucleation. Any of these oocytes can be frozen for further use.

In some examples, the enucleation of the host cell is accomplished using a technique that avoids an inhibition or down-regulation of maturation promoting factor (MPF) or its activity. The enucleation of the host cell refers to meiotic spindle removal. Maturation promoting factor or MPF is a heterodimeric protein comprising cyclin B and cyclin-dependent kinase 1 (p34cdc2) that stimulates the mitotic and meiotic cell cycles. Without being bound by theory, MPF promotes the entrance into mitosis from the G2 phase by phosphorylating multiple proteins needed during mitosis.

The technique employed to enucleate the cell comprise using any imaging system that avoids reducing the MPF levels or activity. MPF activity or levels can be determined by looking for biological effects that indicate activation has occurred. Such effects include chromatin condensation and nuclear envelope breakdown. It is further contemplated that the SCNT techniques useful in the method provided herein include not only those that directly impact MPF levels or activity, but also those that indirectly affect MPF levels or activity.

In some examples, removal of nuclear genetic material (i.e., enucleation) is accomplished without lowering the levels of maturation promoting factor (MPF) or its activity. In one example, this means that the enucleation is accomplished without the use of UV-based enucleation procedures such as Hoechst 33342 staining followed by UV visualization. One method that can be used in lieu of Hoechst 33342 is real time spindle imaging. In one example, the enucleation technique employs the real time spindle imaging system such as the OOSIGHT™ Imaging System (CRI, Inc. Woburn, Mass.). This system utilizes a wavelength of 545 nm and has diffraction limited spatial resolution. The relay optics are 0.65×. Generally the system includes a circular polarized interference filter with tunable liquid crystal polarizing filters However, any system that includes a liquid crystal tunable fiberoptic, a circular polarizer/green interference fiber optic, and optionally a CCD camera with software for image acquisition and analysis can be used for this purpose. Generally, the system can merge polarized light imaging with single point analysis by quantifying magnitude and orientation of birefringence at each pixel in a field, in about real time. The spindle and the zona pellucida of an oocyte display an intrinsic property termed "birefringence" when trans-illuminated with polarized light, is a property that can be used for efficient visualization and also enucleation. The use of such a real time system permits non-invasive visualization and the complete, or essentially complete, removal of nuclear material from the oocyte or other cell. In one example, the entire mitotic spindle and its associated DNA from the host cell is removed such that any potential for generating parthenotes is reduced or eliminated altogether.

In addition, exposure to caffeine, a protein phosphatase inhibitor (Kawahara et al, *Reproduction* 130, 351-357, (2005); Lee and Campbell, *Bio Reprod* 74, 691-698 (2006); both of which are incorporated by reference herein) or the proteasome inhibitor, MG-132 (Zhou et al, *Science* 302, 1179 (2003); incorporated by reference herein) increases the activity of MPF. MG-132 can be utilized in the methods disclosed herein at concentrations, for example, of about 0.1 to 10 µM, such as about 0.5 to about 10 µM, such as about 0.5 to about 5 µM, such as about 1 to about 3 µM, such as about 1 to about 2 µM. In some examples, 0.2, 2 or 5 µM MG-132 can be utilized. Caffeine can be used, for example at concentrations of about 0.25 mM to about 25 mM, such as about 0.5 mM to 10 mM, such as 0.5 mM to 2.5 mM, such as about 1.25 mM.

Any suitable somatic cell can be used as the source of the donor nucleus. It will be appreciated by those skilled in the art that the selection of the somatic cell type from the donor to be the source of the nucleus for SCNT is not critical and can be selected from cells that can be removed in appropriate quantities from the donor without significant discomfort or risk. Exemplary somatic cells include, but are not limited to keratinocytes, white blood cells, skin cells, and adipose cells. In one embodiment, the donor somatic cell nucleus can include modified nucleic acids, such as nucleic acid (e.g., DNA) that includes a recombinant product. In one non-limiting example, the donor nucleus is obtained from a transgenic animal or an animal with an engineered knock-out mutation. In a further example, the donor nucleic acid includes heterologous DNA that encodes a protein product, such as a detectable marker, enzyme, or other protein. The donor nucleic acid can also include other nucleic acids, such as ribozymes or antisense nucleic acid sequences. The heterologous nucleic acid can also be a regulatory sequence, such as a promoter, enhancer, insulator or repressor. Techniques for modifying nucleic acids are well known in the art, and include inserting a DNA that is synthetic or from another organism into the donor nucleic acid, deleting one or more DNA sequences from the donor, and introducing mutations, such as point mutations into the donor nucleic acid. Methods and tools for manipulation of nucleic acids are well known in the art, see for example *Molecular Cloning: A Laboratory Manual, second edition* (Sambrook et al, 1989) Cold Spring Harbor Press; *Oligonucleotide Synthesis* (M. J. Gait, ed., 1984); *Animal Cell Culture* (R. I. Freshney, ed., 1987); *Methods in Enzymology* (Academic Press, Inc.); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al, eds., 1987); *PCR: The Polymerase Chain Reaction*, (Mullis et al., eds., 1994); *Current Protocols in Immunology* (J. E. Coligan et al., eds., 1991) *Short Protocols in Molecular Biology* (Wiley and Sons, 1999), *Embryonic Stem Cells: A Practical Approach* (Notaranni et al. eds., Oxford University Press 2006); and *Essentials of Stem Cell Biology* (R. Lanza, ed., Elsevier Academic Press 2006).

In another example, for either the enucleation step or the nuclear transfer step or both, the use of any suitable reagent that minimizes calcium fluxes in the donor cell immediately following nuclear transfer can be employed. Without being bound by theory, the reduction of calcium fluxes following nuclear transfer provides for more successful nuclear reprogramming. In one aspect, the avoidance of calcium fluxes or oscillation in the host cell allows for the MPF levels to be kept high and thus allow for more successful nuclear remodeling to occur.

In several examples, enucleation and/or nuclear transfer is performed in calcium ($Ca^{2+}$)-free media. In additional examples, enucleation is performed in magnesium ($Mg^{2+}$) free media and calcium-free ions. For example, calcium-free phosphate buffered saline can be utilized. This media is substantially free of calcium ions. In one embodiment, a calcium free medium contains less than about $10^{-6}$ M calcium cations ($Ca^{2+}$), such a media that contains less that as $10^{-7}$ M calcium cations, $10^{-8}$ M calcium cations, $10^{-9}$ M calcium cations, or is substantially free of calcium cations. Similarly, a magnesium-free medium contains less than about $10^{-6}$ M magnesium cations ($Mg^{2+}$), such a media that contains less than about $10^{-7}$ M magnesium cations, $10^{-8}$ M magnesium cations, $10^{-9}$ M magnesium cations, or is substantially free of magnesium cations. The selection of the appropriate media or other reagents that will, for example, chelate extracellular calcium and/or magnesium, such as ethylene glycol tetraacetic acid (EGTA) or ethylenediamine tetraacetic acid (EDTA), do not have added calcium and/or magnesium ions, or otherwise reduce the calcium fluxes during these manipulations are known in the art. Exemplary media are described in the Examples below. These media and reagents are commercially available, and suitable media can be routinely produced in the laboratory.

The amount of time required after introduction of the donor nucleus to the recipient cell for a premature condensed chromosome and spindle to form can vary from cell type to cell type and/or from species to species. In order to allow sufficient time for the premature condensed chromosome and spindle to form, the cell can require culturing for from about 0.5 hours to about 10 hours, from about 1 hour to about 8 hours, from about 1.25 hours to about 6 hours, from about 1.5 hours to about 4 hours, from about 1.75 hours to about 3 hours, or about 2 hours after introduction of the donor nucleus to the recipient or host cell.

Accordingly, methods are provided for producing a human pluripotent stem cell comprising the steps of: (a) enucleating a human oocyte by using a non-UV-based spindle imaging system such that a sufficient amount of the nucleus is removed such that parthenogenesis cannot occur; and (b) introducing the nucleus of a human somatic cell into the enucleated cell, wherein the enucleation and insertion steps occur in the presence of a protein phosphatase inhibitor such as caffeine or MG-132, and wherein the resulting SCNT embryo is activated using an electroporation pulse.

Following introduction of the donor somatic cell nucleus into the enucleated recipient cell, the cell is cultured in vitro. Methods of culturing human blastocyts or pluripotent stem cells are well-known in the art. Any cell culture media that can support the growth and differentiation of human embryonic stem cells can be used. In some embodiments, the pluripotent stem cells are cultured on a feeder layer, such as of murine or human embryonic fibroblasts. However, the feeder layer can include any cell that supports the growth of ESCs. This approach makes for a completely autologous culturing system, thereby eliminating the risk of cross-species contamination. For therapeutic use, the culturing methods can be xeno-free (no xenogeneic cells or components) and can also avoid use of serum (such as fetal bovine serum, FBS) in the culture media.

Human pluripotent cells can be isolated and subsequently cultured in "ES medium," which supports the growth of embryonic stem cells. For example, ES medium comprises 80% Dulbecco's modified Eagle's medium (DMEM; no pyruvate, high glucose formulation, Gibco BRL), with 20% fetal bovine serum (FBS; Hyclone), 0.1 mM B mercaptoethanol (Sigma), 1% non-essential amino acid stock (Gibco BRL).

In one example, an oocyte is enucleated using the methods disclosed above, and a somatic cell nucleus is inserted into the enucleated oocyte, as described herein. The resultant cell is then cultured in medium, such as but not limited to protein free HECM-9 medium and cultured at 37° C. in about 5-6% $CO_2$ until use. These cultures can be maintained under paraffin oil. Once the SCNT embryo reaches about the 2 cell stage or beyond, such as the 4, 8 or 16 cell stage, the cells can be transferred for further culture. In one embodiment, these SCNT embryos are cultured to the blastocyst stage in a culture medium, such as, but not limited to, HECM-9 medium.

In some embodiments, the *zonae pellucidae* of selected expanded blastocysts are removed by brief exposure (45-60 seconds) to 0.5% pronase in TH3 medium. In some embodiments an ICM can be isolated from trophectoderm cells by immunosurgery, where zona-free blastocysts are exposed to rabbit anti-rhesus spleen serum for about 30 minutes at about 37° C. After extensive washing (such as using TH3 medium), embryos are incubated in guinea pig complement reconstituted with HECM-9 (1:2, v/v) for about an additional 30 minutes at about 37° C. Partially lysed trophectodermal cells are mechanically dispersed by gentle pipetting, such as with a small bore pipette (for example, about a 125 µl in inner diameter; Stripper pipette, Midatlantic Diagnostics Inc., Marlton, N.J.) followed by the rinsing of ICMs three times, such as with TH3 medium. Isolated ICMs are plated onto a solid substrate, such as onto Nunc 4-well dishes containing mitotically-inactivated feeder layers consisting of mouse embryonic fibroblasts (mEFs) and cultured, such as in DMEM/F12 medium (Invitrogen) with glucose and without sodium pyruvate supplemented with 1% nonessential amino acids (Invitrogen), 2 mM L-glutamine (Invitrogen), 0.1 mM β-mercaptoethanol and 15% FBS and maintained at about 37° C., about 3% $CO_2$, about 5% $O_2$ and about 92% $N_2$ conditions. Alternatively, whole, intact blastocysts can be directly plated onto mEFs for ESC isolation.

After about 1 to about 7 days, cells, such as blastocysts or ICMs that attached to the feeder layer and initiated outgrowth can be dissociated into small cell clumps, such as manual dissociation with a microscalpel, and re-plated onto a new substrate, such as new embryonic fibroblasts (mEFs). After the first passage, colonies with embryonic stem cell (ESC) like morphology are selected for further propagation, characterization and low temperature storage. Generally, ESC morphology is compact colonies having a high nucleus to cytoplasm ratio, prominent nucleoli, sharp edges and flat colonies. In some examples, the medium is changed daily and ESC colonies are split about every 5-7 days manually or by disaggregation in collagenase IV, (for example, about 1 mg/ml, at about 37° C. for about 2-3 minutes; Invitrogen) and replating collected cells onto dishes with fresh feeder layers. Cultures are maintained at about 37° C., about 3% $CO_2$, about 5% $O_2$ and about 92% $N_2$. In another alternative, serum-free media is used.

PSCs can then be isolated, and PSCs can be maintained in vitro using standard procedures. In one example, human PSCs are isolated on a confluent layer of fibroblast in the presence of ESC medium. In one example, to produce a feeder layer, xenogeneic embryonic fibroblasts are obtained from 14-16 day old fetuses from outbred mice (such as CF1, available from SASCO), but other strains can be used as an alternative. Alternatively, human fibroblasts obtained from adult skin or cells obtained from TSC-derived fibroblasts can be employed. In another embodiment, tissue culture dishes treated with about 0.1% gelatin (type I; Sigma) can be utilized. Unlike mouse PSC cells, human PSC (hPSC) cells do not express the stage-specific embryonic antigen SSEA-1, but express SSEA-4, which is another glycolipid cell surface antigen recognized by a specific monoclonal antibody (see, for example, Amit et al, *Devel Biol* 227, 271-278, (2000); incorporated by reference herein).

ICM-dissociated cells can be plated on feeder layers in fresh medium, and observed for colony formation. Colonies demonstrating ESC morphology are individually selected, and split again as described above. Resulting PSCs are then routinely split by mechanical methods every six days as the cultures become dense. Early passage cells are also frozen and stored in liquid nitrogen.

PSCs as well as transplantable cells can be produced and can be karyotyped with, for example, a standard G-banding technique (such as by the Cytogenetics Laboratory of the University of Wisconsin State Hygiene Laboratory, which provides routine karyotyping services) and compared to published human karyotypes.

In other embodiments, immunosurgical isolation of the ICM is not utilized. Thus, the blastocysts are cultured directly, without the use of any immunosurgical techniques. Culture conditions described above can also be used for the culture of PSCs from blastocysts. Conditions for culturing human totipotent stem cells obtained by conventional protocols from fertilized oocytes to the blastocyst have been described (see Bongso et al, *Hum Reprod* 4, 706-713, (1989); incorporated by reference herein). In some embodiments, co-culturing of human SCNT embryos with human oviductal cells results in the production of high quality blastocysts. Human ICM from blastocysts grown in cellular coculture or in media that eliminates the feeder cell layer requirement allows isolation of human PSCs with the same procedures described above.

Uses of Human Pluripotent Stem Cells

Also provided herein are therapeutic compositions comprised of transplantable cells which have been derived (produced) from PSCs in a formulation suitable for administration to a human subject. In one example, that human subject is the source of the somatic nucleus. The therapeutic compositions include multipotent cells, lineage-specific stem cells, as well as partly or fully differentiated cells derived from the PSCs provided herein.

The cells can be matched at one or more loci of the major histocompatibility complex (MHC). In one example, there is a complete match at every MHC loci. In another example, the PSCs are made by the transfer of a nucleus from a somatic cell of the subject into an enucleated oocyte from a second individual as described herein. A therapeutically effective amount of pluripotent or multipotent cells can then be used to treat the subject.

Methods for treating disease are provided that comprise transplanting PSCs or cells derived from PSCs in a human subject afflicted with a disease characterized by damaged or degenerative somatic cells. Such cells can be multipotent cells or any other type of transplantable cells.

The human PSCs described herein are useful for the generation of cells of desired cell types. In some embodiments, the PSCs are used to derive mesenchymal, neural, and/or hematopoietic stem cells. In other embodiments, the PSCs are used to generate cells, including but not limited to, pancreatic, liver, bone, epithelial, endothelial, tendons, cartilage, and muscle cells, and their progenitor cells. Thus, transplantable cells derived from PSCs can be administered to an individual in need of one or more cell types to treat a disease, disorder, or condition. Examples of diseases, disorders, or conditions that can be treated or prevented include neurological, endocrine, structural, skeletal, vascular, urinary, digestive, integumentary, blood, immune, auto-immune, inflammatory, kidney, bladder, cardiovascular, cancer, circulatory, hematopoietic, metabolic, reproductive and muscular diseases, disorders and conditions. In some embodiments, a hematopoietic stem cell derived from human PSCs is used to treat cancer. In some embodiments, these cells are used for reconstructive applications, such as for repairing or replacing tissues or organs.

The PSCs described herein can be used to generate multipotent stem cells or transplantable cells. In one example, the transplantable cells are mesenchymal stem cells. Mesenchymal stem cells give rise to a very large number of distinct tissues (Caplan, *J Orth Res* 641-650 (1991); incorporated by reference herein). Mesenchymal stem cells capable of differentiating into bone, muscles, tendons, adipose tissue, stromal cells and cartilage have also been isolated from marrow. U.S. Pat. No. 5,226,914 (incorporated by reference herein) describes an exemplary method of isolating mesenchymal stem cells from bone marrow. In other examples, epithelial progenitor cells or keratinocytes can be generated for use in treating conditions of the skin and the lining of the gut (Rheinwald, *Meth Cell Bio* 21A, 229 (1980); incorporated by reference herein). The cells can also be used to produce liver precursor cells (see PCT Publication No. WO 94/08598; incorporated by reference herein) or kidney precursor cells (see Karp et al, *Dev Biol* 91, 5286-5290 (1994); incorporated by reference herein). The cells can also be used to produce inner ear precursor cells (see Li et al, *Trends Mol Med* 10, 309 (2004); incorporated by reference herein).

The transplantable cells can also be neuronal cells. The volume of a cell suspension, such as a neuronal cell suspension, administered to a subject will vary depending on the site of implantation, treatment goal and amount of cells in solution. Typically the amount of cells administered to a subject will be a therapeutically effective amount. For example, where the treatment is for Parkinson's disease, transplantation of a therapeutically effective amount of cells will typically produce a reduction in the amount and/or severity of the symptoms associated with that disorder, e.g., rigidity, akinesia and gait disorder. In one example, a severe Parkinson's patient needs at least about 100,000 surviving dopamine cells per grafted site to have a substantial beneficial effect from the transplantation. As cell survival is low in brain tissue transplantation in general (5-10%) at least 1 million cells are administered, such as from about 1 million to about 4 million dopaminergic neurons are transplanted. In one embodiment, the cells are administered to the subject's brain. The cells can be implanted within the parenchyma of the brain, in the space containing cerebrospinal fluids, such as the sub-arachnoid space or ventricles, or extaneurally. Thus, in one example, the cells are transplanted to regions of the subject which are not within the central nervous system or peripheral nervous system, such as the celiac ganglion or sciatic nerve. In another embodiment, the cells are transplanted into the central nervous system, which includes all structures within the dura mater. Those of skill in the art are familiar with techniques for administering cells to the brain of a subject.

Human PSCs produced using the methods disclosed herein are capable of contributing to the germ line. Thus, somatic cells from a subject of interest can be used to produce ES cells which subsequently can be differentiated into oocytes or sperm. These oocytes or sperm can then be used for fertilization, allowing an infertile subject to produce children that are genetically related to the subject. In addition, ES cell-derived eggs are of use in research. For example, these eggs can in turn be used to make SCNT-derived ES cells. This availability of these oocytes can reduce the use of donated human eggs for research.

Cells produced by the methods disclosed herein, such as PSC are also of use for testing agents of interest, such as to determine if an agent affects differentiation or cell proliferation. For example, PSCs are contacted with the agent, and the ability of the cells to differentiate or proliferate is assessed in the presence and the absence of the agent. Thus, cells produced by the methods disclosed herein can also be used in to screen pharmaceutical agents to select for agents that affect specific human cell types, such as agents that affect neuronal cells. Cells produced by the methods disclosed herein can also be used to screen test compounds to select those that affect differentiation. A test compound can be any compound of interest, including chemical compounds, small molecules, polypeptides or other biological agents (for example antibodies or cytokines). In several examples, a panel of potential agents is screened, such as a panel of cytokines or growth factors is screened.

EXAMPLES

The following examples are illustrative of disclosed methods. In light of this disclosure, those of skill in the art will recognize that variations of these examples and other examples of the disclosed method would be possible without undue experimentation.

Example 1

Overview

Reprogramming of somatic cells to pluripotent embryonic stem cells (ESCs) by somatic cell nuclear transfer (SCNT) was long hoped to generate patient-matched nuclear transfer derived-ESC (NT-ESCs) to study disease mechanisms and to develop therapies. Until now, all attempts to produce human NT-ESCs have failed, largely due to early embryonic arrest of SCNT embryos. Disclosed herein is the identification of premature exit from meiosis in human oocytes and suboptimal activation as key factors responsible for embryonic arrest. Disclosed herein are optimized SCNT methods designed to overcome these defects and that allow, for the first time, derivation of human NT-ESCs. NT-ESCs displayed normal diploid karyotypes and inherited their nuclear genome exclusively from parental somatic cells. Gene expression and differentiation profiles in human NT-ESCs were similar to genuine embryo derived ESCs suggesting efficient conversion of somatic cells to pluripotency.

The main roadblock to producing human NT-ESCs is the embryonic arrest of human SCNT embryos prior to the development of stable NT-ESCs. Typically, SCNT embryos fail to progress beyond the 8-cell stage, presumably due to inability to activate critical embryonic genes from the somatic nucleus (Egli D et al, Nature Comm 2, 488 (2011) and Noggle S et al, Nature 478, 70-75 (2011); both of which are incorporated by reference herein). In those few cases describing SCNT embryos reaching the blastocyst stage, such embryos failed to produce stable ESCs (Fan Y et al, Stem Cells Dev 20, 1951-1959 (2011) and French A J et al, Stem Cells 26, 485-493 (2008).

While the underlying cause of this early developmental arrest remains unclear, these studies mechanically applied SCNT protocols developed for other species for human oocytes. It has been previously demonstrated that, to be effective, SCNT procedures must be adapted to primates. Reprogramming of rhesus macaque adult skin fibroblasts into NT-ESCs was achieved (Byrne J A et al, Nature 450, 497-502 (2007) and Sparman M et al, Stem Cells 27, 1255-1264 (2009); both of which are incorporated by reference herein).

Removal of a human oocyte's nuclear genetic material (chromosomes) negatively impacts the ability of the cytoplast to induce reprogramming (Noggle et al, 2011 supra). However, when a somatic cell nucleus was transplanted into an intact oocyte with a full set of chromosomes, the resulting polyploid embryos were able to overcome the developmental block and produce ESCs.

It was also observed that the meiotic arrest in human MII oocytes is unstable and can be perturbed by mechanical manipulations (Tachibana M et al, Nature 493, 627-631 (2013); incorporated by reference herein). Additionally, retention of meiosis specific activity in a cytoplast is critical for nuclear remodeling after the transplantation of an interphase somatic cell nucleus (Mitalipov S M et al, Hum Reprod 22, 2232-2242 (2007); incorporated by reference herein). Nuclear remodeling is positively correlated with further development of SCNT embryos after activation. Therefore, modifications in oocyte enucleation and donor cell introduction that retain meiosis factors in human cytoplasts were systematically evaluated.

It is disclosed herein that routine artificial activation treatments are insufficient to support subsequent human SCNT development and that alterations in SCNT significantly improve blastocyst formation by human SCNT embryos. Several human NT-ESC lines were derived from these embryos. These NT-ESC lines were validated by their nuclear DNA being identical to the nuclear donor somatic cells but with their mitochondrial DNA being identical to that of the recipient oocytes. Finally, extensive pluripotency assays were performed on the derived human NT-ESCs and their complete reprogramming was verified.

Example 2

SCNT Protocol Optimizations in a Nonhuman Primate Model

Human MII oocytes are subject to premature activation induced by removal and re-introduction of meiotic spindles (Tachibana et al, 2013 supra). A large portion of oocytes subjected to human spindle transfer (ST) underwent spontaneous resumption and exited from meiosis before fertilization, suggesting that mechanical manipulations cause a decline in meiotic kinase activities. In addition, nuclear envelope breakdown (NEBD) and premature chromosome condensation (PCC), which occur immediately after introduction of an interphase somatic cell nucleus, for improved SCNT development (Mitalipov et al, 2007 supra).

It was reasoned that the developmental arrest of human SCNT embryos and their failure to produce NT-ESCs could be due to lack of or incomplete NEBD and PCC. Therefore, new nuclear transfer protocols that minimize premature activation were necessary.

Cell fusion induced by electroporation was shown to deliver a precocious activation stimulus to the cytoplast which resulted in exit from meiosis (Tachibana M et al, Nature 461, 367-372 (2009). An earlier-described spindle transfer protocol replaced electrofusion with hemagglutinating virus of Japan (HVJ-E). Use of HVJ-E was critical to maintain cytoplasts in meiosis (Tachibana et al, 2009 supra). This HVJ-E-based cell fusion was then used to develop rhesus macaque SCNT embryos.

Figure 1B:
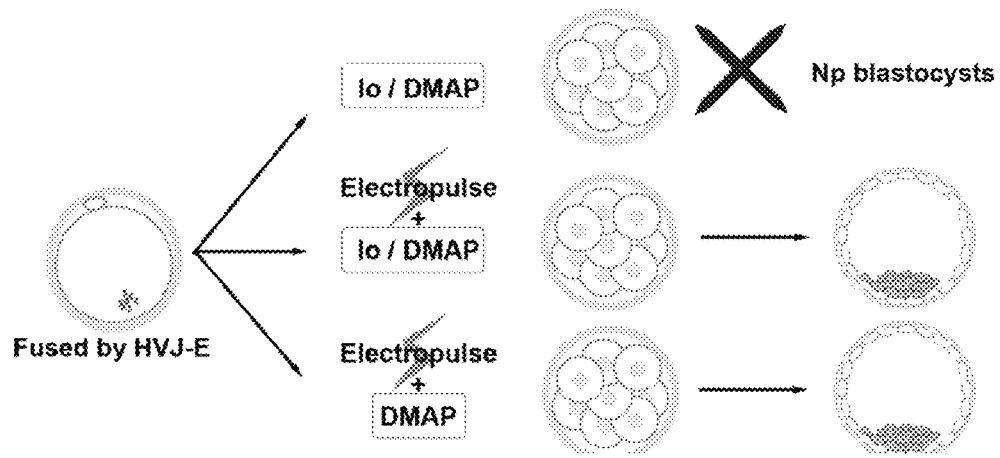
Figure 1C:
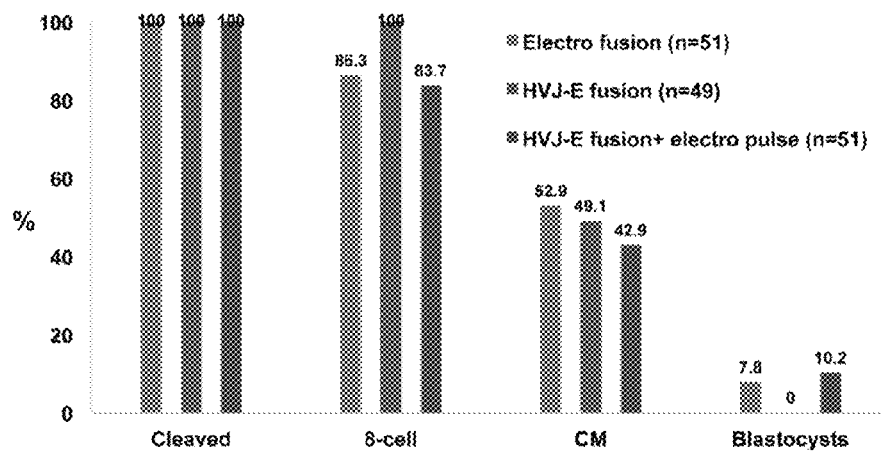

Fusion rates were 100% using either electrofusion or HVJ-E suggesting that introduction of donor cell nuclei can be efficiently used for both approaches. Interphase somatic nuclei introduced by electrofusion maintained intact nuclear membrane as detected by Lamin B staining with no detectable premature chromosome condensation. (FIG. 1A). In contrast, nuclei of HVJ-E fused cells underwent rapid NEBD followed by PCC within 30 minutes after fusion (FIG. 1A). Efficient NEBD and PCC were associated with formation of spindle-like structures easily detectable by non-invasive examination using a polarized microscope. These results are in agreement with premature activation and decline in the activity of meiotic factors caused by electroporation. In an unexpected result, however, SCNT embryos generated by HVJ-E fusion failed to progress beyond the compact morula stage while a small portion of control SCNT embryos produced by electrofusion reached the blastocyst stage (FIGS. 1B and C).

Figure 8:
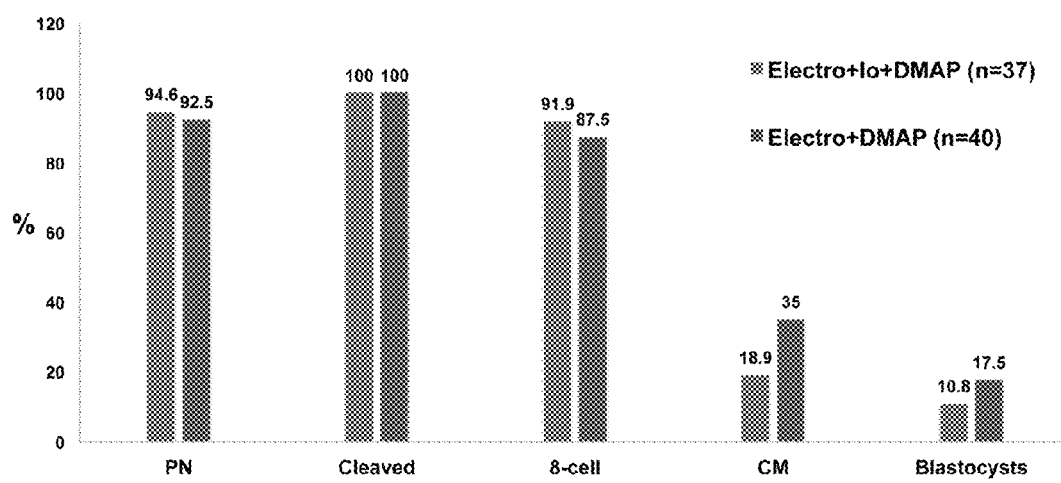
FIG. 8 is a bar graph depicting the In vitro development of monkey SCNT embryos with or without electro pulse, and various concentrations of TSA as indicated.

These results suggested that electrofusion would be beneficial for SCNT reprogramming and can act as an additional activation stimulus. As a result, HVJ-E fused SCNT embryos were exposed to the electroporation prior to standard Ionomycin/DMAP activation treatment. Indeed, this treatment produced SCNT embryos capable of reaching the blastocyst stage at a rate similar to controls (FIGS. 1B and C). Unexpectedly, the SCNT blastocyst formation rate was unaffected even when exposure to Ionomycin was omitted and SCNT embryos were activated with electroporation followed by DMAP treatment (FIG. 8). Together these data indicate that while electroporation stimulus is not required for cell fusion, it is important for proper cytoplast activation following SCNT.

Histone deacetylase inhibitors, such as trichostatin A (Chan et al, J Pedodontics 7, 18-35 (1982); incorporated by reference herein), have been associated with improved SCNT reprogramming in several mammalian species (Ding X et al, Theriogenology 70, 622-630 (2008); Kishigami S et al, Biochem Biophys Res Comm 340 183-189 (2006); and Li J et al, Theriogenology 70, 800-808 (2008); all of which are incorporated by reference herein). Enhanced development of monkey SCNT embryos to blastocysts was observed when the embryos are treated with 37.5 nM TSA (from 4% to 18%) (Sparman M et al, Stem Cells 27, 1255-1264 (2010); incorporated by reference herein).

However, the quality of such blastocysts and their potential to give rise to stable ESCs remained unknown until this current disclosure. A total of 16 monkey SCNT blastocysts produced with TSA treatment were plated on mitotically inactivated mouse embryonic fibroblast (mEF) feeders. None of these blastocysts produced NT-ESC lines (Table 1). Lower TSA concentrations as well as shorter exposure times to TSA had no effect on monkey SCNT blastocyst development and ESC isolation. Reducing the TSA concentration to 10 nM or shortening the TSA exposure time from 24 h to 12 h did not affect blastocyst rates (Table 1). Notably, only SCNT blastocysts produced with 10 nM TSA supported derivation of stable monkey NT-ESC lines (Table 2).

TABLE 1

Monkey SCNT embryo development after treatment with trichostatin A (TSA)

| TSA concentration and time | rep | N | fused (%) | PN (%) | 8-cell (%) | CM (%) | Blastocysts (%) |
|---|---|---|---|---|---|---|---|
| 37.5 nM for 24 h | 39 | 511 | 503 (98.4) | 498 (99.0) | 418 (90.3) | 107 (23.1) | 85 (18.4) |
| 10 nM for 24 h | 10 | 108 | 104 (95.4) | 104 (100) | 100 (97.1) | 33 (32.0) | 25 (24.3) |
| 10 nM for 12 h | 37 | 571 | 567 (99.3) | 535 (94.4) | 494 (93.7) | 147 (27.9) | 99 (18.8) |
| 5 nM for 12 h | 16 | 212 | 210 (99.1) | 207 (98.6) | 192 (92.8) | 58 (26.0) | 30 (14.5) |

TABLE 2

Monkey NT-ESC isolation after treatment with TSA

| TSA Concentration | TSA duration | # Plated blastocyst | # NT-ESCs (%) |
|---|---|---|---|
| 37.5 nM | 24 h | 16 | 0 |
| 10 nM | 24 h | 4 | 0 |
|  | 12 h | 23 | 3 (13%) |
| 5 nM | 12 h | 7 | 0 |

Example 3

Producing Human SCNT Blastocysts and NT-ESC Lines

Figure 2A:
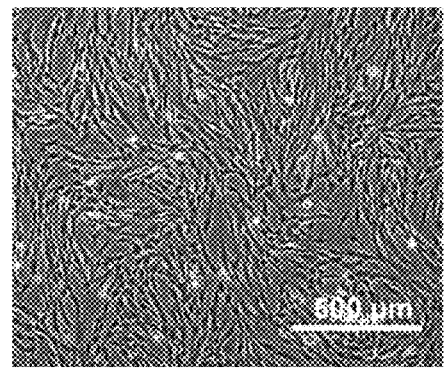
FIGS. 2A, 2B, 2C, 2D, 2E, and 2F collectively show that SCNT blastocyst development is affected by premature cytoplast activation.

This example describes the production of human SCNT blastocysts and NT-ESC lines. Human MII oocytes were collected from healthy volunteers (age 23-33) and subjected to the SCNT protocol that produced best results in a non-human primate model. Oocytes were retrieved following standard ovarian stimulation protocols and transvaginal follicular aspirations. Human dermal fibroblasts of fetal origin (HDF-f) synchronized in G0/G1 cell cycle phase were used as nuclear donors (FIG. 2A). Removal of spindles and HVJ-E-assisted donor cell fusion was carried out within 60 min after oocyte retrievals.

Figure 3A:
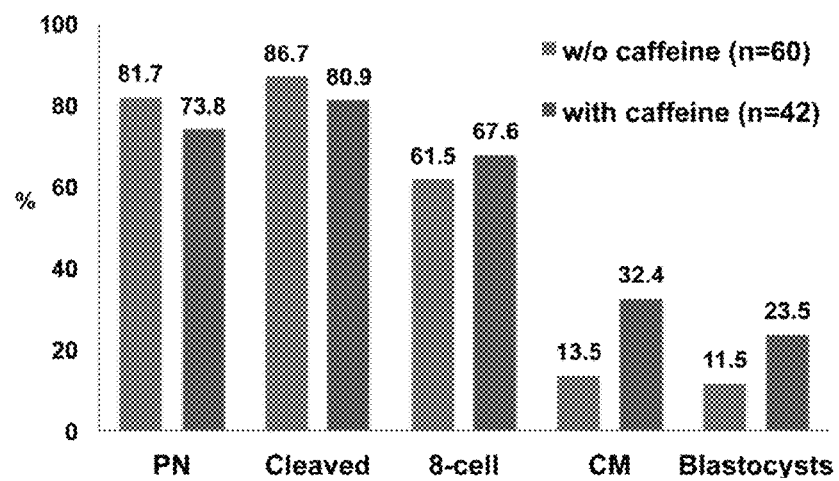
FIGS. 3A and 3B collectively show the development of human SCNT embryos and NT-ESC derivation after caffeine treatment

Most oocytes (95.2%: 60/63) survived MII spindle removal conducted under polarized microscopy (Oosight™) (Byrne et al, (2007) supra; Sparman et al, (2009) supra) and nuclei from donor fibroblasts were introduced using the HVJ-E fusion described above. Efficiency of fusion was 100%. Immediately after confirmation of fusion, oocytes were activated with electroporation/DMAP (4 h) and exposed to 10 nM TSA for 12 hours. The majority of human SCNT embryos (81.7%, 49/60), formed one or two pronuclei at the time of removal of TSA. A slightly higher portion of embryos cleaved (86.7% 52/60) suggesting that some SCNT embryos did not exhibit visible pronuclei at the time of examination (FIG. 3A). The majority of cleaved embryos developed to the 8-cell stage (61.5%, 32/52), but fewer still progressed to the compact molura (CM) (13.5%, 7/52) and blastocyst (11.5%, 6/52) stages (FIG. 3A).

Activation of embryonic genes and transcription from the transplanted somatic cell nucleus are required for development of SCNT embryos beyond the 8-cell stage (Egli et al, (2011) supra; Noggle et al, (2011) supra). Therefore, these results suggest that these methods successfully reprogram of human somatic cells to the embryonic state.

Figure 2B:
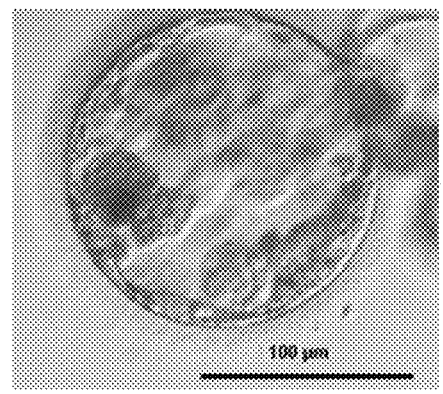

However, human SCNT blastocysts exhibited poorly organized trophectoderm and small or undetectable inner cell masses (ICMs). In addition, large blastomere-like cells were excluded into a civility of SCNT blastocysts (FIG. 2B). Six of these SCNT blastocysts were plated onto a feeder layer to examine their ability to support ESC derivation. Four of the blastocysts attached to the mEFs feeder cells, but only one displayed an outgrowth that was further passaged. The further passaging failed to produce stable ESC-like cells (FIG. 3B).

Figure 2C:
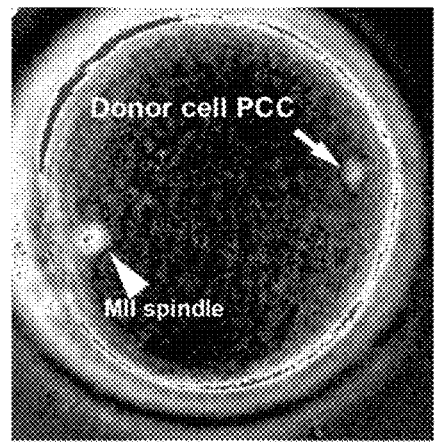

Clearly, further optimization of human SCNT protocols was needed to produce viable NT-ESCs. Somatic nuclei were introduced into intact human MII oocytes and their birefringence properties assessed using a polarized microscope. All somatic nuclei introduced into MII oocytes efficiently formed spindle-like structures that were visible within 30 min after fusion (17/17) (FIG. 2C). However, spindle formation was not observed when the somatic cell nuclei were fused with enucleated human oocytes (0/3). These observations are consistent with other recent observations that human MII oocytes undergo premature activation caused by enucleation (Tachibana et al, 2013 supra).

Figure 2D:
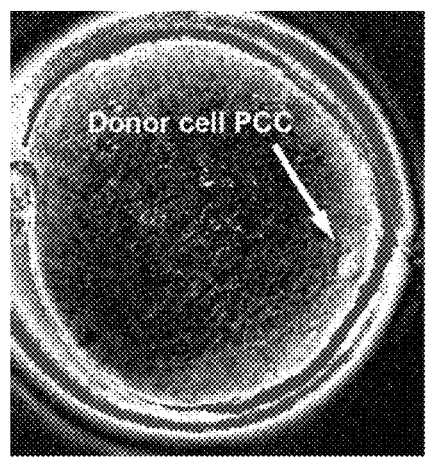
Figure 2E:
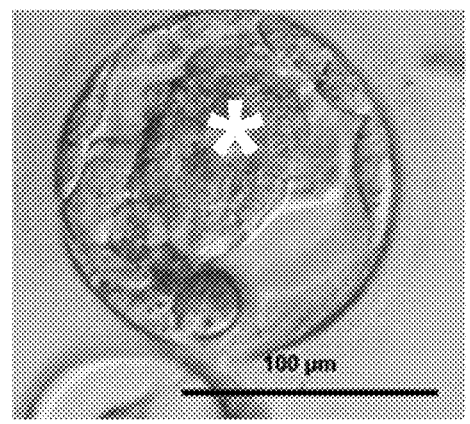

Exposure of monkey oocytes to caffeine, a protein phosphatase inhibitor, was effective in protecting the cytoplast from premature activation and improved the development of SCNT embryos (Mitalipov et al, 2007 supra). Therefore, human oocytes were maintained in 1.25 mM caffeine during enucleation and somatic cell fusion. As expected, somatic cell nuclei introduced into oocyte cytoplasts under these conditions efficiently formed spindle-like structures detectable under birefringence microscope (83.3%, 10/12) (FIG. 2D). More importantly, blastocyst development of caffeine treated embryos was also notably enhanced (23.5%) compared to standard SCNT group (FIG. 3A). Human SCNT blastocysts in this group contained visible, prominent ICMs similar to that observed for IVF embryos (FIG. 2E).

Figure 2F:
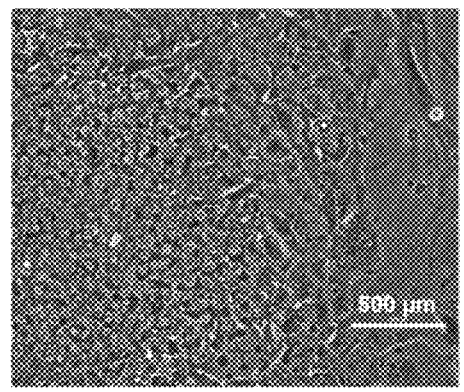
Figure 3B:
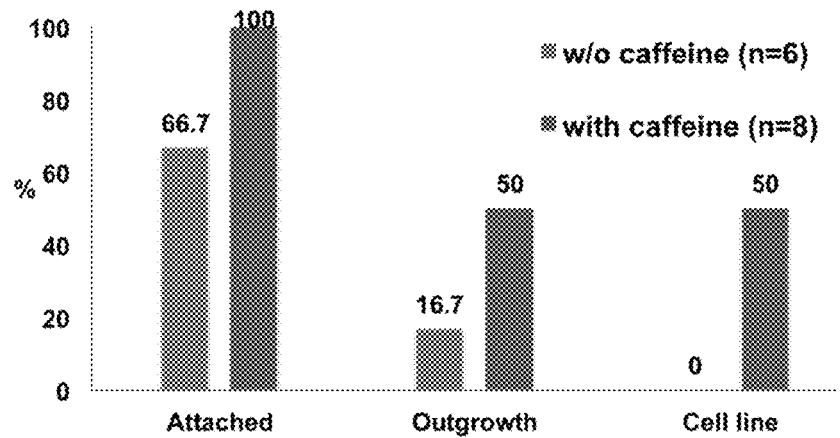

Remarkably, when eight SCNT blastocysts produced with caffeine were utilized for ESCs isolation, all attached to mEFs and 4 formed an ICM outgrowth (FIG. 3B). All four ICM outgrowths gave rise to ESC-like colonies upon manual splitting onto fresh mEF plates (FIG. 2F). Subsequent passaging resulted in efficient propagation of stable ESC colonies with typical morphology and growth characteristics. This surprisingly high ESC derivation rate was similar to that reported in our previous study with human IVF-derived blastocysts (50%) and was even higher than in manipulated ST embryos (38%) (FIG. 3B) (Tachibana et al, 2013 supra).

Collectively, our findings indicate that protocols perfected in a NHP model support blastocyst development for human SCNT embryos. However, poor quality of human SCNT blastocysts precluded ESC isolation. Incorporation of caffeine during enucleation and fusion, to counter spontaneous activation of human MII oocytes, improved blastocyst development and supported derivation of ESCs.

Example 4

Reproducibility of Human SCNT Results

Figure 9A:
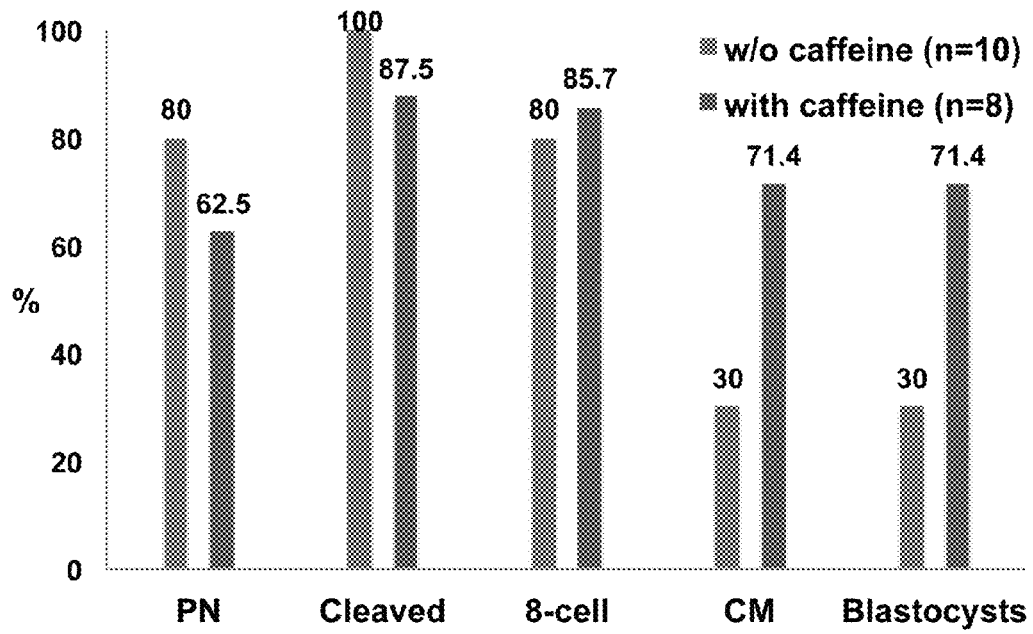
FIG. 9A is a bar graph depicting the in vitro development of SCNT embryos from a human donor to the blastocyst stage.
Figure 9B:
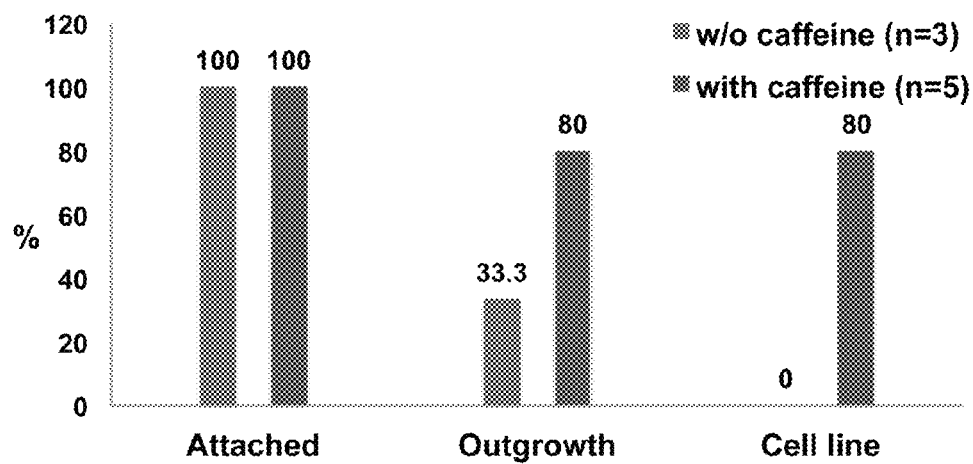
FIG. 9B is a bar graph depicting the in vitro development of pluripotent stem cell lines from SCNT embryos from the same human donor as in FIG. 9A.

All 4 human NT-ESC lines produced by the disclosed method were derived from oocytes retrieved from one particular egg donor. Eight mature MII oocytes were recovered from this donor after a single stimulation cycle and used for SCNT. Using the disclosed methods, 5 blastocysts were produced (62.5%) that gave rise to 4 NT-ESC lines (80%) (FIG. 9). In addition, all four cell lines were derived using fetal dermal fibroblasts as nuclear donors. In the context of generating patient-specific pluripotent stem cells, the therapeutic potential of SCNT depends on reproducibility of results with various patient-derived somatic cells and different oocyte donors.

Figure 4A:
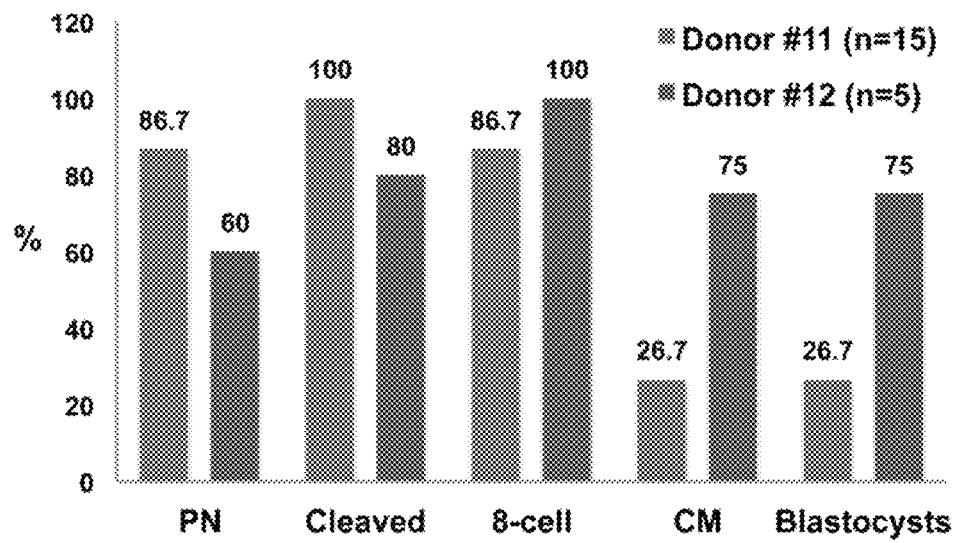
FIGS. 4A and 4B collectively show the results from human SCNT from donor cells derived from a patient with Leigh's disease.
Figure 4B:
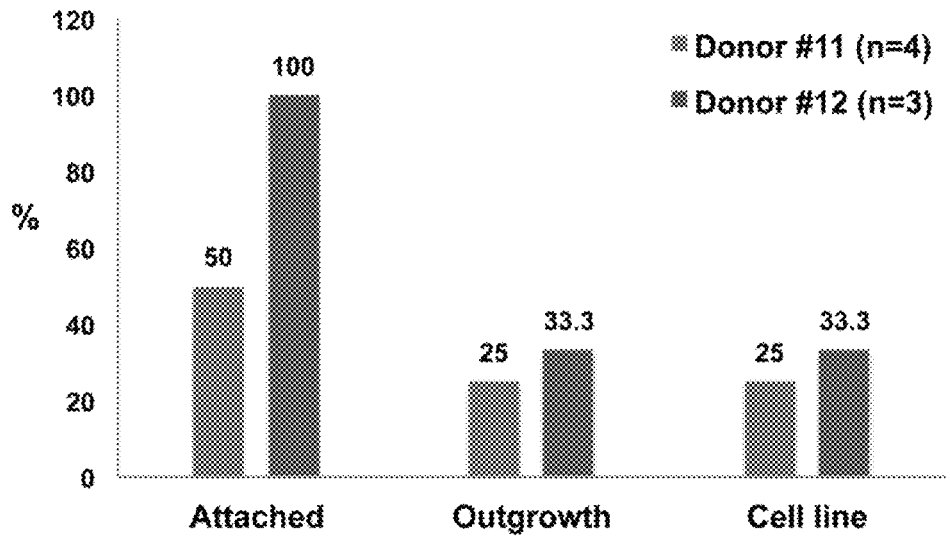

A skin fibroblast culture was obtained from a patient with Leigh syndrome. A total of 15 and 5 MII oocytes were collected from two unrelated egg donors (donors #11 and #12, respectively). The disclosed SCNT methods were then performed using nuclei from the skin fibroblasts. All oocytes survived enucleation and successfully fused with donor cells. Following activation and culture, 4 (27%, 4/15) and 3 (60%, 3/5) blastocysts were produced from the each egg donor, respectively (FIG. 4A). After plating on mEFs and manual passaging, two stable NT-ESC lines were established, one from the each egg cohort (FIG. 4B). Thus, these outcomes confirm the reproducibility and efficacy of the disclosed SCNT protocols with another nuclear donor cells and different cohort of human oocytes.

Example 5

Retrospective Analysis of Factors Affecting the Success of Human SCNT

Although SCNT manipulations and treatments were strictly controlled, the quality and quantity of human oocytes retrieved from different egg donors varied significantly. An excessive number of oocytes retrieved from a cycle is generally associated with poor clinical IVF outcomes (Pellicer A et al, *Hum Reproduction* 4, 536-540 (1989); Santos M A et al, *Reproduction* 139, 23-34 (2010); and van der Gaast M H et al, *Reprod Biomed Online* 13, 476-480 (2006); all of which are incorporated by reference herein.

Figure 5A:
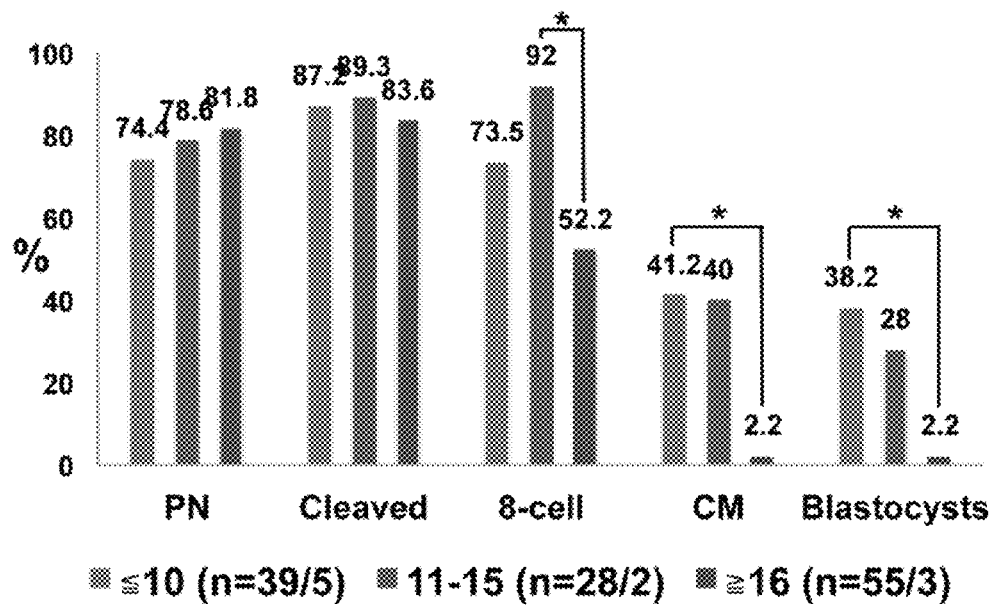
FIGS. 5A, 5B, 5C and 5D collectively depict the effect of ovarian stimulation on human SCNT outcomes.
Figure 5B:
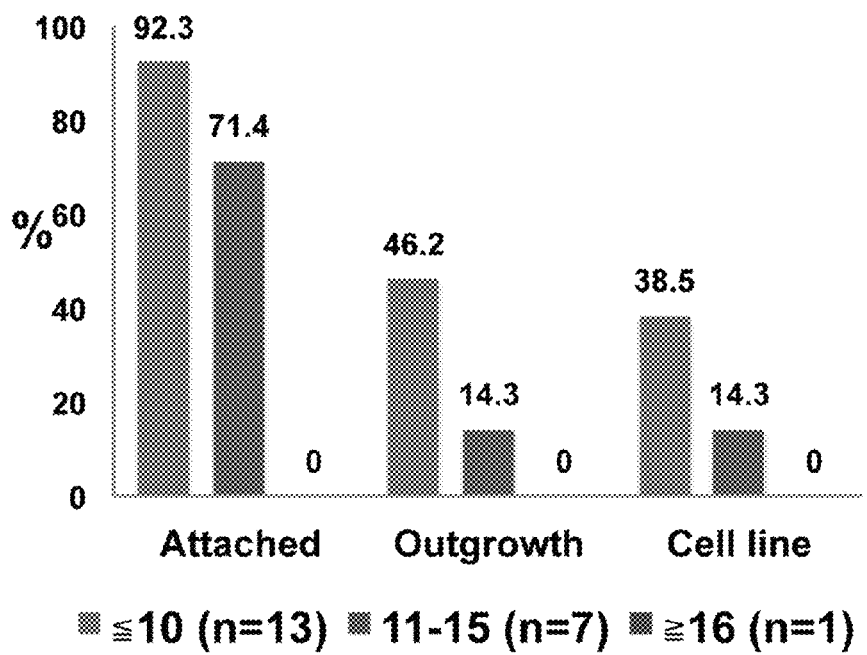
Figure 10:
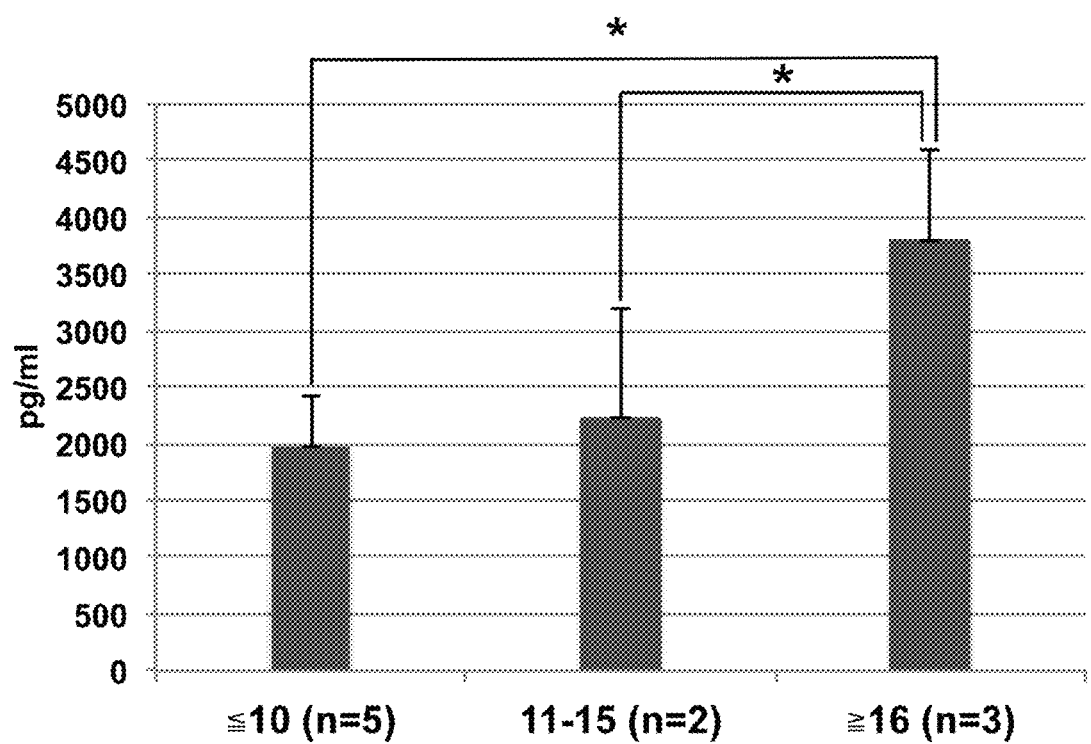
FIG. 10 is a bar graph depicting the correlation between peak estradiol levels and the numbers of MII oocytes produced by human donors.

A retrospective analysis of ovarian stimulation procedures was conducted in order to determine the effect of the number of oocytes retrieved per cycle on human SCNT embryo development and NT-ESC derivation outcomes. Oocyte donation cycles were divided into three groups based on the range of collected mature MII oocytes—10 or fewer oocytes per cycle (5 donors), between 11 to 15 oocytes (2 donors) and more than 16 oocytes per cycle (3 donors). While survival after enucleation, fusion, pronuclear formation and cleavage of SCNT embryos were similar between these groups, more embryos derived from the donors producing ≥16 MII oocytes/cycle arrested after the 8-cell stage than the other two groups (FIG. 5A). In addition, the quality of SCNT blastocysts also negatively correlated with the number of collected oocytes per cycle. While five NT-ESC lines were derived from donors producing ≤10 oocytes/cycle, only one line was produced from donors producing 11-15 oocytes per cycle and no cell line was established from cycles with ≥16 oocytes (FIG. 5B). The peak estradiol (E2) level measured in blood of egg donors prior to hCG priming positively correlated with the subsequent yield of oocytes (FIG. 10). Thus, these observations imply that the higher the number of oocytes collected, the worse the oocyte quality and reprogramming ability in the context of SCNT.

Optimal stimulation protocols giving the best chance of producing oocytes capable of producing NT-ESCs using SCNT were sought. The impact of GnRH agonists and antagonists used to suppress the pituitary function of egg donors were first assessed. Prior to stimulations, the anti-mullerian hormone (AMH) level and antral follicle counts (AFC) were measured for each individual egg donor (Table S3). Donors with higher AMH and AFC profiles are associated with high ovarian reserve and received the GnRH agonist Lupron® (4 cycles) while the remaining donors were provided with the GnRH antagonist (ganirelix, 6 cycles) (Table 3).

TABLE 3

Clinical values for different pituitary suppression regimen groups

| | GnRH antagonist | GnRH agonist | |
|---|---|---|---|
| # Cycles | 6 | 4 | |
| # oocytes | 11.7 ± 5.6 | 20.5 ± 11.9 | NS |
| Age | 29 ± 2.5 | 24.3 ± 1.3 | P < 0.05 |
| AMH (ng/ml) | 2.8 ± 0.5 | 4.2 ± 1.2 | P < 0.05 |
| AFC | 23.1 ± 7.2 | 33.3 ± 5.4 | P < 0.05 |
| FSH dosage (IU) | 958.3 ± 241.7 | 950 ± 253.3 | NS |
| # hMG samples | 8.5 ± 1.6 | 8.8 ± 0.9 | NS |
| Stimulation days | 8.7 ± 1.6 | 9 ± 0.8 | NS |
| Peak E2 | 2568.2 ± 806.1 | 2709 ± 1597.3 | NS |

Figure 5C:
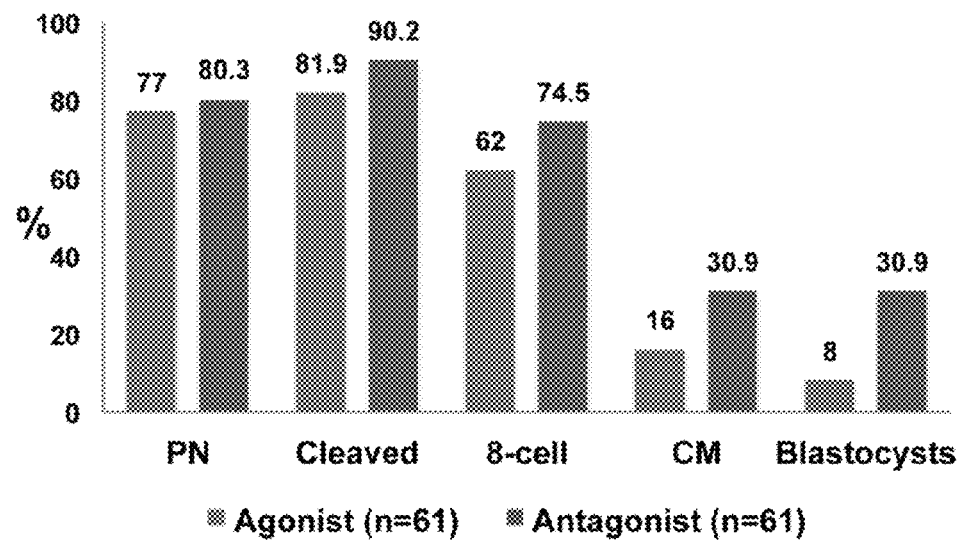
Figure 5D:
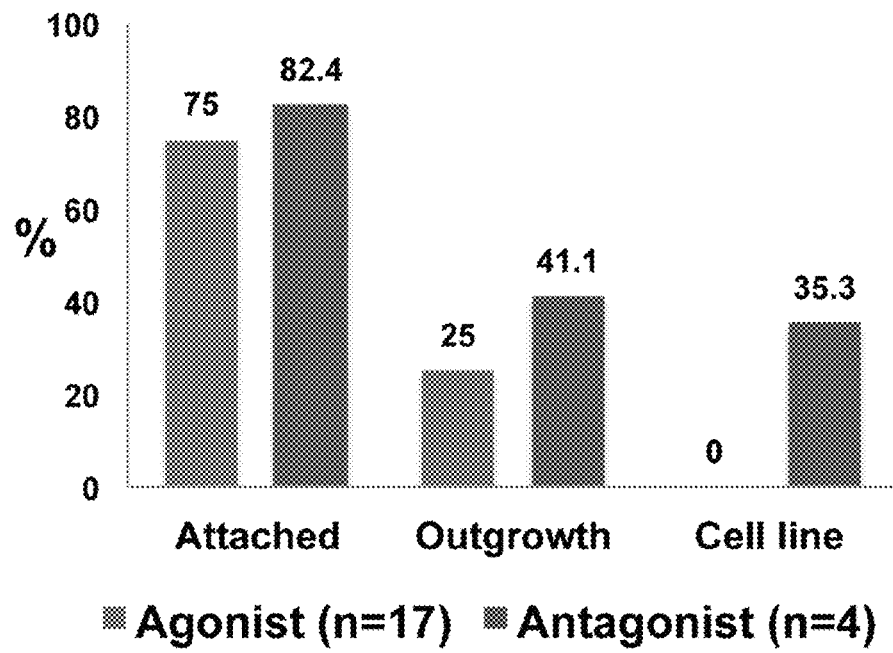

The average number of MII oocytes (mean±SD) collected per cycle was not statistically different between the GnRH antagonist and GnRH agonist treated groups (11.7±5.6 and 20.5±11.9, respectively). However, SCNT embryo development beyond the 8-cell stage was impaired in oocytes produced with GnRH agonist treatment (FIG. 5C). Moreover, all six NT-ESC lines were derived from oocytes collected from donors treated with GnRH antagonist (FIG. 5D). Based on these observations, it is reasonable to conclude that pituitary suppression with GnRH agonists during ovarian stimulations can result in production of oocytes with diminished quality, incompatible with SCNT blastocyst development and ESC isolation.

Figure 11:
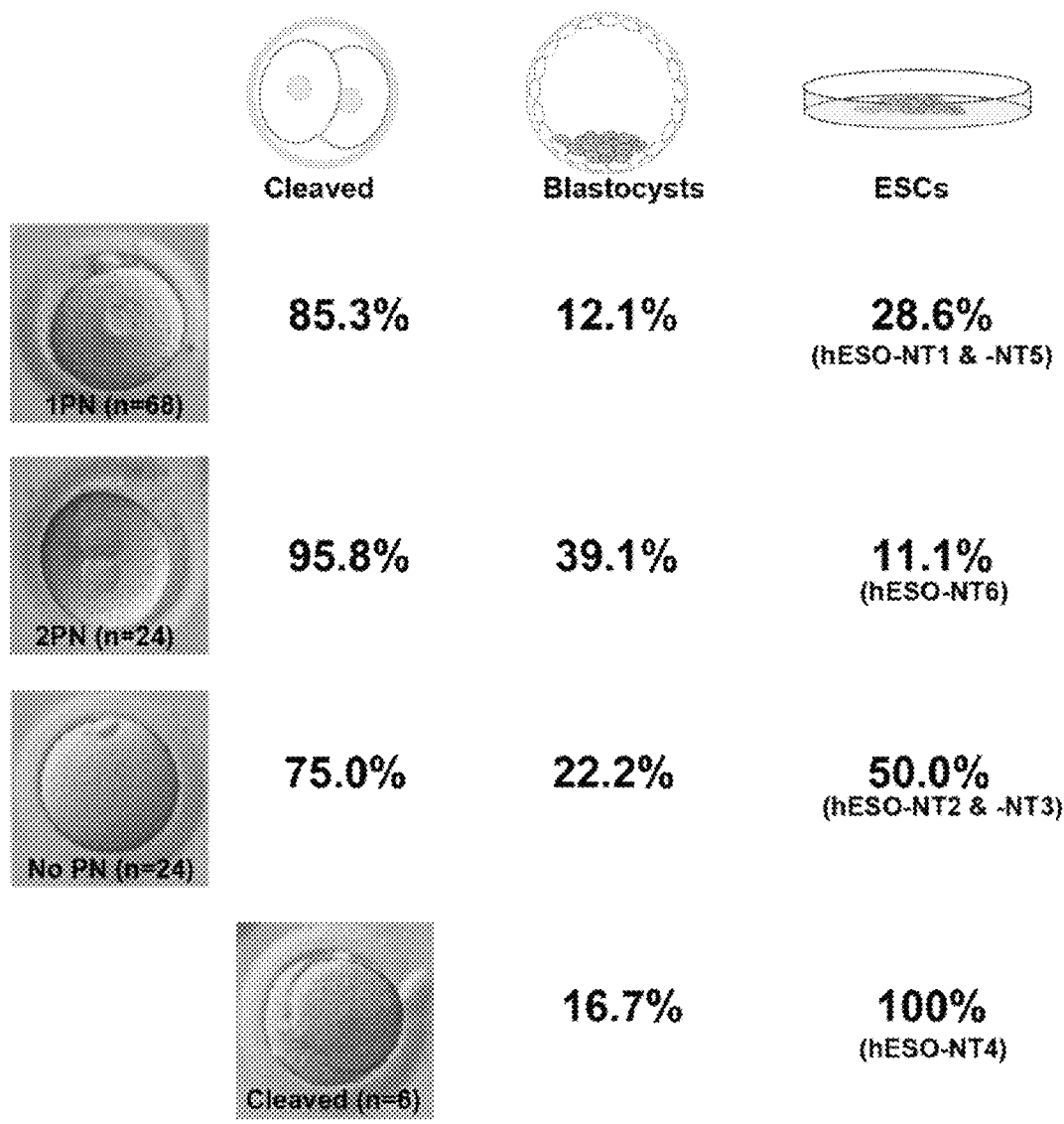
FIG. 11 is a chart with images that illustrates in vitro development and stem cell isolation of different subcategories at pronuclear observation.
Figure 12A:
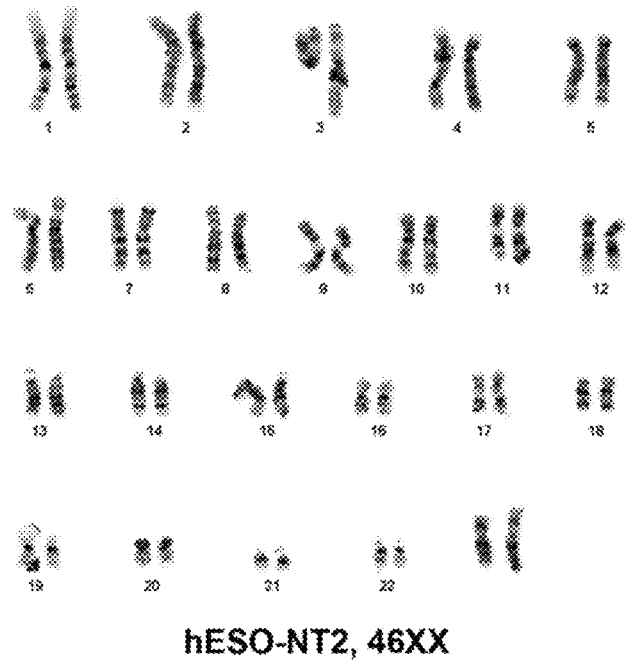
FIG. 12A is an image of a chromosome G-banding analysis for the hESO-NT2 line.
Figure 12B:
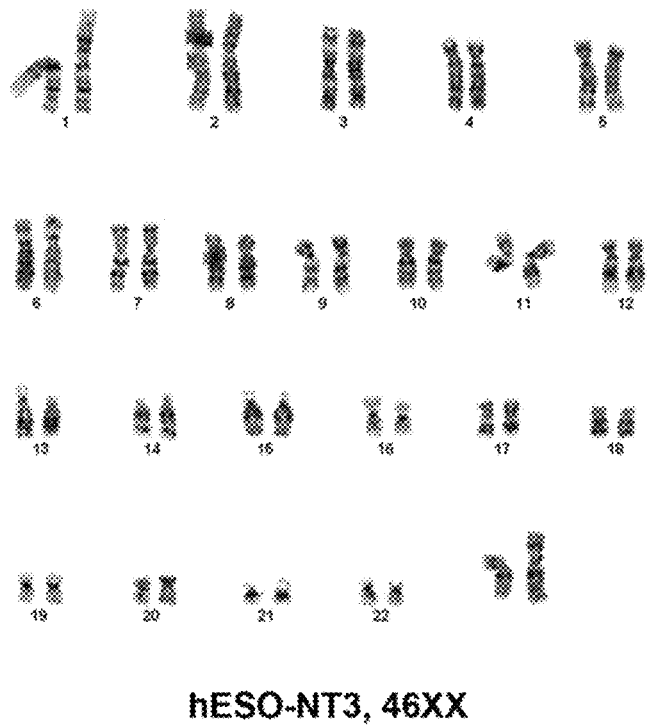
FIG. 12B is an image of a chromosome G-banding analysis for the hESO-NT3 line.
Figure 12C:
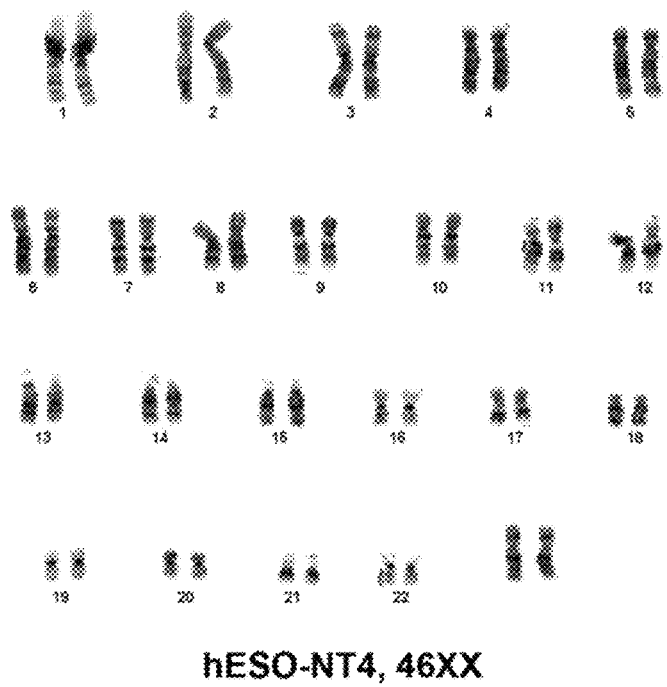
FIG. 12C is an image of a chromosome G-banding analysis for the hESO-NT4 line.
Figure 13:
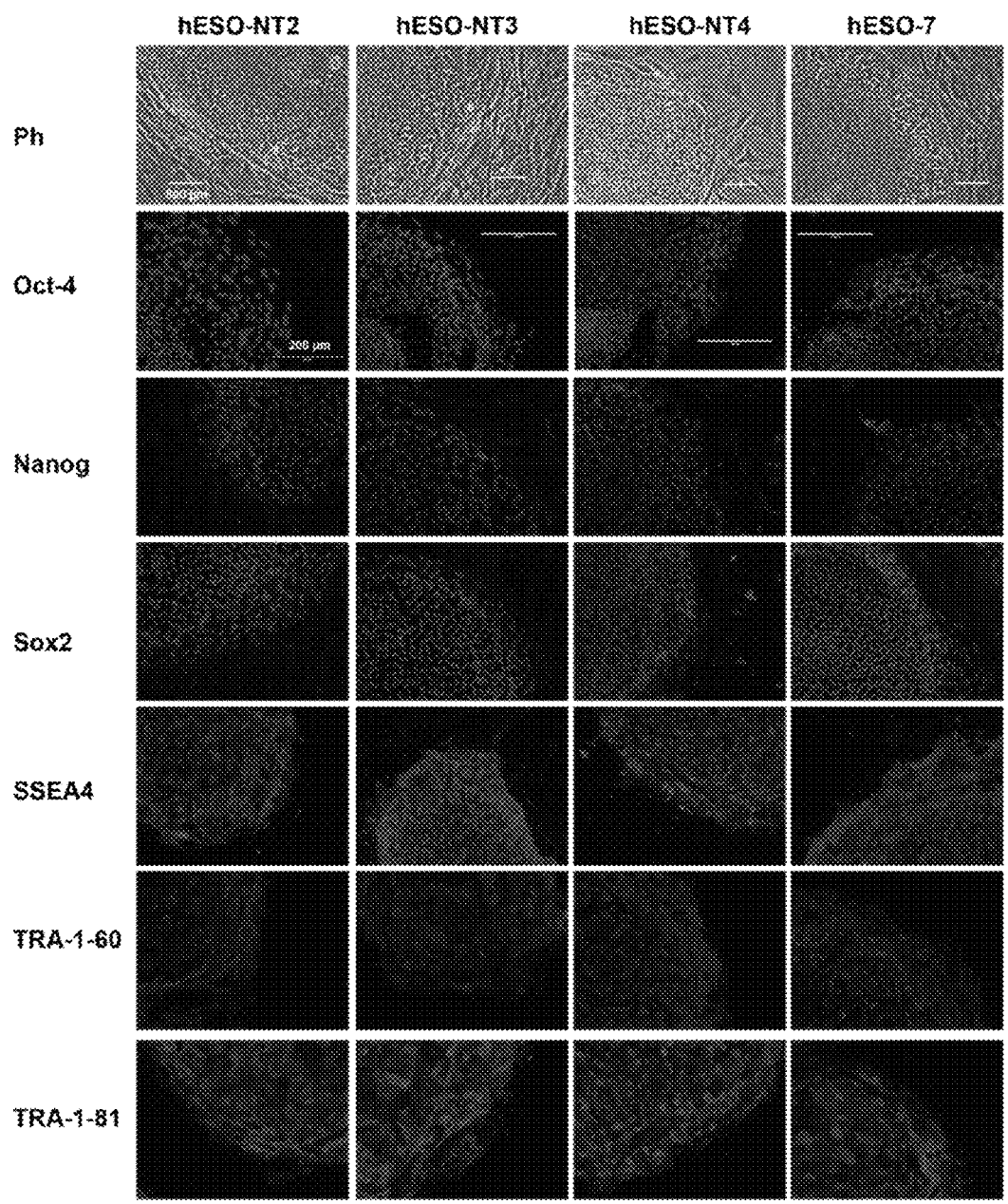
FIG. 13 is a set of images resulting from a pluripotency analysis in human ESCs derived from conventional IVF (hESO-7&-8) and SCNT (hESO-NT2, -3 and -4).

Pronuclear formation was also assessed for use as a predictive marker for SCNT outcomes. The majority of SCNT embryos formed a single pronucleus the day next after nuclear transfer (56%, 68/122), while a smaller portion (20%, 24/122) displayed 2 pronuclei (FIG. 11). As indicated above, pronuclear formation was not observed in a portion of 1-cell SCNT embryos (20%, 24/122), or they already progressed to the 2-cell stage by the time of the pronuclear check (FIG. 11). After separate culture, it was determined that cleavage and early preimplantation development was similar among these groups. While the rate of blastocyst formation was higher in SCNT embryos with 2 pronuclei (39%), stable NT-ESC lines were produced from all four types of embryos (FIG. 11). Although small numbers of SCNT embryos were analyzed, it is reasonable to conclude that pronuclear formation does not directly correlate with NT-ESC derivation.

Example 6

Analysis of Human NT-ESCs

Figures 6A, 6B:
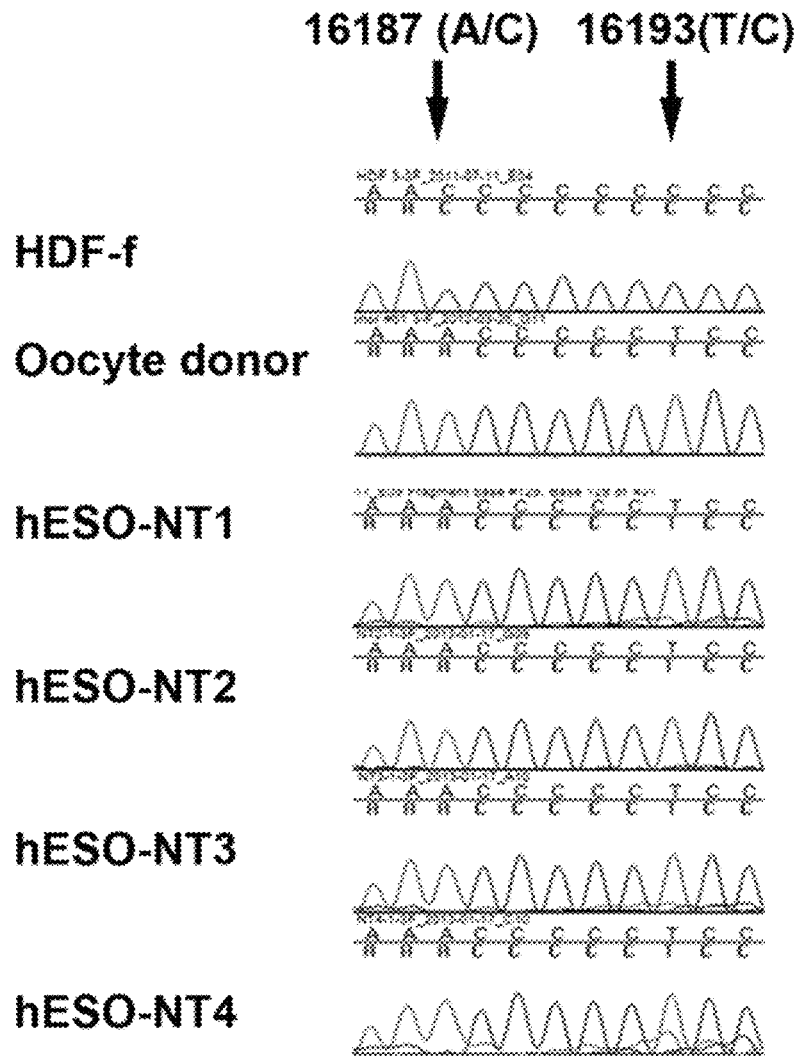
FIGS. 6A, 6B, 6C, 6D, and 6E collectively show the genetic, cytogenetic, and pluripotency analyses of human NT-ESCs
Figures 6C, 6D:
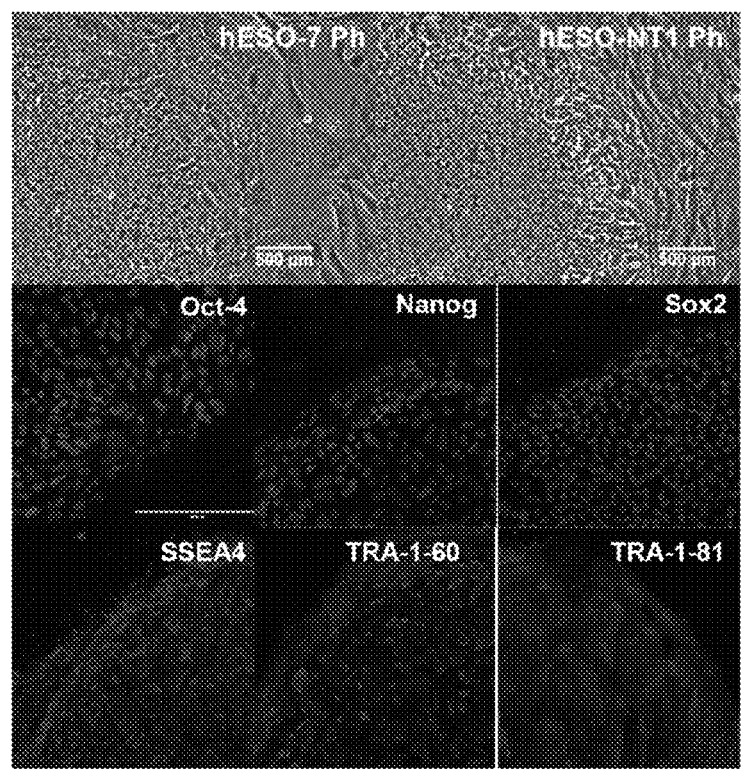

To determine the SCNT origin and to define the degree of reprogramming the four NT-ESC lines (designated as hESO-NT1, 2, 3, and 4) derived from HDF-f fetal fibroblasts, were expanded and extensively analyzed. Initially, microsatellite typing using 23 markers mapping 22 human autosomal loci and one X-linked locus for nuclear genome genotyping (Tachibana et al, 2013 supra) was used. The results undoubtedly matched all 4 NT-ESC lines to the donor fetal fibroblasts with no detectable contribution of alleles from oocytes (FIG. 6A and Table 4). The defining feature of SCNT is that the mitochondrial genome (mtDNA) in SCNT embryos and NT-ESCs is largely contributed by the oocyte. As expected, analysis of mtDNA sequence differences within the displacement loop (D-loop) containing the hypervariable segment (HSV) confirmed that NT-ESC lines inherited mainly oocyte mtDNA (FIG. 6B). During fusion of cytoplasts with nuclear donor fibroblasts, a small amount of somatic mtDNA is co-transferred into SCNT embryos that can result in heteroplasmy in NT-ESCs. Sensitive ARMS-qPCR (amplification refractory mutation system-quantitative polymerase chain reaction) was used and detected a low level of somatic mtDNA contribution in all four NT-ESC lines (3.4±1.7%; range 1.2-4.9%) (Table 5). This carryover was higher than that seen in spindle transfer-ESC lines (0.6±0.9%) derived after spindle transfer between oocytes (Tachibana et al, 2013 supra). Cytogenetic analysis by G-banding analysis indicated that all 4 NT-ESC lines contain a normal euploid female karyotype (46XX) with no numerical or structural abnormalities (FIG. 6C and Table 5).

Figure 6E:
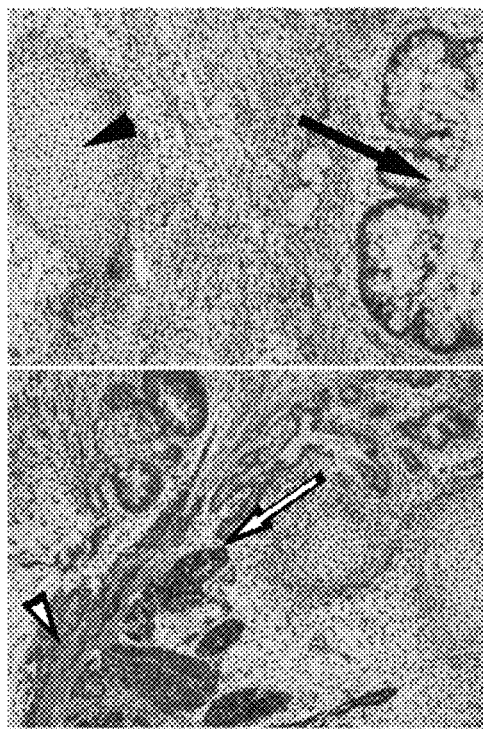

To assess pluripotency in NT-ESC lines, expression of common markers were assessed by immunocytochemistry (ICC) and compared to the two IVF-derived ESC lines (hESO-7 and -8). Note that the control ESC lines and the four NT-ESC lines were established from the oocytes donated by the same donor, thus carried identical mtDNA (Tachibana et al, 2013 supra). Similar to controls, all NT-ESC lines expressed OCT-4, NANOG, SOX2, SSEA-4, TRA-1-60 and TRA-1-81 (FIG. 6D and Table 6). When injected into immunodeficient SCID mice, all NT-ESC lines produced tumors consisting of tissue and cell types representing all three germ layers (FIG. 6E). An in vitro differentiation assay demonstrated efficient formation in embryoid bodies in suspension culture that after attachment formed spontaneously contracting cardiomyocytes).

TABLE 4

Microsatellite analysis of human NT-ESC lines

| | Sample | | | | | |
|---|---|---|---|---|---|---|
| | HDF-f | Oocyte donor | hESO-NT1 | hESO-NT2 | hESO-NT3 | hESO-NT4 |
| Sex | F | F | F | F | F | F |
| AME | XX | XX | XX | XX | XX | XX |
| D1S548 | 172/172 | 172/172 | 172/172 | 172/172 | 172/172 | 172/172 |
| D2S1333 | 293/301 | 297/305 | 293/301 | 293/301 | 293/301 | 293/301 |
| D3S1768 | 192/196 | 184/192 | 192/196 | 192/196 | 192/196 | 192/196 |
| D4S2365 | 284/296 | 296/296 | 284/296 | 284/296 | 284/296 | 284/296 |
| D4S413 | 123/123 | 133/153 | 123/123 | 123/123 | 123/123 | 123/123 |
| D5S1457 | 115/123 | 123/123 | 115/123 | 115/123 | 115/123 | 115/123 |
| D6S501 | 172/172 | 164/172 | 172/172 | 172/172 | 172/172 | 172/172 |
| D7S513 | 179/189 | 179/193 | 179/189 | 179/189 | 179/189 | 179/189 |
| D9S921 | 183/183 | 183/203 | 183/183 | 183/183 | 183/183 | 183/183 |
| D10S1412 | 162/171 | 162/165 | 162/171 | 162/171 | 162/171 | 162/171 |
| D11S2002 | 254/254 | 254/254 | 254/254 | 254/254 | 254/254 | 254/254 |
| D11S925 | 282/295 | 297/303 | 282/295 | 282/295 | 282/295 | 282/295 |
| D12S364 | 264/276 | 266/272 | 264/276 | 264/276 | 264/276 | 264/276 |
| D12S67 | 252/260 | 252/264 | 252/260 | 252/260 | 252/260 | 252/260 |
| D13S765 | 188/192 | 192/200 | 188/192 | 188/192 | 188/192 | 188/192 |
| D16S403 | 141/141 | 137/139 | 141/141 | 141/141 | 141/141 | 141/141 |
| D17S1300 | 257/257 | 257/269 | 257/257 | 257/257 | 257/257 | 257/257 |
| D18S537 | 196/200 | 196/204 | 196/200 | 196/200 | 196/200 | 196/200 |
| D18S72 | 305/305 | 305/305 | 305/305 | 305/305 | 305/305 | 305/305 |
| DXS2506 | 282/282 | 278/278 | 282/282 | 282/282 | 282/282 | 282/282 |
| MFGT22 | 104/108 | 104/108 | 104/108 | 104/108 | 104/108 | 104/108 |
| D6S291 | 201/209 | 245/249 | 201/209 | 201/209 | 201/209 | 201/209 |
| G51152 | 213/213 | ND | 213/213 | 213/213 | 213/213 | 213/213 |
| MICA | 183/195 | ND | 183/195 | 183/195 | 183/195 | 183/195 |
| MOGCA | 121/137 | ND | 121/137 | 121/137 | 121/137 | 121/137 |
| D6S276 | 251/251 | 199/209 | 251/251 | 251/251 | 251/251 | 251/251 |
| D6S1691 | 223/237 | 213/213 | 223/237 | 223/237 | 223/237 | 223/237 |

TABLE 5

Somatic mtDNA carryover in human NT-ESCs

| Cell line | mtDNA heteroplasmy % (±sd) |
|---|---|
| hESO-NT1 | 4.6 ± 0.7 |
| hESO-NT2 | 2.8 ± 0.3 |
| hESO-NT3 | 1.2 ± 0.2 |
| hESO-NT4 | 4.9 ± 0.7 |
| Average | 3.4 ± 1.7 |

Figure 14:
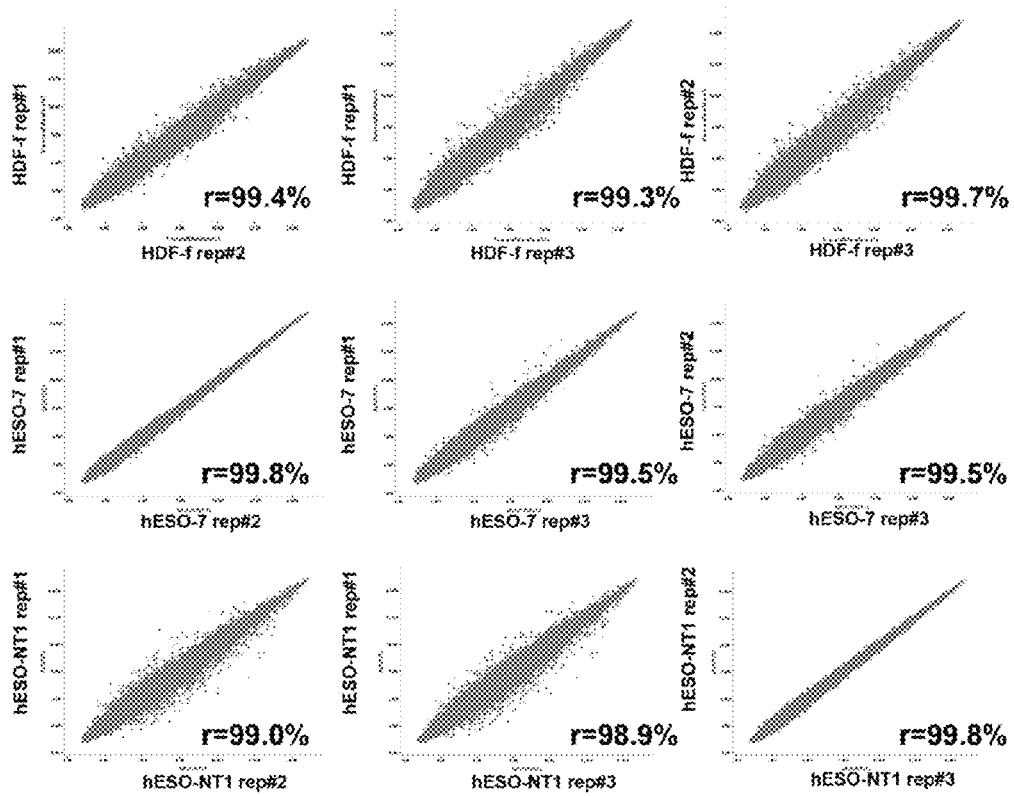
FIG. 14 is a set of nine microarray scatter plots used for comparisons of biological replications.

Lastly, a comparative microarray expression analysis of the hESO-NT1 cell line was performed relative to the IVF control hESO-7 and parental somatic HDF-f using the Affymetrix PrimeView platform. Initially, three biological replicates within each sample were compared against each other. For comparisons, the detected signal for each probe set was plotted in a scatter graph and the correlation value was calculated. This assay demonstrated 99% transcriptional correlation within each cell type suggesting that minimal variations existed between biological replicates collected from different culture plates (FIG. 14).

Figure 7A:
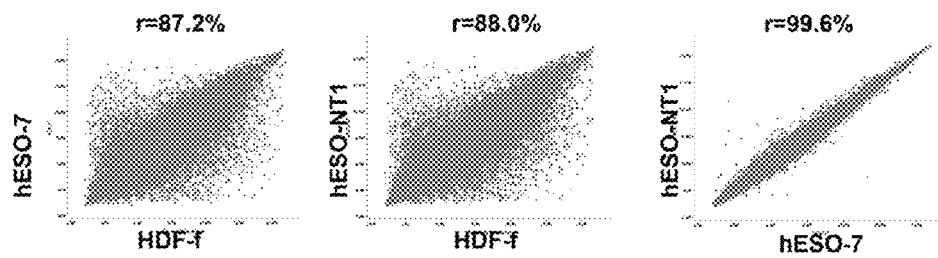
FIGS. 7A and 7B collectively show microarray expression analysis of human NT-ESC's.
Figure 7B:
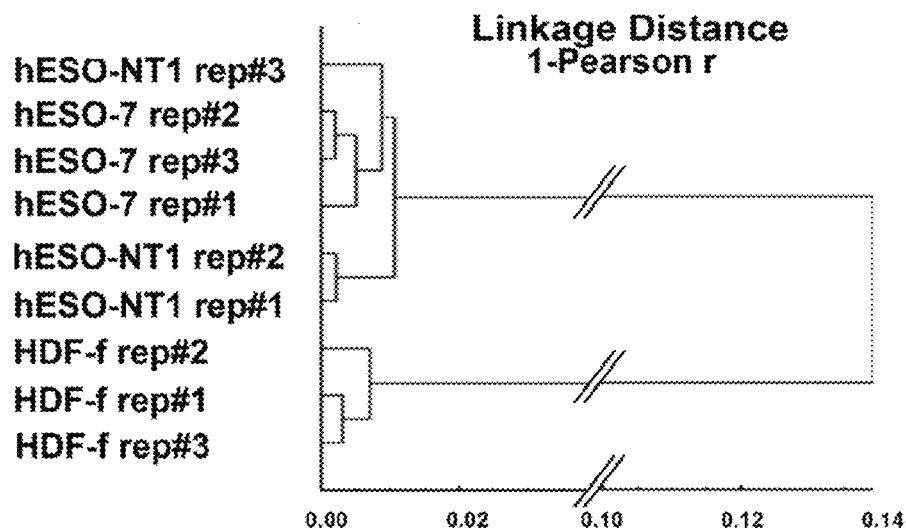

Next, each NT-ESC and IVF-ESC types were compared against each other and to somatic cells (HDF-f). As expected, both stem cell types displayed low transcriptional correlation to fibroblasts (FIG. 7A and FIG. 7B). Among 50 genes with the highest fold change, many known pluripotency genes were observed including LIN28, POU5F1, NANOG, and SOX2 (Table 6). In contrast, ESCs derived by IVF and SCNT were similar to each other (FIGS. 7A and B). Some transcriptional differences between human NT-ESCs and IVF-ESCs were observed, however no known pluripotency genes were included in this list (Table S7 and S8). Interestingly, an HLA-C major histocompatibility gene was highly downregulated in hESO-NT1 compared with hESO-7 (79 fold) (Table 8).

TABLE 6

Genes highly expressed in human NT-ESCs (hESO-NT1 and control IVF-ESCs (hESO-7) compared to parental fibroblasts.

| No. | Affymetrix Probe Set ID | Gene Name | Gene symbol | Gene expression fold change* hESO-7 | hESO-NT1 |
|---|---|---|---|---|---|
| 1 | 11725430_at | Lin-28 homolog | LIN28 | 758 | 750 |
| 2 | 11723364_at | LINE-1 type transposase domain containing 1 | L1TD1 | 435 | 381 |
| 3 | 11720993_at | SRY (sex determining region Y)-box 2 | SOX2 | 429 | 395 |
| 4 | 11723191_at | Zic family member 2 | ZIC2 | 418 | 373 |
| 5 | 11717386_s_at | Metallothionein 1G | MT1G | 343 | 168 |
| 6 | 11755599_x_at | POU class 5 homeobox 1 | POU5F1 | 340 | 316 |
| 7 | 11736127_s_at | Developmental pluripotency associated 4 | DPPA4 | 340 | 295 |
| 8 | 11730462_s_at | Orthodenticle homeobox 2 | OTX2 | 326 | 381 |
| 9 | 11719444_s_at | Protein tyrosine phosphatase, receptor-type, Z polypeptide 1 | PTPRZ1 | 316 | 321 |
| 10 | 11740301_a_at | Ubiquitin specific peptidase 44 | USP44 | 314 | 261 |
| 11 | 11745651_a_at | Epithellial cell adhesion molecule | EPCAM | 312 | 347 |
| 12 | 11716906_a_at | Cadherin 1, type 1, E-cadherin (epithelial) | CDH1 | 286 | 200 |
| 13 | 11759218_at | Zic family member 3 | ZIC3 | 283 | 220 |
| 14 | 11733551_at | Zic family memeber 5 | ZIC5 | 252 | 238 |
| 15 | 11720460_x_at | F11 receptor | F11R | 247 | 223 |
| 16 | 11746506_a_at | Secreted phosphoprotein 1 | SPP1 | 241 | 340 |
| 17 | 11719869_a_at | V-myc myelocytomatosis viral related oncogene, | MYCN | 241 | 221 |
| 18 | 11727909_at | Solute carrier family 7 (cationic amino acid transporter, y+ system), member 3 | SLC7A3 | 240 | 226 |
| 19 | 11747223_a_at | Endothelin receptor type B | EDNRB | 230 | 245 |

TABLE 6-continued

Genes highly expressed in human NT-ESCs (hESO-NT1 and control IVF-ESCs (hESO-7) compared to parental fibroblasts.

| No. | Affymetrix Probe Set ID | Gene Name | Gene symbol | Gene expression fold change* hESO-7 | hESO-NT1 |
|---|---|---|---|---|---|
| 20 | 11723543_a_at | Epithelial splicing regulatory protein 1 | ESRP1 | 222 | 191 |
| 21 | 11746022_s_at | teratocarcinoma-derived growth factor 1 | TDGF1 | 210 | 227 |
| 22 | 11758000_s_at | Coxsackie virus and adenovirus receptor | CXADR | 205 | 204 |
| 23 | 11725749_a_at | Galanin prepropeptide | GAL | 203 | 308 |
| 24 | 11725436_a_at | Secretoglobin, family 3A, member 2 | SCGB3A2 | 200 | 182 |
| 25 | 11729643_s_at | Tumor protein D52 | TPD52 | 194 | 165 |
| 26 | 11734366_x_at | Zinc finger protein 42 homolog | ZFP42 | 194 | 186 |
| 27 | 11733474_at | SRY (sex determining region Y)-box 21 | SOX21 | 190 | 122 |
| 28 | 11721990_at | Leukocyte cell derived chemotaxin 1 | LECT1 | 185 | 135 |
| 29 | 11716017_at | Mal, T-cell differentiation protein 2 | MAL2 | 183 | 179 |
| 30 | 11719684_a_at | Neurotensin | NTS | 181 | 255 |
| 31 | 11725237_a_at | RNA binding protein with multiple splicing 2 | RBPMS2 | 157 | 163 |
| 32 | 11734427_at | Tripartite motif-containing 71 | TRIM71 | 157 | 138 |
| 33 | 11757573_s_at | Frizzled homolog 5 | FZD5 | 154 | 115 |
| 34 | 11755164_a_at | Left-right determination factor 1 | LEFTY1 | 148 | 117 |
| 35 | 11731121_s_at | Vasohibin 2 | VASH2 | 147 | 90 |
| 36 | 11727987_a_at | DNA (cytosine-5-)-methyltransferase 3 beta | DNMT3B | 147 | 110 |
| 37 | 11748773_a_at | Cathepsin L2 | CTSL2 | 137 | 169 |
| 38 | 11718350_s_at | NLR family, pyrin domain containing 2 | NLRP2 | 134 | 88 |
| 39 | 11757625_s_at | CD200 molecule | CD200 | 128 | 133 |
| 40 | 11729429_a_at | Kinesin family memeber 26A | KIF26A | 127 | 105 |
| 41 | 11757702_s_at | Desmocollin 2 | DSC2 | 118 | 146 |
| 42 | 11732577_x_at | Nanog homeobox | NANOG | 111 | 154 |
| 43 | 11728591_at | Hypothetical protein LOC729993 | LOC729993 | 111 | 127 |
| 44 | 11759881_at | Peptidylprolyl isomerase A (cyclophilin A) | PPIA | 103 | 114 |
| 45 | 11756165_s_at | Glycine dehydrogenase (decarboxylating) | GLDC | 102 | 116 |
| 46 | 11747042_a_at | Contactin associated protein-like 2 | CNTNAP2 | 91 | 142 |
| 47 | 11725524_s_at | Desmoglein 2 | DSG2 | 91 | 91 |
| 48 | 11731989_at | HESX homeobox 1 | HESX1 | 91 | 73 |
| 49 | 11758166_s_at | Kallmann syndrome 1 sequence | KAL1 | 88 | 124 |
| 50 | 11732657_a_at | Cytochrome P450, family 26, subfamily A, polypeptide 1 | CYP26A1 | 88 | 110 |

TABLE 7

Highly upregulated genes in NT-ESCs (hESO-NT1) compared to IVF-ESC (hESO-7)

| No. | Affymetrix Probe Set ID | Gene Name | Gene symbol | Gene expression fold change* |
|---|---|---|---|---|
| 1 | 11755911_a_at | G protein-coupled receptor 128 | GPR128 | 115 |
| 2 | 11722472_a_at | paternally expressed 3 | MEG3 | 26 |
| 3 | 11728941_at | Chromosome 13 open reading frame 38 | C13orf38 | 12 |
| 4 | 11740844_s_at | Von Willebrand factor D and EGF domains | VWDE | 11 |
| 5 | 11737126_x_at | Similar to CTAGE6 | LOC441294 | 8 |
| 6 | 11720703_at | Myosin, light chain 4, alkali; atrial, embryonic | MYL4 | 5 |
| 7 | 11736163_a_at | Cyclin-dependent kinase inhibitor 2B (p15, inhibits CDK4) | CDKN2B | 4 |
| 8 | 11759120_a_at | Leucine-rich repeat-containing G protein-coupled receptor 5 | LGR5 | 4 |
| 9 | 11746373_s_at | RRN3 RNA polymerase I transcription factor homolog | RRN3 | 4 |
| 10 | 11727675_at | Molybdenum cofactor sulfurase | MOCOS | 4 |

TABLE 7-continued

Highly upregulated genes in NT-ESCs (hESO-NT1) compared to IVF-ESC (hESO-7)

| No. | Affymetrix Probe Set ID | Gene Name | Gene symbol | Gene expression fold change* |
|---|---|---|---|---|
| 11 | 11760343_x_at | zinc finger protein 726 | ZNF726 | 4 |
| 12 | 11717912_s_at | Chemokine (C-X-C motif) ligand 14 | CXCL14 | 4 |
| 13 | 11735201_x_at | NEDD4 binding protein 2 | N4BP2 | 4 |
| 14 | 11744894_at | Family with sequence similarity 20, member A | FAM20A | 4 |
| 15 | 11764141_x_at | Solute carrier family 25 (mitochondrial carrier: citrate transporter), member 1 | SLC25A1 | 4 |
| 16 | 11757096_s_at | Zinc finger protein 98 (F7175) | ZNF98 | 4 |
| 17 | 11718766_at | Protease, serine, 23 | PRSS23 | 3 |
| 18 | 11729820_at | Up-regulated during skeletal muscle growth 5 homolog | USMG5 | 3 |
| 19 | 11756542_a_at | G protein-coupled receptor 87 | GPR87 | 3 |
| 20 | 11719120_a_at | Kynureninase (L-kynurenine hydrolase) | KYNU | 3 |
| 21 | 11750167_a_at | Calpain 2, (m/II) large subunit | CAPN2 | 3 |
| 22 | 11727117_at | Natriuretic peptide precursor B | NPPB | 3 |
| 23 | 11744435_a_at | Dual specificity phosphatase 6 | DUSP6 | 3 |
| 24 | 11716433_s_at | Stearoyl-CoA desaturase 5 | SCD5 | 3 |
| 25 | 11715796_s_at | Lumican | LUM | 3 |

TABLE 8

Highly downregulated genes in human NT-ESCs

| No. | Affymetrix Probe Set ID | Gene Name | Gene symbol | Gene expression fold change* |
|---|---|---|---|---|
| 1 | 11715316_x_at | Major histocompatibility complex, class I, C | HLA-C | 79 |
| 2 | 11763252_x_at | Phosphoserine phosphatase | PSPH | 9 |
| 3 | 11730995_a_at | Actinin, alpha 3 | ACTN3 | 6 |
| 4 | 11759838_x_at | Zinc finger protein 506 | ZNF506 | 5 |
| 5 | 11747933_a_at | Nicotinate phosphoriboxyl-transferase domain containing 1 | NAPRT1 | 5 |
| 6 | 11720803_at | S100 calcium binding protein A14 | S100A14 | 4 |
| 7 | 11716034_a_at | Bone marrow stromal cell antigen 2 | BST2 | 4 |
| 8 | 11720549_a_at | Peroxisomal biogenesis factor 6 | PEX6 | 4 |
| 9 | 11746500_x_at | gluthathion S-transferase omega 2 | GSTO1 | 3 |
| 10 | 11755044_x_at | Pigeon homolog | PION | 3 |
| 11 | 11726063_a_at | Chromosome 2 open reading frame 40 | C2orf40 | 3 |
| 12 | 11732934_a_at | Developmental pluripotency associated 5 | DPPA5 | 3 |
| 13 | 11730250_a_at | Ligand of numb-protein X 1 | LNX1 | 3 |
| 14 | 11733305_a_at | Transcription factor AP-2 beta (activating enhancer binding protein 2 beta) | TFAP2B | 3 |
| 15 | 11728437_at | Bromodomain and WD repeat domain containing 1 | BRWD1 | 3 |
| 16 | 11734175_a_at | Chromosome 13 open reading frame 38 | C12orf38 | 3 |
| 17 | 11728244_s_at | Solute carrier family 12 (sodium/potassium/chloride transporters), member I | SLC12A1 | 3 |
| 18 | 11755819_a_at | DEAD (Asp-Glu-Ala-Asp) box polypeptide 58 | DDX58 | 2 |
| 19 | 11746803_s_at | Developmental pluripotency associated 3 | DPPA3 | 2 |
| 20 | 11717191_a_at | Troponin C type 2 (fast) | TNNC2 | 2 |
| 21 | 11731771_at | Protocadherin beta 15 | PCDHB15 | 2 |
| 22 | 11719028_a_at | Pleckstrin and Sec7 domain containing 3 | PSD3 | 2 |
| 23 | 11718230_a_at | Major histocompatibility complex complex, class I, F | HLA-F | 2 |
| 24 | 11743972_a_at | DNA-damage-inducible transcript 4 | DDIT4 | 2 |
| 25 | 11725196_s_at | Zinc finger, SWIM-type containing 7 | ZSWIM7 | 2 |

Example 7

Procedures

Rhesus Macaque SCNT:

Oocyte collections, SCNT, embryo culture and NT-ESC isolation procedures were performed as previously described (Byrne et al, 2007 supra; Sparman et al., 2009, supra; Sparman et al, 2010 supra).

Human Oocyte Donations:

Anonymous oocyte donors of age 23-31 were recruited through the OHSU Women's Health Research Unit via print and web-based advertising. Responding women were screened with respect to their reproductive, medical and psychosocial health. Healthy and non-obese (BMI <28 kg/m$^2$) women, who passed the initial medical and psychological evaluations, were invited to a research egg donation.

Ovarian stimulation protocols followed established clinical IVF guidelines as we described previously (Tachibana et al, 2013 supra). Briefly, a combination of recombinant follicle stimulating hormone (rFSH) and human menopausal gonadotropins (hMG) and either GnRH agonist (Lupron®, Tap Pharmaceutical Products, Lake Forest, Ill.) or antagonist (Ganirelix®, Merck & Co, Whitehouse Station, N.J.) were given. Human chorionic gonadotropin (hCG) was prescribed to trigger oocyte maturation. Self administration of injectable rFSH (sc, Follistim®, Merck & Co, Whitehouse Station, N.J.) commenced on cycle day 2 or 3 and continued for approximately 8-12 days. The starting gonadotropin dose was 75-125 IU/day and 1-2 A hMG (sc, Menopur®, Ferring Pharmaceuticals, Inc. Parsippany, N.J.); the dose was adjusted per individual response using an established step-down regimen until the day of hCG injection. Ovarian response and follicular growth were monitored by transvaginal ultrasound and measurements of serum estradiol levels. When two or more follicles reached >18 mm in diameter, subjects received hCG (104 IU, sc, Ovidrel®, EMDSerono, Rockland, Mass.) to trigger maturation. Thirty-six hours following hCG injection, subjects underwent oocyte retrieval via transvaginal follicular aspirations.

Cumulus-oocyte complexes (COCs) were collected from aspirates and placed in HTF w/HEPES medium (LifeGlobal®, IVFonline, LLC) supplemented with 10% Serum Protein Substitute (Quinns Advantage Serum®, CooperSurgical, INC) (HTF w/HEPES 10%) at 37° C. COCs were treated with hyaluronidase to disaggregate cumulus and granulosa cells. Oocytes were isolated and classified as germinal vesicle, meiotic metaphase I (MI) and mature metaphase II (MII) stage, and then placed in Global® medium (LifeGlobal®, IVFonline, LLC) supplemented with 10% Serum Protein Substitute (Quinns Advantage Serum®, CooperSurgical, INC) (Global 10%) at 37° C. in 5% $CO_2$ and covered with tissue culture oil (Sage IVF®, Cooper Surgical, Inc).

Nuclear Donor Cell Preparations:

Commercially available female dermal fibroblasts of fetal origin (HDF-f) were obtained from ScienCell Research Laboratories. Cells were expanded in 75 cm$^3$ cell culture flasks (Corning) containing DMEM/F12 supplemented with 100 IU ml-1 penicillin, 100 μg ml-1 streptomycin (Invitrogen), 10% FBS at 37° C. in 5% $CO_2$. Fibroblasts were then disaggregated with trypsin treatment and frozen down in aliquots of 3×10$^5$ cells in medium containing 10% dimethyl sulphoxide (DMSO). Cells were subsequently thawed prior to the SCNT and cultured in 4-well dishes (Nunc) under standard conditions until confluency. Confluent cells were synchronized in the $G_0/G_1$ phase of the cell cycle by culture in DMEM/F12 medium with 0.5% FBS for 2-4 days before SCNT.

Human SCNT Procedures and Embryo Culture:

Enucleation of MII spindles were performed as described previously (Tachibana et al., 2013 supra). Oocytes were placed into 50 μl manipulation droplet of HTF w/HEPES 10% medium containing 5 μg/ml cytochalasin B and 1.25 mM caffeine in a glass-bottom dish. The droplet was covered with tissue culture oil and oocytes maintained at 37° C. for 10-15 min before spindle removal. The dish was then mounted on the stage of an inverted microscope (Olympus IX71®) equipped with a stage warmer (http://www.tokaihit-.com) Narishige micromanipulators, Oosight™ Imaging System (www.cri-inc.com) and a laser objective (www.hamiltonthorne.com). An oocyte was positioned by a holding pipette so that the spindle was situated between the 2 o'clock and 4 o'clock position. The zona pellucida next to the spindle was drilled with a laser pulse and an enucleation pipette was inserted through the opening. A small amount of cytoplasm surrounded by plasma membrane and contacting spindle was aspirated into the pipette. Next, a disaggregated fibroblast was aspirated into a micropipette and briefly transferred to the drop containing HVJ-E extract (Ishihara Sangyo Kaisha Ltd). The cell was then placed into the perivitelline space of the cytoplast on the side opposite the first polar body. SCNT constructs were rinsed with HTF w/HEPES 10%, transferred to Global 10% medium and incubated at 37° C. in 5% $CO_2$ for 30 min until fusion. Successful fusion was confirmed visually 30 min by the disappearance of the donor cell in the perivitelline space. Reconstructed oocytes were then subjected to artificial activation consisting of electroporation pulse (two 50 μs DC pulses of 2.7 kV cm$^{-1}$) (Electro Square Porator T-820, BTX, Inc.) in 0.25 M d-sorbitol buffer containing 0.1 mM calcium acetate, 0.5 mM magnesium acetate, 0.5 mM HEPES and 1 mg ml-1 fatty-acid-free BSA. Activated SCNT constructs were then incubated in Global® medium (w/o serum) containing 2 mM DMAP at 37° C. in 6% CO2 for 4 h. After DMAP, SCNT embryos were rinsed with HTF w/HEPES 10% SSS and transferred into 4-well dishes containing Global® medium supplemented with 10% FBS, 12 μM β-mercaptoethanol (BME), 10 nM Trichostatin A (TSA, Sigma) and cultured at 37° C. in 6% $CO_2$, 5% $O_2$ and 89% $N_2$ for 12 hours. Embryos were then rinsed, checked for pronuclear formation and cultured in Global® medium supplemented with 10% FBS and 12 μM β-mercaptoethanol (BME) at 37° C. in 6% $CO_2$, 5% $O_2$ and 89% $N_2$ for a maximum of 7 days. Medium was changed once at day 3 of culture.

Isolation, Culture and Characterization of Human NT-ESCs:

After removal of the zona pellucida with a brief exposure to 0.5% protease (Sigma), SCNT blastocysts were plated onto confluent feeder layers of mitomycin C inactivated mouse embryonic fibroblasts (mEFs) and cultured for 5-7 days at 37° C., 3% $CO_2$, 5% $O_2$ and 92% $N_2$ in ESC derivation medium. The derivation medium consisted of DMEM/F12 (Invitrogen) supplemented with 0.1 mM non-essential amino acids, 1 mM I-glutamine, 0.1 mM β-mercaptoethanol, 5 ng/ml basic fibroblast growth factor, 10 μM ROCK inhibitor (Sigma), 10% FBS and 10% knockout serum replacement (KSR; Invitrogen). Before use, fresh ESC derivation medium was mixed (50%:50%, v/v) with derivation medium conditioned for 24 h culture with growing human ESCs. Outgrowths of the inner cell mass (ICM) were manually dissociated into small clumps with a microscalpel and replated on fresh mEF plates. After the first passage of ICM outgrowth, FBS and ROCK inhibitor were omitted and KSR was increased to 20%. Colonies with ESC-like morphologies were selected for further propagation, characterization and cytogenetic analyses. Immunocytochemistry, in vivo and in vitro differentiation and microarray analyses were performed as described (Byrne et al, 2007 supra; Mitalipov et al, 2007 supra; Tachibana et al, 2013 supra). Detailed protocols are also available in Supplemental procedures.

Nuclear DNA Genotyping and Cytogenetic Analyses:

Genotyping of NT-ESCs was performed by microsatellite typing using 23 markers representing 22 human autosomal loci and one X-linked locus as previously described (Tachibana et al, 2013 supra). Karyotyping was performed by GWT-banding on 20 metaphase cells from each human NT-ESC line at the Human Genetics Laboratory, University of Nebraska Medical Center as previously described (Tachibana et al, 2013 supra).

MtDNA Genotyping:

Genotyping of mtDNA was performed as previously described (Tachibana et al, 2013 supra). The region of human mitochondrial displacement loop (D-loop) harboring the hypervariable segment 1(HSV-1) was amplified using published primers (Danan C et al, *Am J Hum Genetics* 65, 463-473 (1999); incorporated by reference herein). PCR products were sequenced and the informative single nucleotide polymorphic (SNP) sites were identified using Sequencher® v. 4.7 software (GeneCodes). Quantitative mtDNA analysis was performed by ARMS-qPCR as described (Tachibana et al, 2013 supra).

Immunocytochemistry:

Immunocytochemical analysis was performed as previously described (Tachibana et al, 2013 supra) using antibodies for OCT-4, SOX2, TRA1-60, TRA1-81, and SSEA-4 from Applied StemCell. NANOG antibody was from R&D Systems, Inc. Nuclei were labeled with DAPI (Molecular Probes).

Teratoma Assay:

Approximately 3-5 million of undifferentiated ESCs were injected into the hind-leg muscle of 4-week-old, SCID, beige male mice using an 18 gauge needle. Six to seven weeks after injection, mice were euthanized and tumors dissected, sectioned and histologically characterized for the presence of representative tissues as described previously (Tachibana et al, 2013 supra).

Cardiac Differentiation:

Differentiation into cardiac cells was initiated by embryoid body formation in a suspension culture as described (Byrne et al, 2007 supra). Briefly, ESC colonies were loosely detached from feeder cells and transferred into feeder-free, 6-well, ultra-low adhesion plates (Corning Costar) and cultured in suspension in ESC medium supplemented with 20% FBS but without FGF for 5-7 days. Embryoid bodies were then plated into collagen-coated dishes and cultures were maintained in ESC medium for additional 2-4 weeks until spontaneously contracting cardiomyocytes were observed.

ARMS-qPCR Assay:

The Amplification Refractory Mutation System quantitative PCR assay was performed to measure mtDNA carryover levels in ESCs as previously described (Tachibana et al., 2013). Primers and TaqMan® MGB probes were designed to detect unique mtDNA SNPs between HDF-f skin fibroblast donor cells and egg donor mtDNA haplotypes. The non-discriminative and discriminative assays were mixed and measured with Rotor-Gene® Multiplex PCR Kit (Qiagen). PCR reactions (15 μl) containing 1×PCR Master Mix, 100-250 nM each primer, 150 nM each TaqMan probe and about 1-4 ng of total genomic DNA were performed according to the manufacturer's instructions. The fluorescent signal intensities were recorded and analyzed during PCR in an ABI 7900HT® fast real-time PCR system (Applied Biosystems) using SDS® (Ver. 2.4) software. All reactions were run in duplicate with two different amounts of input DNA: 1-4 ng and 1:8 dilutions. The SDS software generated a standard curve using four 8-fold dilutions plus a last 4-fold dilution. The percentage of carryover mtDNA in relation to the total mtDNA content was calculated by the equation heteroplasmy=100*(Quantity D/Quantity ND).

Transcriptional Profiling by Microarray:

Comparative microarray analysis of mRNA for hESO-NT1, hESO-7 and HDF-f was carried out using the Affymetrix PrimeView® human genome array. RNA samples were converted to labeled cRNA and hybridized to PrimeView® Human Gene Expression Array (Affymetrix, Inc.). The distribution of fluorescent material on the processed array was determined using the GeneChip Scanner 3000® with the 7G upgrade (Affymetrix) and AGCC version 3.2 software (Affymetrix), yielding cell fluorescence intensity (.cel files). Image inspection was performed manually immediately following each scan. Processed image files were normalized across arrays using the robust multichip average algorithm (Irizarry R A et al, Biostatistics 4 249-264 (2003); incorporated by reference herein) and log transformed (base 2) to perform direct comparisons of probe set values between samples. GeneSifter® (VizX Labs, Seattle, Wash.) microarray expression analysis software was used to identify differentially expressed transcripts. For a given comparison, IVF-derived ESCs were selected as the baseline reference, and transcripts that exhibited various fold change relative to the baseline were considered differentially expressed. To facilitate in-depth comparisons, processed image files were normalized with the robust multichip average algorithm and log transformed (base 2) using the StatView® program. Corresponding microarray expression data were analyzed by pairwise differences determined with the Student-t-test ($P<0.05$).

Statistics:

For embryo development and clinical parameters, statistical analyses were performed using ANOVA or t-test with Statview® Software (SAS Institute, Inc.) with statistical significance set at 0.05. ESC isolation efficiencies were analyzed using chi square with statistical significance set at 0.05.

Example 8

Comparison of Pluripotent Stem Cells Derived from Somatic Cell Nuclear Transfer with Those Derived by IVF and Induced Pluripotent Stem Cells Human pluripotent stem cells hold great potential for regenerative medicine, but available cell types have important limitations. While embryonic stem cells derived from fertilized embryos (IVF-ESCs) are considered the "gold standard" of pluripotency, they are allogeneic to potential recipients. Likewise, autologous induced pluripotent stem cells (iPSCs) are prone to epigenetic and transcriptional aberrations. To determine whether accumulation of such aberrations is intrinsic to somatic cell reprogramming or secondary to the reprogramming method, a genetically matched collection of human IVF-ESCs, iPSCs, and ESCs derived by somatic cell nuclear transfer (SCNT; NT-ESCs) were generated and subjected to genome-wide genetic, epigenetic and transcriptional analyses. SCNT-based reprogramming is mediated by the full complement of oocyte cytoplasmic factors, thus closely recapitulating early embryogenesis. NT-ESCs and iPSCs derived from the same somatic donor cells contained comparable numbers of de novo copy number variations (CNVs), suggesting that the two reprogramming methods may not differ significantly in terms of mutagenic or selective pressure.

In contrast, the DNA methylation and transcriptome profiles of NT-ESCs corresponded very closely to those of IVF-ESCs, while iPSCs differed markedly from IVF-ESCs and harbored residual DNA methylation patterns typical of parental fibroblasts, suggesting incomplete reprogramming. We conclude that human somatic cells can be faithfully reprogrammed to pluripotency by SCNT and are, therefore, ideal candidates for cell replacement therapies.

Background:

The derivation of human ESCs from in vitro fertilized embryos (Thomson J A et al, Science 282, 1145-1147 (1998); incorporated by reference herein) was met with enthusiasm due to their potential use in cell-based therapies, tempered only by the recognition that lifelong immunosuppression would be required for engraftment and survival of allogeneic IVF-ESCs. The advent of iPSC technology (Takahashi K et al, Cell 131, 861-872 (2007) and Rais Y et al, Nature 502, 65-70 (2013); both of which are incorporated by reference herein) overcomes this limitation, since patient-matched cells can be produced relatively easily and economically.

However, concerns have recently arisen due to the high frequency of genetic and epigenetic abnormalities observed in iPSCs, including subchromosomal duplications and deletions detected as copy number variations (CNVs) (Hussein S M et al, Nature 471, 58-62 (2011) and Laurent L C et al, Nature Comm 4, 1382 (2013); both of which are incorporated by reference herein), protein-coding mutations (Ruiz S et al, Nature Comm 4, 1382 (2013), incorporated by reference herein) and defects in DNA methylation and gene expression at regions subject to imprinting and X chromosome inactivation (Nazor K L et al, Cell Stem Cell 10 620-634 (2012); Lister R et al, Nature 471, 68-73 (2011); Ohi Y et al, Nature Cell Biol 13, 541-549 (2011); and Ruiz S et al, Proc Natl Acad Sci USA 109, 16196-16201 (2012); all of which are incorporated by reference herein).

While it is not yet understood whether these aberrant epigenetic marks reflect errors arising during reprogramming or incomplete reversion to pluripotency, these abnormalities could impact the accuracy of in vitro disease modeling or the utility of iPSCs for regenerative medicine. With the availability of SCNT as an alternative approach to somatic cell reprogramming (Tachibana M et al, Cell 153, 1228-1238 (2013); incorporated by reference herein), a study to explore the mechanisms underlying transcription factor- and SCNT-based reprogramming was initiated.

Although the molecules responsible for SCNT-based reprogramming remain largely unknown, it is generally accepted that the cytoplasmic factors involved are different from those used for generation of iPSCs. For instance, OCT4 plays a critical role in the induction and maintenance of pluripotency in iPSCs but is not required in oocyte-based reprogramming (Wu G et al, Nature Cell Biol 15, 1089-1097 (2013); incorporated by reference herein.)

The hypothesis that distinct mechanisms underlying SCNT- and factor-based reprogramming lead to differences in the genetic and epigenetic stability of the resulting pluripotent cells was tested. A matched collection of NT-ESC and iPSC lines was generated from the same parental somatic cells. As controls, IVF-ESCs were produced using oocytes from the same donor who provided the providing oocytes for SCNT. We subjected the cell lines to high-resolution genetic, epigenetic and transcriptional analyses, thereby defining the distinct molecular profiles of each pluripotent stem cell type.

Derivation of Genetically Matched Lines:

Four human NT-ESC lines from fetal dermal fibroblasts (HDFs), designated NT1-4 were previously generated (See Tachibana et al, 2013 supra). Described herein, generated genetically matched iPSCs from the same HDF culture were also generated. Two reprogramming vectors were used; 1) integrative retroviral vectors carrying OCT4, SOX2, KLF4, and MYC (Lowry W E et al, Proc Natl Acad Sci USA 105, 2883-2888 (2008); incorporated by reference herein) and 2) non-integrative Sendai virus-based vectors carrying the same four factors (Fusaki N et al, Proc Japan Acad Series B 85, 348-362 (2009); incorporated by reference herein). Colonies were randomly based on typical ESC-morphology. Five iPSC clones/lines produced from the Sendai technique were expanded and designated iPS-S1-5. Two lines produced from retroviral transduction were expanded and designated iPS-R1 and -R2.

Two IVF-ESC lines, designated hESO-7 and -8, were derived from blastocysts generated by IVF of oocytes from the same donor that were used for SCNT. All cell lines were generated in one laboratory and the passaging and culture conditions were identical. Similar to IVF-ESCs and NT-ESCs, all iPSC lines maintained typical ESC morphology, expressed pluripotency markers (Tachibana et al, 2011 supra, and Tachibana M et al, Nature 493, 627-631 (2013); incorporated by reference herein) and were capable of forming teratomas containing cells representing all three germ lineages. Cytogenetic G-banding analysis confirmed that all pluripotent cell lines retained a diploid karyotype with no detectable numerical or structural chromosomal abnormalities.

Short tandem repeat (STR)-based genotyping using 1 marker for gender determination (AME) and 22 distinct markers distributed over 16 chromosomes (15 autosomes and the X chromosome) verified that all NT-ESC and iPSC lines were genetically matched to each other and to the original HDFs. The only line that did not show perfect concordance for all 23 STR markers was the iPS-R1cell line which displayed homozygosity at the D3S1768 locus on chromosome 3 compared to the HDFs and other reprogrammed cell lines, which were all heterozygous at this locus. This suggested that a loss-of-heterozygosity had occurred in the iPS-R1cell line.

High-resolution microarray-based single nucleotide polymorphism (SNP) genotyping was performed to allow detailed genetic comparisons among stem cells, parental HDFs and oocyte and sperm donors. Replicate Error Analysis confirmed that all NT-ESC and iPSC lines, excluding iPS-R1, were essentially identical to each other and to the parental HDFs (>99.96% similarity). Notably, iPS-R1 displayed a higher number of differences compared to HDFs (99.855% similarity). Consistent with the STR analysis, this line displayed a large de novo region of homozygosity (ROH) on chromosome 3. SNP genotyping indicated that the oocyte and sperm donors were unrelated to HDFs, NT-ESCs and iPSCs (88.859-88.987% similarity). Finally, we verified the first-degree genetic relationships between two IVF-ESC lines and both the oocyte and sperm donors (92.554-94.23% similarity).

Based on the sequencing data within the D-loop hypervariable region of the mitochondrial genome (mtDNA), the mtDNA in NT-ESCs was largely oocyte-derived. Here, using whole genome bisulfite sequencing (MethylC-Seq) and transcriptome sequencing (RNA-Seq), it was shown that, as expected, the entire mitochondrial genome in all four NT-ESC lines and two IVF-ESCs was nearly identical, which was an expected outcome, as all the oocytes were provided by the same donor. However, the mtDNA sequences of these lines differed at 13 nucleotide positions when compared to HDFs or iPSCs, a result that was confirmed by conventional Sanger sequencing. The NT4 cell line showed C/T heteroplasmy at mtDNA position 16092, while the other NT-ESC and IVF-ESC lines contained a homoplasmic C allele. RNA-Seq analysis also detected a small amount of mtDNA carryover from the HDF in 3 out of 4 NT-ESC lines, ranging from 1% to 4.9%. Quantification was based on the relative number of oocyte- and HDF-specific reads at informative SNPs and the results were consistent with heteroplasmy measurements in NT-ESCs performed by ARMS-qPCR.

Subchromosomal Genetic Aberrations:

To detect de novo genetic aberrations arising during reprogramming, we compared high-throughput SNP genotyping from early passage iPSCs and NT-ESCs (passage 5-6) to HDFs, thereby allowing the recognition and removal of pre-existing aberrations. A total of thirteen de novo CNVs ranging in size from 6 to 52,696 kb were identified including ten in iPSCs and three in NT-ESCs. NT3 carried a one-copy deletion on chromosome 16 and NT4 had two duplications, one each on chromosome 3 and 6. No CNV abnormalities were detected in NT1 and NT2. Multiple CNVs were identified in four iPSC lines; iPS-S1 harbored two duplications on chromosomes 1 and 5, iPS-S2 had three one-copy deletions on chromosomes 1, 4 and 17, and iPS-S3 carried a single one-copy deletion on chromosome 10. Line iPS-R1 displayed two duplications on chromosomes 3 and 4, one large ROH encompassing most of the short arm of chromosome 3 and one two-copy deletion within the ROH. As indicated above, loss-of-heterozygosity in this region of chromosome 3 was also confirmed by independent STR analysis. No CNV abnormalities were detected in iPS-S4, iPS-S5 and iPS-R2. All CNVs detected by SNP genotyping analysis were validated using normalized RNA-Seq read counts qPCR or STR analysis. In comparing IVF-ESCs to oocyte and sperm donor DNA (Ben-Yosef D et al, Cell Reports 4, 1288-1302 (2013); incorporated by reference herein), a single one-copy deletion on the X chromosome was identified in hESO-7.

To further evaluate genetic stability, SNP genotyping was performed on a second group of matched samples, consisting of two NT-ESC lines (Leigh-NT1 and Leigh-NT2) derived from a patient with Leigh syndrome, and three matched Sendai iPSC lines (Leigh-iPS1, Leigh-iPS2, and Leigh-iPS3). Cytogenetic G-banding analysis demonstrated that all but one of the Leigh cell lines retained a diploid male karyotype with no detectable numerical or chromosomal abnormalities. Leigh-NT2 had a tetraploid karyotype, and was therefore excluded from further analysis. STR genotyping corroborated that Leigh-NT1 and the three Leigh-iPSC lines were genetically matched to the parental fibroblasts. It was also confirmed that Leigh-NT1 carried oocyte mtDNA while all Leigh-iPSCs inherited the Leigh-fib mitochondrial genome including the homoplasmic m.8993T→G mutation (Taylor R W and Turnbull D M, Nature Rev Genet 6, 389-402 (2005); incorporated by reference herein. A total of nine de novo CNVs were identified in Leigh cell lines, including multiple CNVs in Leigh-iPS1 and -iPS3 and one each in Leigh-iPS2 and Leigh-NT1.

Based on the total number of CNVs detected, it was calculated that iPSCs (ten cell lines), NT-ESCs (5 cell lines) and IVF-ESCs (2 cell lines) carried an average of 1.8, 0.8 and 0.5 CNVs per cell line, respectively. No significant differences were found among pluripotent stem cell types. The InDel analysis of RNA-Seq data from the same set of human pluripotent stem cell lines also indicated that NT-ESC lines had fewer InDels compared to the iPSC lines, but the difference was not significant. However, these results are consistent with a previous report that iPSCs, on average, carry 2 de novo CNVs per line (Abyzov A, Nature 492, 438-442 (2012); incorporated by reference herein). None of the identified CNVs were shared among cell lines. In addition, there was not a higher average incidence of genomic aberrations in the retrovirus-derived iPSC lines relative to the non-integrating Sendai virus-induced iPSCs.

Since the NT-ESCs and the iPSCs were generated from the same somatic cells and did not contain statistically significant different numbers of CNVs, it appears that the mutagenic and selective pressures present in transcription factor-based and SCNT-based reprogramming are similar in magnitude.

Figure 15A:
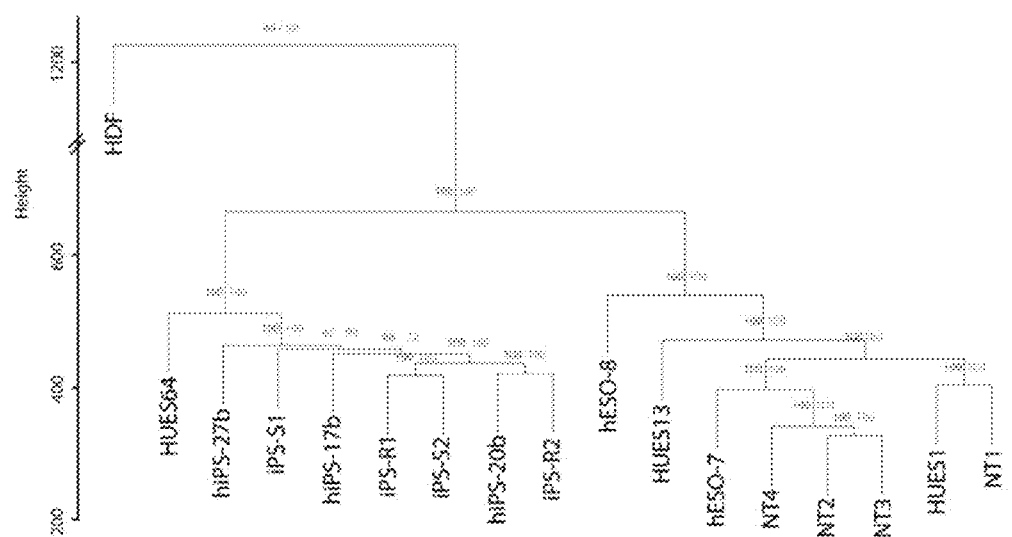
FIG. 15A is a representation of an unsupervised hierarchical clustering of all filtered and normalized methylation probes in 5 IVF-ESC, 7 iPSC, and 4 NT-ESC lines, and in parental HDFs. Red and green values above each edge represent AU/BP P-Values (%) calculated using bootstrap resampling.

Global DNA Methylation:

DNA methylation is an important epigenetic mechanism contributing to cell identity. Significant DNA methylation differences between iPSCs and IVF-ESCs have been reported, as well as differences among iPSC lines (Nazor K L 2012 supra and Bock C et al, Cell 144, 439-452 (2011); incorporated by reference herein). Since such differences could reflect incomplete or abnormal reprogramming and result in altered gene expression affecting cell function, the matched stem cell lines derived from the HDF somatic cells using the were profiled using an Infinium HumanMethylation450 BeadChip® to characterize these differences on a genome-wide scale (Price M E et al, PLoS Genetics 7, e1002389 (2011); incorporated by reference herein). To determine whether global DNA methylation patterns were similar to previously reported cell lines (Ziller M J et al, PLoS Genetics 7, e1002389 (2011); incorporated by reference herein); unsupervised hierarchical clustering was performed (FIG. 15A) (Suzuki R and Shimodaira H et al, Bioinformatics 22, 1540-1542 (2006); incorporated by reference herein.)

Figures 15B, 15C:
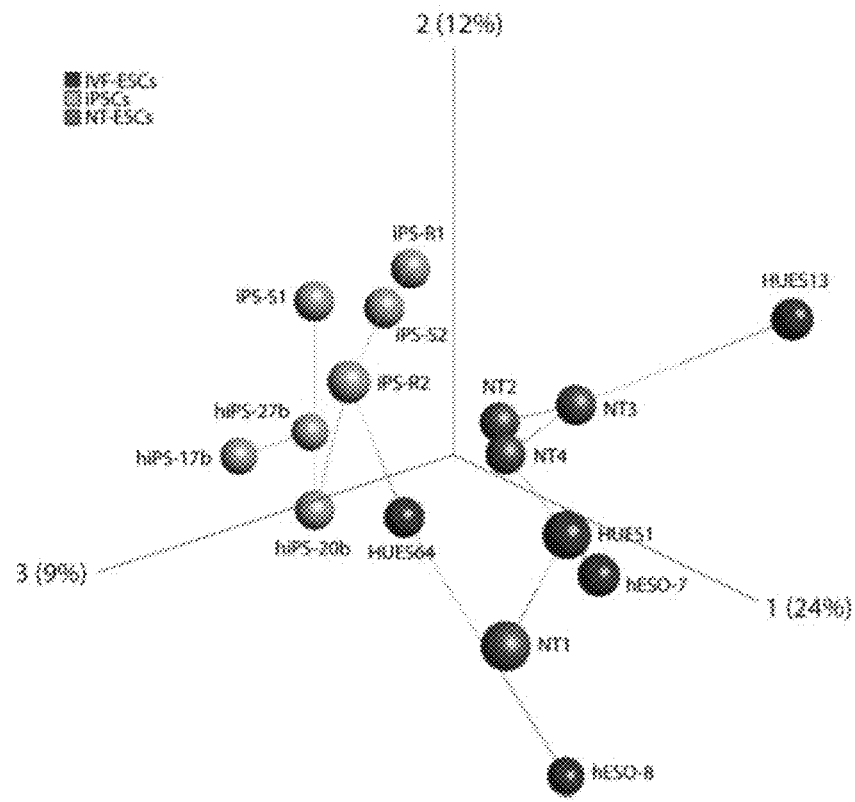
FIG. 15B is a representation of a principal component analysis of IVF-ESCs (red balls), iPSCs (yellow and orange balls), and NT-ESCs (green balls) with nearest neighbor analysis.
FIG. 15C is a table showing the total number of differentially methylated probes (DMPs) observed between matched iPSCs, NT-ESCs and IVF-ESCs (n=11). The number of DMPs shared with parental HDFs was used as a measure of the degree somatic cell memory.

Bootstrap resampling analysis revealed two well-defined clusters, one containing seven iPSC lines (including the four iPSC lines generated herein; FIG. 15B) and one IVF-ESC line (HUES64). The second cluster included four NT-ESC lines and four IVF-ESC lines (FIG. 15B). Based on this comparison, we determined that NT-ESCs clustered together with IVF-ESCs (with the exception of HUES64) while iPSCs formed a distinct group. To ensure that intra-group variability was similar between the iPSCs, NT-ESCs and IVF-ESCs the coefficient of variation (CV) was calculated for each stem cell type and compared to previously reported cell lines (iPSC=0.71, NT-ESC=0.73, IVF-ESC=0.74; Ziller et al. iPSC=0.73 and IVF-ESC=0.72,).

Comprehensive group-wise analysis revealed 6,478 differentially methylated probes (DMPs) between iPSCs and IVF-ESCs (FDR <0.01; FIG. 15C). Using the same criteria, only 110 DMPs were found between the NT-ESCs and IVF-ESCs, suggesting that in contrast to iPSCs, NT-ESCs were remarkably similar to IVF-ESCs. It was then determined whether or not the DMPs identified in iPSCs and NT-ESCs could be attributed to residual epigenetic memory inherited from HDFs. Of the 6,478 DMPs identified in iPSCs, 780 displayed a substantial difference in DNA methylation (Avg. β difference >|0.3|) both between iPSCs and IVF-ESCs and between HDFs and IVF-ESCs. Of the 110 DMPs identified in NT-ESCs, 87 were substantially different both between NT-ESCs and IVF-ESCs and between HDFs and IVF-ESCs (FIG. 15C). Functional enrichment analysis of probes that were highly methylated in iPSCs and HDFs compared to IVF-ESCs indicated association with sequence-specific DNA binding transcription factor activity (2.02 Fold Enrichment, FDR <0.0001). No significant annotation terms were found for hypermethylated probes shared by NT-ESCs and HDFs. However, probes that were hypomethylated in iPSCs, NT-ESCs and HDFs compared to IVF-ESCs were enriched for loci associated with the MHC class II protein complex (72 Fold Enrichment, FDR <0.001).

Based on these results, it can be concluded that methylation profiles of NT-ESCs are much more similar to IVF-ESCs than to iPSCs. Both NT-ESCs and iPSCs do show evidence of residual HDF epigenetic memory, but iPSCs carry approximately 8-fold more of such sites. Interestingly, nearly 80% of DMPs in NT-ESCs, but only 12% in iPSCs, could be related to somatic epigenetic memory, suggesting that the majority of methylation abnormalities in iPSCs resulted from reprogramming errors.

Figure 16A:
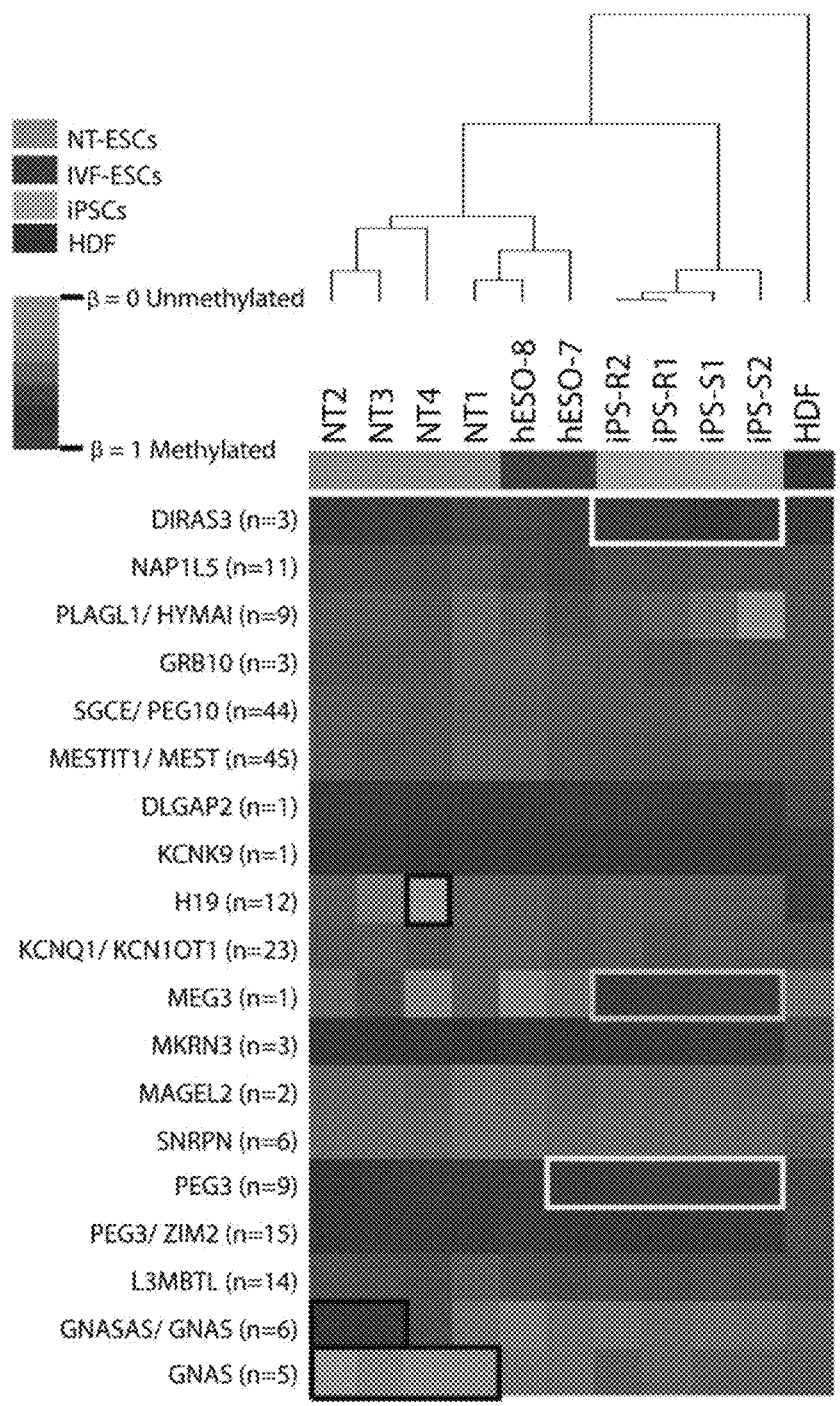
FIG. 16A is a heat map of previously identified imprinted regions. For each gene, an average β-value for all methylation probes assigned to a specific gene is shown and the number of included probes is indicated next to the gene. White box: hypermethylation at DIRAS3 locus, no change in gene expression; black boxes: DNA methylation changes at H19, GNASAS/GNAS, and GNAS loci, no change in gene expression; grey box: hypermethylation at the MEG3 locus, reduced gene expression; yellow box: hypermethylation at the PEG3 locus, reduced gene expression.
Figure 16B:
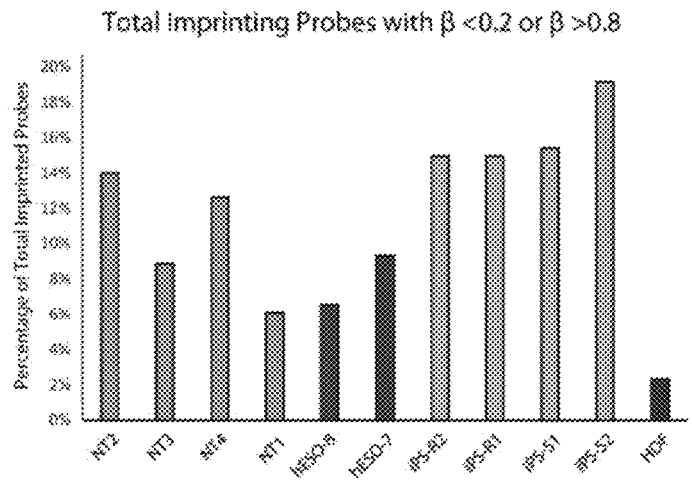
FIG. 16B is a bar graph showing percentage of total imprinted probes that had a $\beta<0.2$ or $\beta>0.8$.

Aberrant DNA Methylation at Imprinted Regions:

Imprinting is a form of epigenetic regulation that controls the expression of distinct regions of the genome in a parent-of-origin-specific manner. Aberrant methylation of CpG dinucleotides at imprinted loci has been observed in iPSCs and in some IVF-ESCs (Nazor K L et al 2012 supra; Stelzer Y et al, *Stem Cell Reports* 1, 79-89 (2013); and Rugg-Gunn P J et al, *Human Mol Genet* 16, R243-R251 (2007); all of which are incorporated by reference herein). Therefore, previously identified imprinted regions were analyzed (de Hoon M J et al, *Bioinformatics* 20, 1453-1454 (2004) and Saldanha, *Bioinformatics* 20, 3246-3248 (2004); both of which are incorporated by reference herein.) (FIG. 16A) For imprinted regions, CpG dinucleotides with a β value between 0.2 and 0.8 on the DNA methylation microarray were considered to be partially methylated, as one would expect. Imprinted regions with β values above 0.8 were considered to be aberrantly hypermethylated, and those below 0.2 were hypomethylated. It was first determined if the variance of the cell lines was comparable to other independently generated cells within the previously identified imprinted regions based on CV calculations. The CVs for the SCNT lines described herein ranged from 0.27-0.36 whereas the lines described in Ziller et al, 2011 supra ranged from 0.28-0.40. Unsupervised hierarchical clustering within imprinted regions showed that NT-ESC lines clustered more closely with control IVF-ESCs and displayed a lower percentage of aberrantly methylated probes compared to iPSCs (Avg. percent of total imprinted probes aberrantly methylated in iPSCs=16.1%, NT-ESCs=10.4% and IVF-ESCs=7.9%; FIG. 16B). Several loci (DLGAP2, KCNK9, MKRN3) were hypermethylated in all three pluripotent stem cell types. However, differential expression of the associated genes was not observed at these loci.

NT-ESC-specific DNA methylation differences were also noted. All NT-ESCs displayed hypomethylation at the GNAS locus, while the NT2 and NT3 lines were hypermethylated at the GNASAS/GNAS locus, and NT4 was hypomethylated at the H19 locus (black boxes in FIG. 16A). The hypomethylation of NT4 at H19 corresponded with biallelic expression of this gene.

Figure 16C:
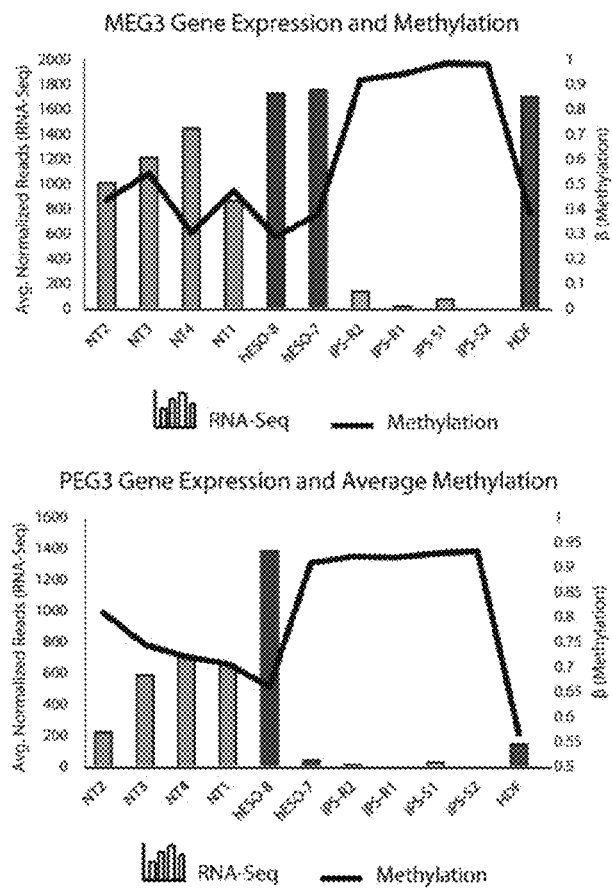
FIG. 16C is a set of two bar/line graphs showing the normalized RNA-Seq read count (bars, averaged between replicates) and the methylation $\beta$-values (black line) for MEG3 and PEG3.

All iPSC lines and hESO-7 displayed hypermethylated CpGs at the PEG3 locus (yellow box in FIG. 16A) while only the iPSC lines displayed hypermethylated CpGs at the MEG3 locus (gray box in FIG. 2A) This hypermethylation was associated with reduced expression of the corresponding transcripts (black line on graphs in FIG. 16C; MEG3 adjusted P-Val <0.001, Avg. Fold Change 19.8; PEG3 Adjusted P-Val <0.005, Avg. Fold Change 128.9; see colored bars on the histogram). The DIRAS3 locus was also hypermethylated in all iPSCs, but was not correlated with a change in gene expression (white box in FIG. 16A).

DNA methylation abnormalities at imprinted loci associated with changes in gene expression were more frequent in iPSCs. In contrast, DNA methylation profiles in NT-ESCs were more similar to IVF-ESC controls, suggesting more faithful reprogramming and better maintenance of imprinting marks.

DNA Methylation at X-Chromosome Inactivated Sites:

X chromosome inactivation (XCI) results in monoallelic transcriptional silencing of genes on one of the X chromosomes in female cells, thus providing X chromosome dosage compensation between males and females (reviewed in Lee J T and Bartolomei M S, *Cell* 152, 1308-1323 (2013); incorporated by reference herein). Evidence of XCI can be detected by allele specific expression and X chromosome coating by the long noncoding RNAs XIST and XACT) Silva S S et al, *Proc Natl Acad Sci USA* 105, 4820-4825 (2008) and Vallot C et al, *Nature Genet* 45, 239-241 (2013); both of which are incorporated by reference herein). The majority of human female IVF-ESCs display evidence of XCI (Shen Y et. al., *Proc Natl Acad Sci USA* 105, 4709-4714 (2008) and Tchieu J et al, *Cell Stem Cell* 7, 329-342 (2010); incorporated by reference herein), with few exceptions Hanna J et al, *Proc Natl Acad Sci USA* 107, 9222-9227 (2010) and Marchetto M C et al, *Cell* 143, 527-539 (2010); both of which are incorporated by reference herein). Based on RNA-Seq, it was determined that all ten female pluripotent stem cell lines and HDFs expressed similar levels of XIST, but only the pluripotent cells expressed XACT.

Figure 17A:
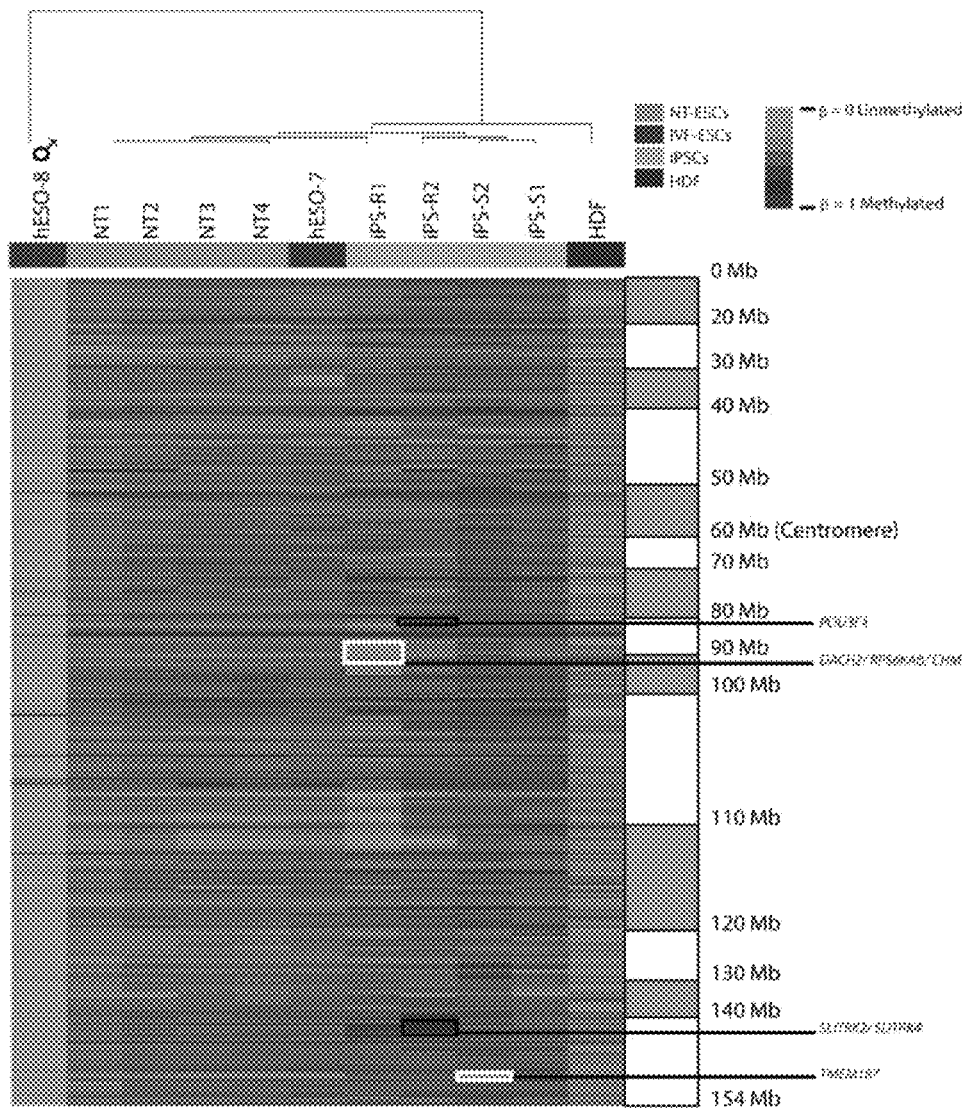
FIG. 17A is a heat map displaying $\beta$-values of previously identified XCI probes on the methylation array in NT-ESCs, IVF-ESCs, iPSCs, and HDFs. The genes highlighted with black boxes showed both aberrant hypermethylation and gene expression alteration. The hypomethylated genes highlighted in white boxes were associated with gene expression alteration.
Figure 17B:
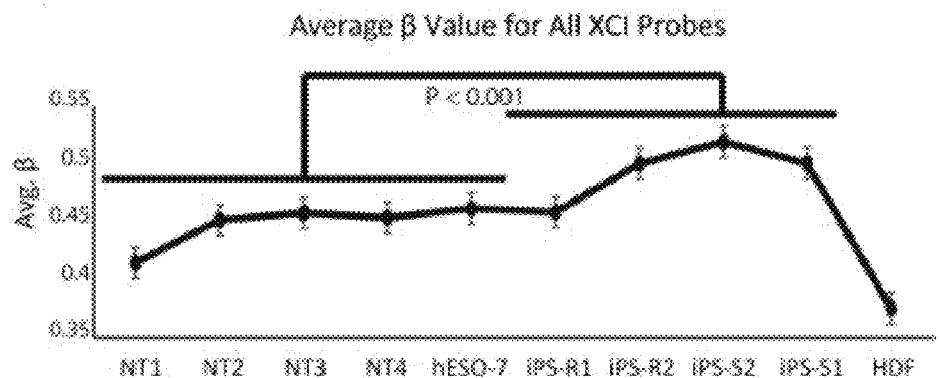
FIG. 17B is a Line graph showing an average $\beta$-value for all XCI probes for each cell line (Two-sided t-test P<0.001, error bars=s.e.m.).
Figure 17C:
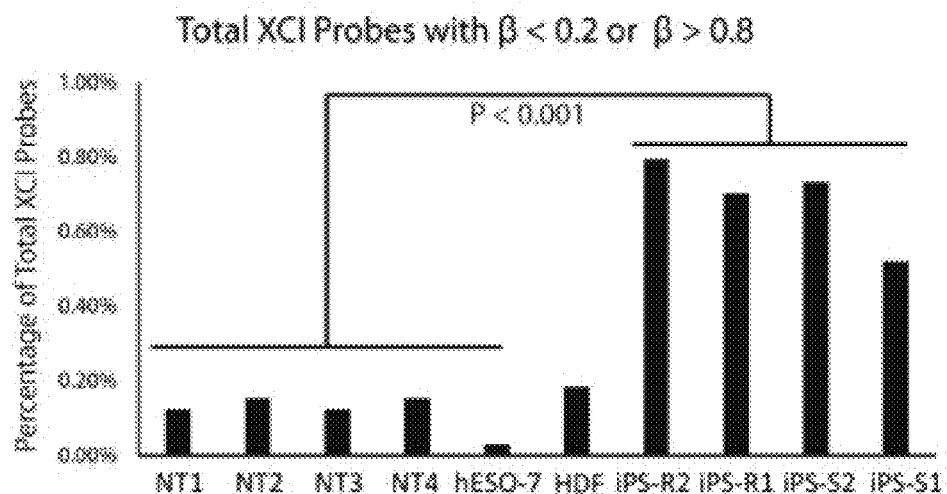
FIG. 17C is a bar graph showing the percentage of total XCI probes with ($\beta<0.2$ or $\beta>0.8$ (Two-sided t-test P<0.001).

DNA methylation differences between stem cell types at previously annotated XCI loci were assessed. As expected, the X chromosome heatmap profile for the male line, hESO-8, was universally unmethylated (FIG. 17A). β values for most of these loci for all female stem cell lines and the somatic HDFs were between 0.2 and 0.8, consistent with partial methylation, as expected in regions of XCI. NT-ESCs and IVF-ESCs demonstrated, on average, higher levels of DNA methylation at XCI loci compared to parental HDFs, while methylation levels in iPSC lines were markedly and significantly higher than in NT-ESCs and female hESO-7 (P-Value <0.001; FIG. 17B), with substantial variation among lines. When aberrant methylation was defined as β<0.2 or >0.8, all NT lines and hESO-7 had 4-fold fewer XCI methylation aberrations compared to iPSCs (P-Value <0.001; FIG. 3c).

It was also examined whether aberrant DNA methylation at XCI sites was associated with alterations in gene expression. RNA-Seq demonstrated that hypermethylation of POU3F4, SLITRK2 and SLITRK4 in the iPS-R2 line corresponded to lower levels of gene expression (black boxes in FIG. 17A), indicating that the relative genetic stability (no CNVs) of this cell line did not correlate with epigenetic integrity. In addition, hypomethylation of DACH2, RPS6KA6 and CHM in iPS-R1 and TMEM187 in iPS-S2 correlated with increased gene expression (white boxes in FIG. 17A). Aberrant DNA methylation associated with alterations in gene expression of tumor associated genes, such as the SLITRK gene family (Aruga J et al, *Gene* 315, 87-94 (2003); incorporated by reference herein), emphasizes the need for thorough quality-control measures on stem cells destined for clinical use.

DNA Methylation at Autosomal Non-Imprinted Loci:

DNA methylation analysis of autosomal non-imprinted CpG and non-CpG sites using the Kruskal-Wallis test revealed 1,621 DMPs among NT-ESCs, iPSCs and IVF-ESCs (P-Value <0.01, Δβ>0.5). We grouped these probes into six major clusters using an unsupervised self-organizing map algorithm (Newman A M and Cooper J B, BMC Bioinformatics 11, 117 (2010); incorporated by reference herein). All six clusters were analyzed for cis-regulatory functional enrichments using GREAT (McLean C Y et al, Nature Biotechnol 28, 495-501 (2010); incorporated by reference herein), but only Cluster 3 showed significant enrichments for categories associated with morphogenesis and neural development iPSCs displayed higher DNA methylation levels compared to NT-ESCs and IVF-ESCs for most clusters, with the exception of Cluster 4. NT-ESCs displayed an intermediate DNA methylation pattern between iPSCs and IVF-ESCs, but were overall closer to IVF-ESCs.

Several different probe subsets were examined. Higher methylation levels among iPSC lines compared to IVF-ESC lines were observed, consistent with previous reports (Nishino K et al, PLoS Genetics, 7, e1002085 (2011); and Polo J M et al, Nat Biotech 28, 848-855 (2010); both of which are incorporated by reference herein.) The examined subsets included: probes located within −2000 bp of the transcription start site (TSS); CpG islands (CGI); 5' and 3' regions (0-2 kb from CGI and 2-4 kb from CGI)(Doi A et al, Nature Genet 41, 1350-1353 (2009) and Irizarry R A et al, Nat Genet 41, 178-186 (2009); both of which are incorporated by reference herein); FANTOM 4 promoters with low and high CpG content (http://fantom.gsc.riken.jp/4/); predicted enhancers (Consortium E P et al, Nature 447, 799-816 (2007); Heintzman N D et al, Nature Genet 39, 311-318 (2007); and Heintzman N D et al, Nature 459, 108-112 (2009); all of which are incorporated by reference herein); major histocompatibility complex regions (Tomazou E M et al, BMC Med Genom 1, 19 (2008); incorporated by reference herein); C-DMRs (cancer-related DMRs) and R-DMRs (reprogramming-related DMRs); and repetitive elements. The largest difference between iPSCs and NT/IVF-ESCs was apparent in R-DMRs, where iPSCs were very similar to parental HDFs. This finding is surprising, as R-DMRs were previously reported to be differentially methylated between iPSCs and fibroblasts.

Figure 18A:
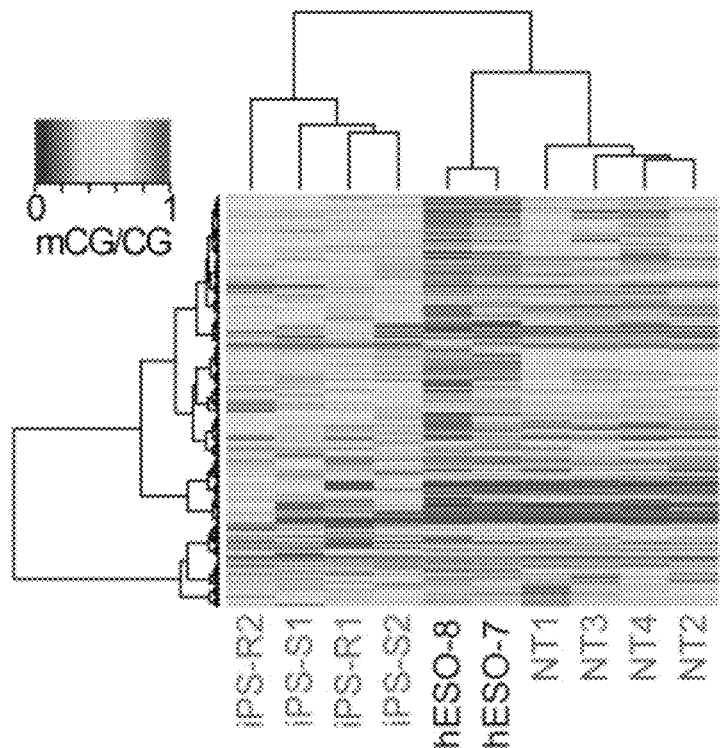
FIG. 18A is a complete hierarchical clustering of CG methylation for a total 678 CG-DMRs identified by comparing methylomes of NT-ESCs and iPSCs to IVF-ESCs methylomes.
Figure 18B:
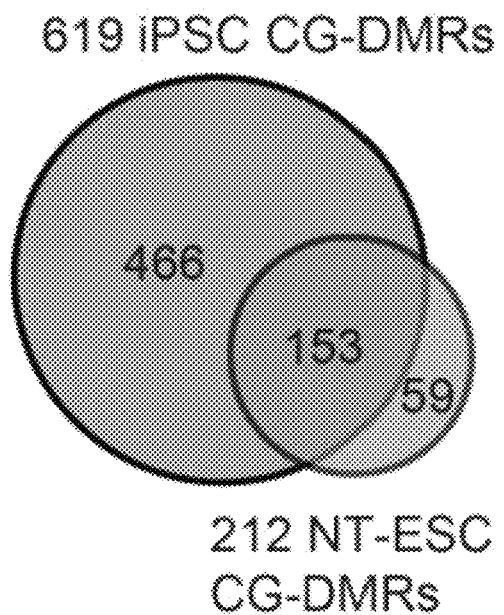
FIG. 18B is a Venn diagram showing the overlap of CG-DMRs across iPSCs and NT-ESCs in cases where the DMR is found in at least one of the lines in the same group.
Figure 18C:
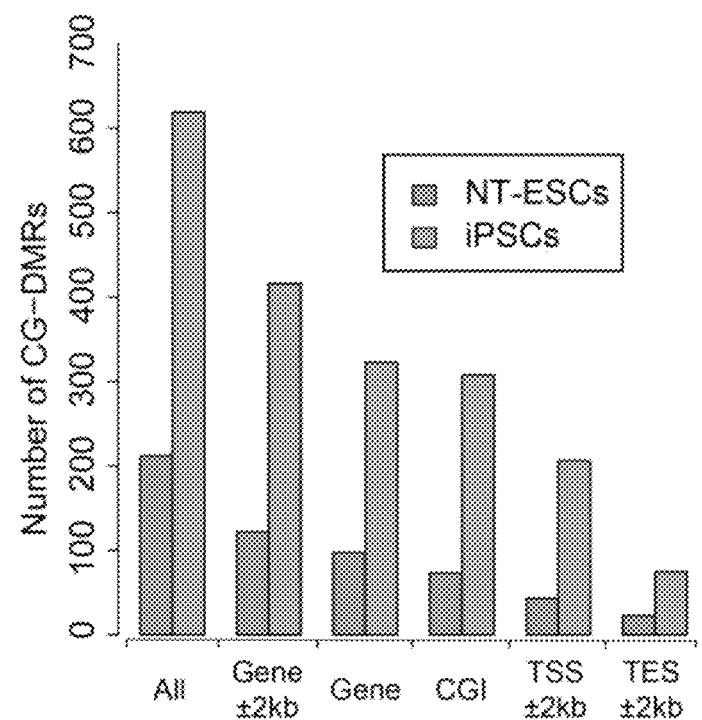
FIG. 18C is a bar graph showing the number of 678 CG-DMRs overlapped (1 bp) with indicated genomic features—CGI, CG islands; TSS, transcription start sites; TES, transcription end sites.
Figure 18D:
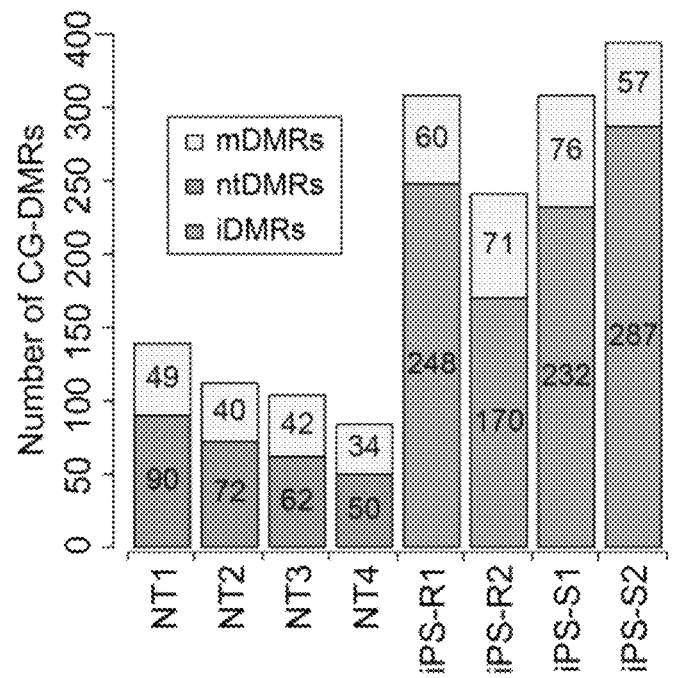
FIG. 18D is a bar graph showing the distribution of CG-DMRs among each NT-ESC and iPSC line. DMRs that were also shared with parental somatic cells were identified as memory or mDMRs. ntDMRs—NT-specific and iDMRs-iPSC-specific.

Aberrant Reprogramming of CG Methylation Detected by Whole Genome Bisulfite Sequencing:

To gain a more detailed picture of the underlying methylation differences between the NT-ESC and iPSC lines, high-coverage base-resolution methylomes of the matched HDF-derived stem cell lines and IVF-ESC controls (coverage ranged from 14× to 25×) were generated using MethylC-Seq. The data were then compared to existing whole methylome data from three additional IVF-ESC lines (H1, H9 and HUES6) described in earlier publications Xie W et al, Cell 153, 1134-1148 (2013); Laurent L et al, Genome Res 20, 320-331 (2010); and Lister R et al, Science 341, 1237905 (2013); all of which are incorporated by reference herein). Hierarchical clustering of the methylation level at CG-DMRs demonstrated that the CG methylation landscape of NT-ESCs more closely resembled that of the IVF-ESCs compared to the iPSCs (FIG. 18A). By comparing the methylomes of all IVF-ESCs, NT-ESCs, iPSCs and filtering regions that were obscure in methylation pattern or highly variable in IVF-ESCs, a total of 678 CG-DMRs were identified that were present in at least one NT-ESC or iPSC line but not in IVF-ESCs (FDR=0.01, also see methods). The majority of these CG-DMRs were identified within iPSCs (619), while NT-ESCs contained 3-fold fewer (212). A total of 153 CG-DMRs were shared between both cell types (FIG. 18B). Using similar CG-DMR screening approach it was calculated that five iPSC lines previously profiled carried a total of 792 CG-DMR suggesting that both iPSC groups are comparable. Detailed analysis revealed that most of these CG-DMRs were localized within CG islands and gene bodies (FIG. 18C). Analysis of CG-DMR distribution among individual cell lines showed that each NT-ESC line had fewer aberrant CG methylation regions than any of the iPSC lines, again implying that the NT-ESCs were more similar to controls (FIG. 18D, p-value=0.0147, Mann-Whitney test). CG-DMRs were then assigned into three groups: memory DMRs (mDMRs) that were shared with HDFs; NT-specific (ntDMRs) and iPSC-specific DMRs (iDMRs). Comparing the number of mDMRs and cell specific DMRs, it was found that on average, 38% of total CG-DMRs in the NT-ESC lines were of somatic memory origin while 22% of DMRs in iPSCs were of somatic memory origin (FIG. 4D).

Figure 18E:
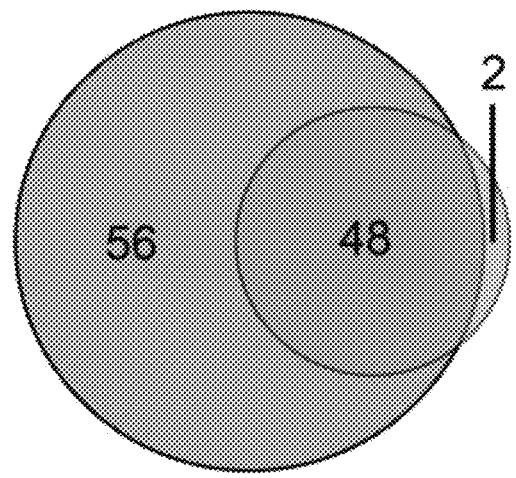
FIG. 18E is a Venn diagram showing the hotspot CG-DMRs that were identified in every iPSC or NT-ESC line in the same group. 48 hotspot CG-DMRs were shared among all iPSC and NT-ESC lines.

Inspection of the recurrent CG-DMRs (hotspot DMRs) that were identified in every iPSC or NT-ESC line revealed that the four NT-ESC lines had 50 hotspot DMRs, which was 2-fold less than the 104 hotspot DMRs present in all four iPSC lines (FIG. 18E). Interestingly, 48 of 50 hotspot DMRs identified among NT-ESCs were also shared with iPSCs (p-value <0.001, Hypergeometric test). Further analysis of these hotspot DMRs shared among all 8 cell lines revealed that 63% (30 out of 48) were mDMRs. This suggests that most hotspot DMRs common to both NT-ESCs and iPSCs represent regions resistant to reprogramming by either approach. Only 2 out of 50 (4%) hotspot DMRs were unique to NT-ESCs compared to 56 out of 104 (54%) iPSCs specific hotspots (FIG. 18E). This implies that SCNT is associated with fewer de novo aberrant CG methylation events compared to the iPSC reprogramming method.

Figure 19A:
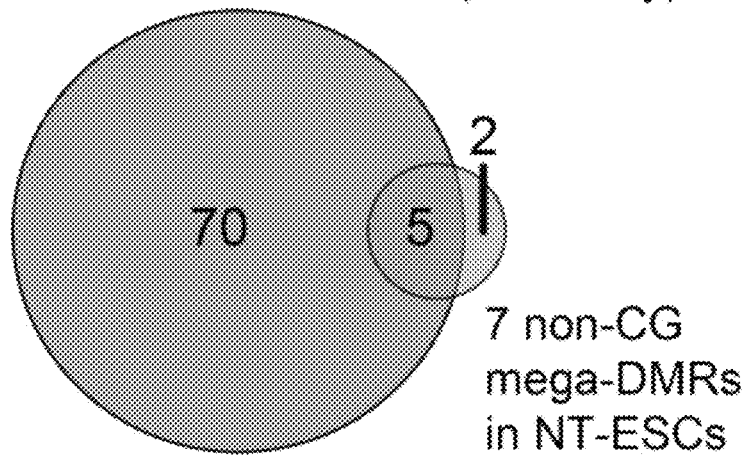
FIG. 19A is a Venn diagram showing the overlap of the 77 non-CG mega-DMRs identified in the iPSC and the NT-ESC lines disclosed herein. Numbers within circles denote DMRs identified exclusively within each group. Five DMRs were shared among all cell lines in both groups.
Figure 19B:
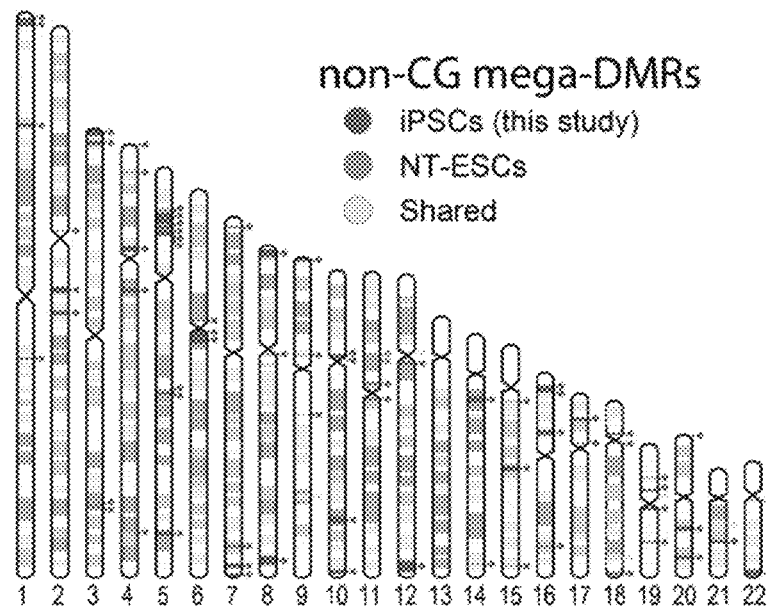
FIG. 19B is a chromosome ideogram showing the location of the 77 non-CG mega-DMRs found in both NT-ESC and iPSC lines from this study. Orange circles and lines indicate the location of the individual DMRs specific for iPSCs; green circles and lines denote those specific for NT-ESCs and yellow circles and lines are DMRs shared by both cell types.

NT-ESCs Display Less Aberrant Non-CG Methylation than iPSCs:

Pervasive and exclusive non-CG methylation has been identified in pluripotent stem cells compared to fibroblasts. In addition, iPSCs carry frequent aberrant non-CG methylation in megabase-scale regions. Herein it is demonstrated that the only regions on the methylation array at which iPSCs were consistently hypomethylated compared to NT/IVF-ESCs were the non-CpG sites, including "mega-DMRs" (FIG. 19A and FIG. 19B). At the 110 non-CpG sites in mega-DMRs interrogated by the Infinium HumanMethylation450 BeadChip®, iPSCs were significantly hypomethylated compared to IVF-ESCs (P<0.001, Mann-Whitney test), whereas there was no significant difference between NT-ESCs and IVF-ESCs. Since non-CpG methylation is markedly more prevalent in pluripotent cells compared to fibroblasts, these results are consistent with the notion that SCNT results in more complete reprogramming than does standard transcription factor-based reprogramming.

Figure 19C:
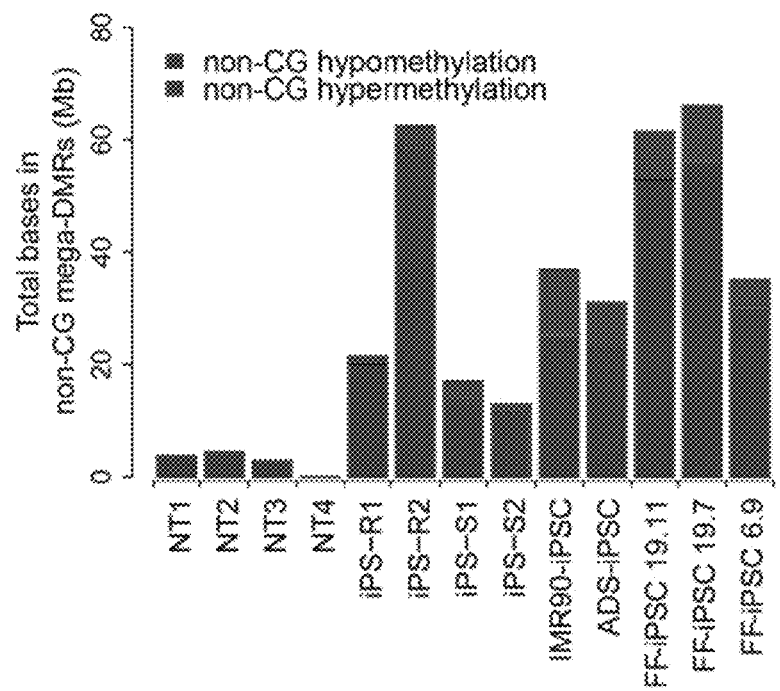
FIG. 19C is a bar graph showing the total length of the non-CG mega-DMRs identified in 4 NT-ESC, and 9 iPSC lines. The NT-ESCs had a significantly lower size of DMRs (Mann-Whitney test, P<0.005) compared to the iPSCs.
Figure 19D:
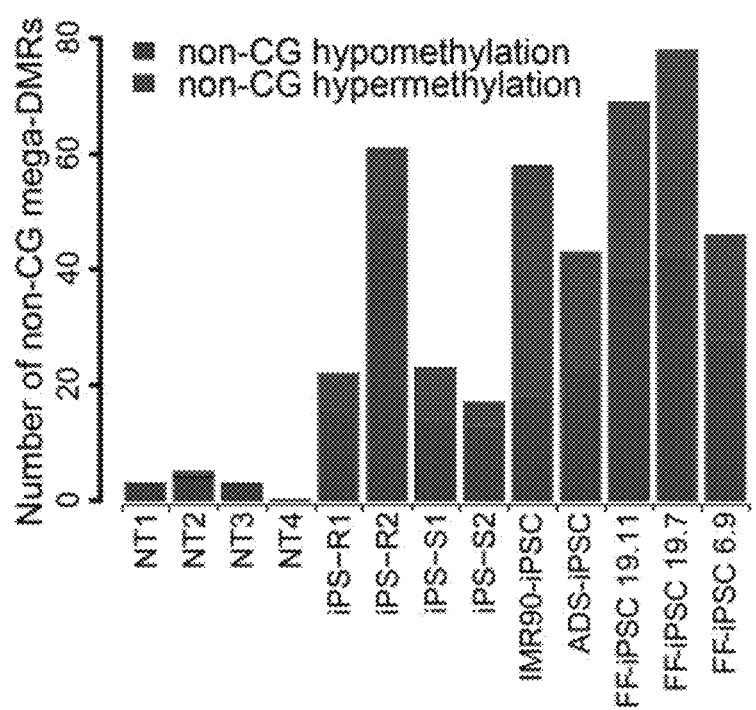
FIG. 19D is a bar graph showing the total number of the non-CG mega-DMRs identified in the cell lines. The NT-ESCs had a significantly lower number of DMRs (Mann-Whitney test, P<0.005) compared to the iPSCs.

To investigate the extent of non-CG methylation in more detail, regions showing large-scale non-CG methylation differences in the reprogrammed cell lines when compared to IVF-ESC were systematically identified. Five IVF-ESC lines served as the gold standard methylation landscape for pluripotent stem cells. A total of 150 autosomal non-CG mega-DMRs were identified when the methylomes of the four NT-ESCs nine iPSCs were compared to controls. Non-CG mega-DMRs linked to the sex chromosomes were excluded from this study due to the mixed gender of the five IVF-ESC controls. These non-CG mega-DMRs covered 123 Mb of genome and included all of the regions reported in the previous study (99% of bases). Of the total 150 non-CG mega-DMRs identified in the combined dataset, 77 were identified in both NT-ESCs and iPSCs from this study, of which 75 occurred exclusively in iPSCs (FIG. 19A). These DMRs were distributed on every autosomal chromosome except chromosome 13 (FIG. 19B). Only 7 non-CG mega-DMRs (10-fold less) were present in NT-ESCs and were localized on four chromosomes (FIG. 19A and FIG. 19B). Non-CG mega-DMRs were shown to be significantly closer to centromeric and telomeric regions compared with shuffled non-CG mega-DMRs (FIG. 19B, p-value <0.001). Several different patterns of aberrant non-CG methylation were observed including hypomethylation in iPSCs only, hypomethylation in both NT-ESCs and iPSCs, and hypermethylation in iPSCs only. However, the vast majority of non-CG mega-DMRs (79.6%, or 92.5% of total bases) were hypomethylated in iPSCs and/or NT-ESCs compared with IVF-ESCs (FIG. 19C).

iPSCs described herein were determined to similar to other iPSCs when compared to iPSC lines generated previously. The four iPSC lines from this study contained a total of 75 DMRs, while the five iPSC lines generated earlier carried 121 non-CG mega-DMRs. This indicates that despite different somatic cell origins and possible culture differences in different laboratories, iPSC lines carry similar levels of aberrant non-CG methylation. In contrast, the NT-ESCs showed less aberrant non-CG methylation compared to all iPSCs (FIG. 19C and FIG. 19D, p-value <0.005, Mann-Whitney test). Hierarchical clustering of the iPSC and NT-ESCs by non-CG methylation state for all non-CG mega-DMRs also supported the conclusion that the NT-ESCs are more similar to IVF-ESCs than the iPSCs.

To understand the functional impact of non-CG mega-DMRs, transcriptional activity within those regions was examined. On average, 2 genes in NT-ESCs and 30 in iPSCs were located within non-CG mega DMRs, implying that fewer genes in NT-ESCs are under potential disruption by methylation (p-value=0.0147, Mann-Whitney test). GO analysis (Gore A et al, Nature 471, 63-67 (2011); incorporated by reference herein) for genes in hypomethylated non-CG DMRs revealed that these genes were enriched in categories related to olfactory transduction, epidermal cell differentiation, cytoskeleton, Immunoglobulin and Homeobox protein (FDR ≤0.001). Gene expression in the iPSCs for 2 genes in the hypermethylated non-CG mega-DMRs was upregulated whereas expression of 24 genes in the iPSCs and 6 genes in the NT-ESCs in the hypomethylated non-CG mega-DMRs was down regulated, consistent with previous findings (p-value <0.001). Taken together, these observations indicate that in non-CG methylation regions, NT-ESCs were more faithfully reprogrammed to a state that more closely resembled that of the gold standard IVF-ESCs compared to the iPSCs. Among the NT-ESCs, NT4 had the least aberrant methylations in both CG and non-CG contexts.

Figure 20A:
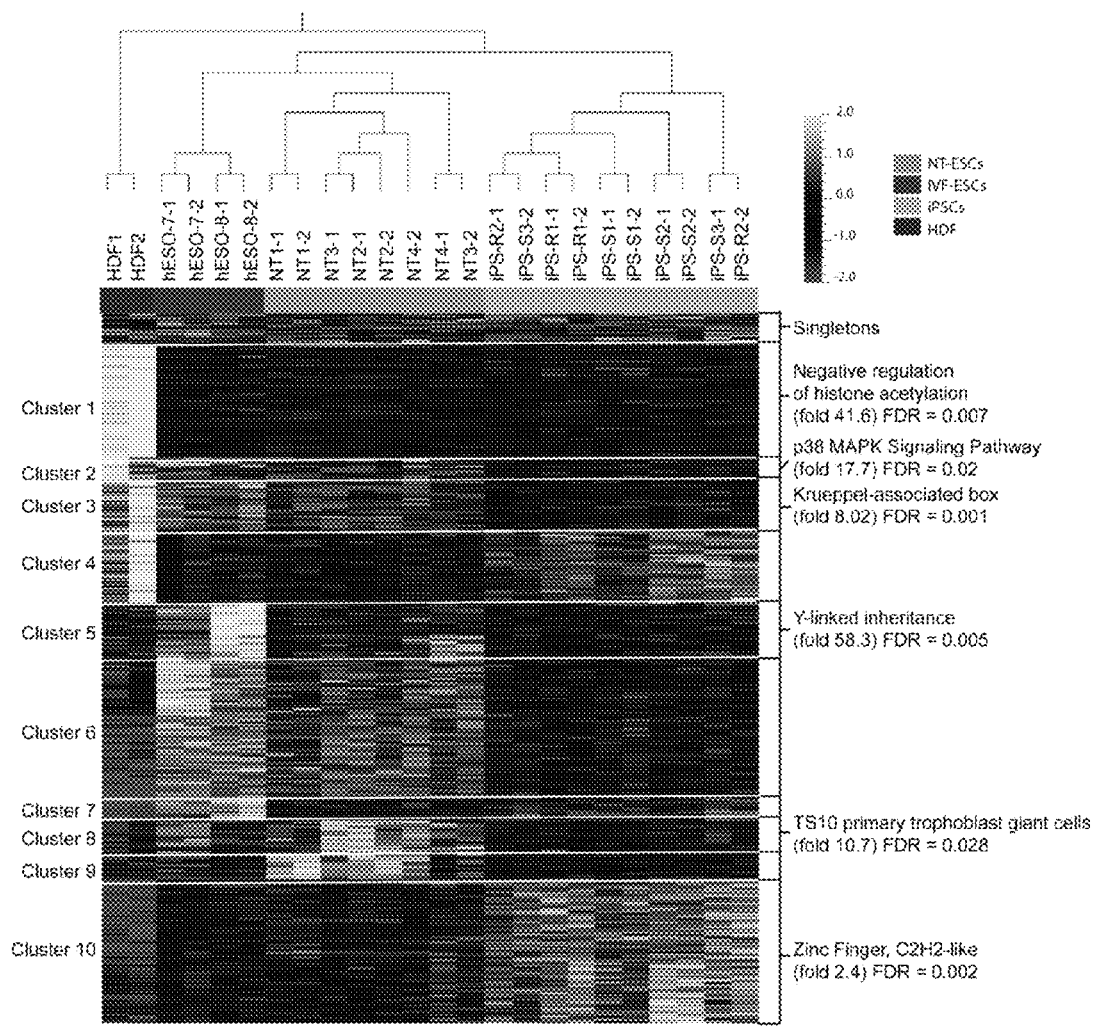
FIG. 20A is a heat map displaying 1220 differentially expressed genes between NT-ESCs, iPSCs and IVF-ESCs (n=22) (ANOVA adjusted p-value <0.05). Genes were clustered into ten groups for functional analysis and presented as a heat map (on the right). Cluster 4, 6, 7, and 9 showed no significant functional enrichments.

Global Gene Expression:

Lastly global gene expression patterns from strand-specific RNA-Seq were compared. Consistent with DNA methylation, intra-group variability was similar among the three pluripotent cell types (CVs: NT-ESC=1.41, IVF-ESC=1.45, IPSC=1.44) and unsupervised hierarchical clustering with bootstrap resampling indicated that, in contrast to iPSCs, NT-ESCs clustered closely with IVF-ESCs (FIG. 20A). Differential expression analysis (FDR<0.05) among the pluripotent stem cell types yielded 1220925 transcripts, which were grouped into 10 clusters by unsupervised clustering. The majority (65%) of these genes were either significantly up- or down-regulated in iPSCs compared to NT-ESCs and IVF-ESCs. Clusters 2 and 3 showed higher gene expression in NT-ESCs and IVF-ESCs compared to iPSCs. When subjected to functional enrichment analysis, these clusters were associated with p38 MAPK signaling pathway ((FDR=0.02; n=51) and Krueppel-associated box genes (FDR=0.001; n=91), respectively. Cluster 10 contained transcripts that were up-regulated in IVF-ESCs compared to both NT-ESCs and iPSCs. This cluster included genes associated with Zinc Finger and C2H2-like genes (FDR=0.002; n=227). Transcripts in Cluster 8 were enriched for MGI expression of TS10 primary trophoblast giant cells (FDR=0.03; n=46). Genes in cluster 5, associated with Y-linked inheritance, were up-regulated in one pair of male IVF-ESCs.

Figure 20B:
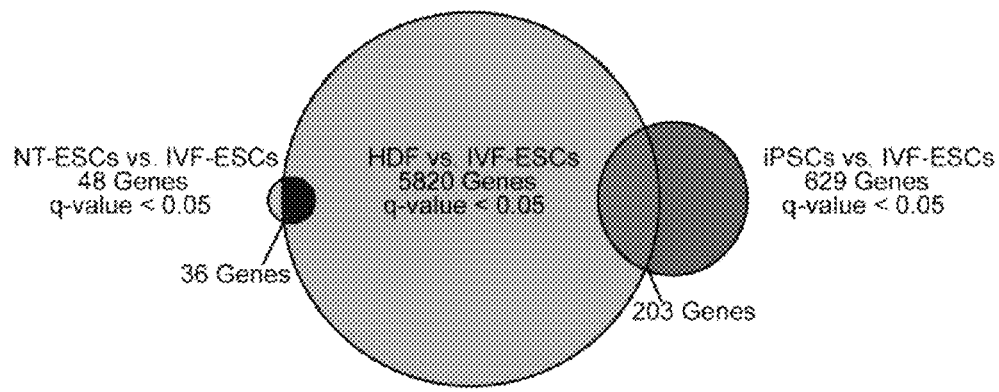
FIG. 20B is a Venn diagram showing the number of genes differentially expressed between the HDF and the IVF-ESCs (large circle), the iPSCs and the IVF-ESCs (medium circle) and the NT-ESCs and IVF-ESCs (slam circle; t-test FDR <0.05). Overlapping regions represent the number of genes differentially expressed in both the HDF and either the NT-ESCs or iPSCs.

Based on the differential expression analysis results (FIG. 20A), evidence of transcriptional memory was observed. To find which genes displayed transcriptional memory in both our iPSC lines and NT-ESC lines, three separate t-tests were conducted between the HDF samples and the IVF-ESC lines, the NT-ESC lines and the IVF-ESC lines and the iPSC lines and the IVF-ESC lines at a FDR cutoff of 0.05. Genes that were differentially expressed in both the HDFs and NT-ESCs or iPSC lines were also identified. A total of 24 genes were expressed at significantly lower levels in the NT-ESCs and HDFs compared to IVF-ESCs. These represented genes that were potentially incompletely reactivated during reprogramming. A total of 12 genes were expressed at significantly higher levels in the NT-ESCs and HDFs compared to IVF-ESCs. These represented genes that were potentially incompletely silenced during reprogramming (FIG. 20B). In comparison, 171 genes in the iPSC lines that were potentially incompletely reactivated and 32 genes that were potentially incompletely silenced (FIG. 20B). Therefore, the number of affected genes was markedly higher in the iPSCs compared to the NT-ESCs.

Figure 20C:
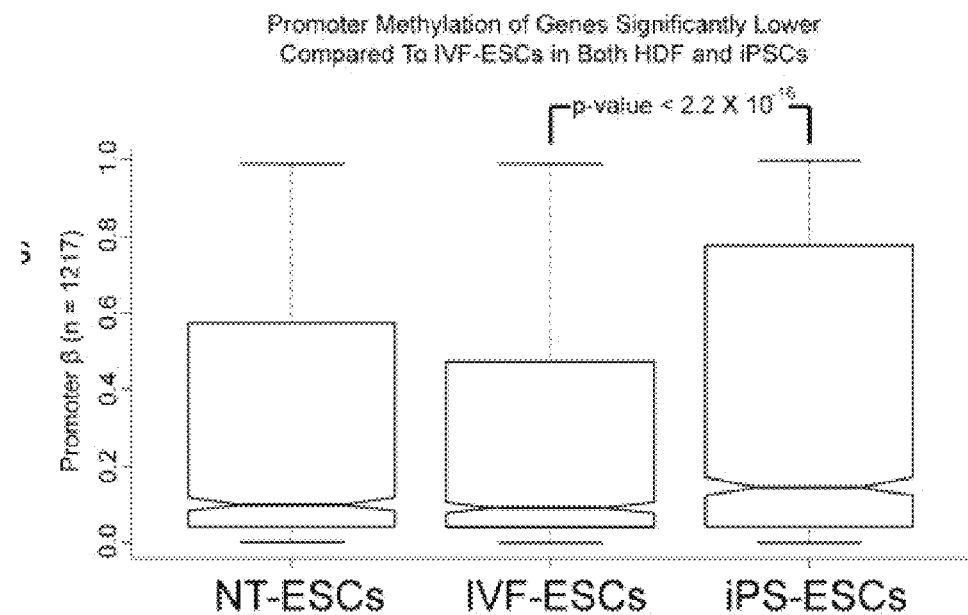
FIG. 20C is a set of Notched box plots represent the $\beta$ value of all probes in the promoter regions (−2000 bp to 500 bp) of the genes that were expressed at significantly lower levels (t-test FDR <0.05) in both the HDFs and the iPSCs (exhibiting transcriptional memory) when compared to the IVF-ESCs. The box represents the interquartile range (25th to 75th percentile), and the line within the box marks, the median. The notch in the box represents the 95% confidence interval around the median. The whiskers above and below the box contain 99.3% of the data and the number of CpGs interrogated is shown on the y-axis.

It was then examined whether the genes that exhibited transcriptional memory also showed promoter DNA methylation differences. Only the genes that were incompletely reactivated in our iPSC lines possessed significantly different methylation in their promoter regions (Mann-Whitney test $p<2.2\times10^{-16}$) when compared to IVF-ESC lines (FIG. 20C). This suggests that incomplete demethylation of promoter regions may have occurred during iPSC generation and resulted in transcriptional differences between our iPSCs and IVF-ESCs. Overall, the gene expression and DNA methylation results were consistent, and both suggested that NT-ESC lines are markedly more similar to IVF-ESCs than to iPSCs.

The invention claimed is:

1. A method of producing a human pluripotent embryonic stem cell, the method comprising:
    enucleating a human oocyte from a donation cycle of 15 or fewer oocytes by removing the MII spindle in a manner that does not lower levels of maturation promoting factor, thereby producing a cytoplast;
    contacting a human donor nucleus with an HVJ-E extract;
    contacting the cytoplast with the human donor nucleus thereby producing an SCNT embryo;
    treating the human oocyte and/or the cytoplast and/or the donor nucleus and/or the SCNT embryo with a protein phosphatase inhibitor;
    applying a first electroporation pulse to the SCNT embryo, thereby producing an activated SCNT embryo;

culturing the activated SCNT embryo in a first media comprising 6-DMAP;
culturing the activated SCNT embryo in a second media comprising TSA;
culturing the activated SCNT embryo in a third media thereby producing a blastocyst;
culturing the blastocyst on a feeder layer; and
selecting a cell with an embryonic stem cell-like morphology.

2. The method of claim 1 wherein the human oocyte was obtained from an oocyte donor previously treated with a GnRH antagonist.

3. The method of claim 2 wherein the GnRH antagonist comprises ganirelix.

4. The method of claim 1 further comprising obtaining the human oocyte from the oocyte donor.

5. The method of claim 1 wherein removing the MII spindle is performed using a polarized microscope.

6. The method of claim 1 wherein the donor nucleus is included within a donor cell.

7. The method of claim 6 further comprising contacting the donor cell with trypsin thereby producing a disaggregated donor cell.

8. The method of claim 1 wherein treating with the protein phosphatase inhibitor occurs during both enucleation of the human oocyte and contacting the SCNT embryo with the donor nucleus.

9. The method of claim 1 wherein the protein phosphatase inhibitor comprises caffeine.

10. The method of claim 9 further comprising treating the human oocyte and/or the enucleated oocyte and/or the donor nucleus and/or the SCNT embryo with at least 0.5 mM caffeine.

11. The method of claim 10 further comprising treating the human oocyte and/or the enucleated oocyte and/or the SCNT embryo with between 0.5 mM and 2.5 mM caffeine.

12. The method of claim 1 further comprising applying a second electroporation pulse.

13. The method of claim 12 wherein the first electroporation pulse is a 50 µs DC pulse of 2.7 kV cm$^{-1}$ and wherein the second electroporation pulse is a 50 µs DC pulse of 2.7 kV cm$^{-1}$.

14. The method of claim 1 wherein the first media comprises at least 2 mM 6-DMAP.

15. The method of claim 14 further comprising culturing the activated SCNT embryo in the first media for at least 4 hours.

16. The method of claim 1 wherein the second media comprises at least 10 nM TSA.

17. The method of claim 1 wherein the third media comprises BSA and β-mercaptoethanol.

18. The method of claim 1 further comprising characterizing the selected cells with embryonic stem-cell like morphologies as human pluripotent embryonic stem cells comprising donor nucleus nuclear DNA and oocyte donor mitochondrial DNA.

* * * * *